United States Patent
Ho et al.

(10) Patent No.: US 11,359,242 B2
(45) Date of Patent: Jun. 14, 2022

(54) METHOD TO IDENTIFY KEY MARKERS OF HUMAN PLURIPOTENT CELL-DERIVED SOMATIC CELLS THAT PREDICT MOLECULAR SIMILARITY TO IN VIVO TARGET CELLS

(71) Applicant: Cedars-Sinai Medical Center, Los Angeles, CA (US)

(72) Inventors: Ritchie Ho, Santa Monica, CA (US); Clive Svendsen, Pacific Palisades, CA (US)

(73) Assignee: CEDARS-SINAI MEDICAL CENTER, Los Angeles, CA (US)

(*) Notice: Subject to any disclaimer, the term of this patent is extended or adjusted under 35 U.S.C. 154(b) by 272 days.

(21) Appl. No.: 16/068,323

(22) PCT Filed: Jan. 6, 2017

(86) PCT No.: PCT/US2017/012492
§ 371 (c)(1),
(2) Date: Jul. 5, 2018

(87) PCT Pub. No.: WO2017/120443
PCT Pub. Date: Jul. 13, 2017

(65) Prior Publication Data
US 2019/0024176 A1    Jan. 24, 2019

Related U.S. Application Data

(60) Provisional application No. 62/276,146, filed on Jan. 7, 2016.

(51) Int. Cl.
*C12Q 1/6883* (2018.01)
*A61K 35/30* (2015.01)
*C12Q 1/6881* (2018.01)
*G01N 33/68* (2006.01)

(52) U.S. Cl.
CPC ............ *C12Q 1/6883* (2013.01); *A61K 35/30* (2013.01); *C12Q 1/6881* (2013.01); *G01N 33/6896* (2013.01); *C12Q 2600/118* (2013.01); *C12Q 2600/158* (2013.01); *G01N 2800/28* (2013.01)

(58) Field of Classification Search
None
See application file for complete search history.

(56) References Cited

U.S. PATENT DOCUMENTS

2010/0240090 A1    9/2010  Sakurada et al.
2013/0259842 A1*  10/2013  Rubin .................. A61K 35/545
                                                        424/93.21

FOREIGN PATENT DOCUMENTS

WO    2014210223 A1    12/2014
WO    2015048665 A2     4/2015
WO    2017/120443 A1    7/2017

OTHER PUBLICATIONS

Kirby (Brain 2011: 134; 506-517).*
Situma (Biomolecular Engineering 23 (2006) 213-231).*
Alves et al., Gene expression profiling for human iPS-derived motor neurons from sporadic ALS patients reveals a strong association between mitochondrial functions and neurodegeneration, Frontiers in Cellular Neuroscience, 2015, vol. 9(289), pp. 1-25.
Kiskinis et al., Pathways disrupted in human ALS motor neurons identified through genetic correction of mutant SOD1, Cell Stem Cell, 2014, vol. 14(6), pp. 1-28.
Mougeot et al., Microarray analysis of peripheral blood lymphocytes from ALS patients and the SAFE detection of the KEGG ALS pathway, BMC Medical Genomics, 2011, vol. 4(74), pp. 2-19.
Kudo et al., Integrative gene-tissue microarray-based approach for identification of human disease biomarkers: application to amyotrophic lateral sclerosis, Human Molecular Genetics, 2010, vol. 19(16), pp. 3233-3253.
Offen et al., Spinal cord mRNA profile in patients with ALS: comparison with transgenic mice expressing the human SOD-1 mutant, J Mol Neurosci, 2009, vol. 38, pp. 85-93.
Burkhardt et al., A cellular model for sporadic ALS using patient-derived induced pluripotent stem cells, Mol Cell Neurosci., 2013, vol. 56, pp. 1-20.
Patterson et al., Defining the nature of human pluripotent stem cell progeny, Cell Research, 2012, vol. 22, pp. 178-193.
Stein et al., A quantitative framework to evaluate modeling of cortical development by neural stem cells, Neuron., 2014, vol. 83(1), pp. 1-31.
International Search Report and Written Opinion for PCT/US2017/12492 filed Jan. 6, 2017, 8 pages.

* cited by examiner

*Primary Examiner* — Amanda Haney
(74) *Attorney, Agent, or Firm* — Nixon Peabody LLP

(57) ABSTRACT

Modeling Amyotrophic Lateral Sclerosis (ALS) with human induced pluripotent stem cells (iPSCs) aims to reenact embryogenesis, maturation, and aging of spinal motor neurons (spMNs) in vitro. As the maturity of spMNs grown in vitro compared to spMNs in vivo remains largely unaddressed, it is unclear to what extent this in vitro system captures critical aspects of spMN development and molecular signatures associated with ALS. Here, the Inventors compared transcriptomes among iPSC-derived spMNs, fetal, and adult spinal tissues. The Inventors resolved gene networks and pathways associated with spMN maturation and aging. These networks enriched for familial ALS genetic variants and were affected in sporadic ALS. Altogether, the Inventors' findings suggest that developing strategies to further mature and age iPSC-derived spMNs will provide more effective iPSC models of ALS.

5 Claims, 42 Drawing Sheets

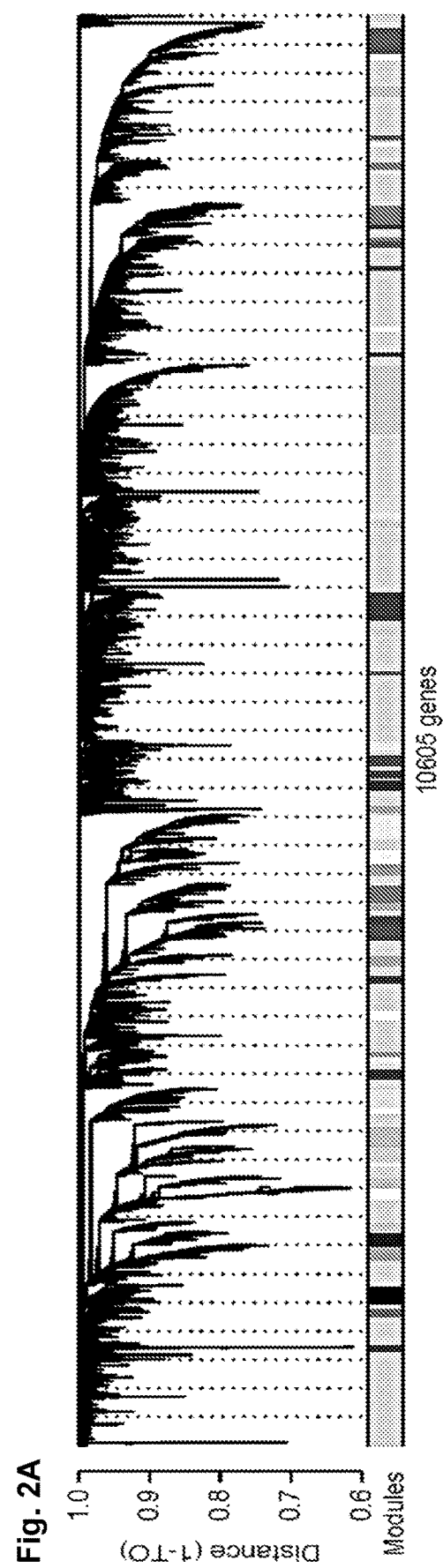

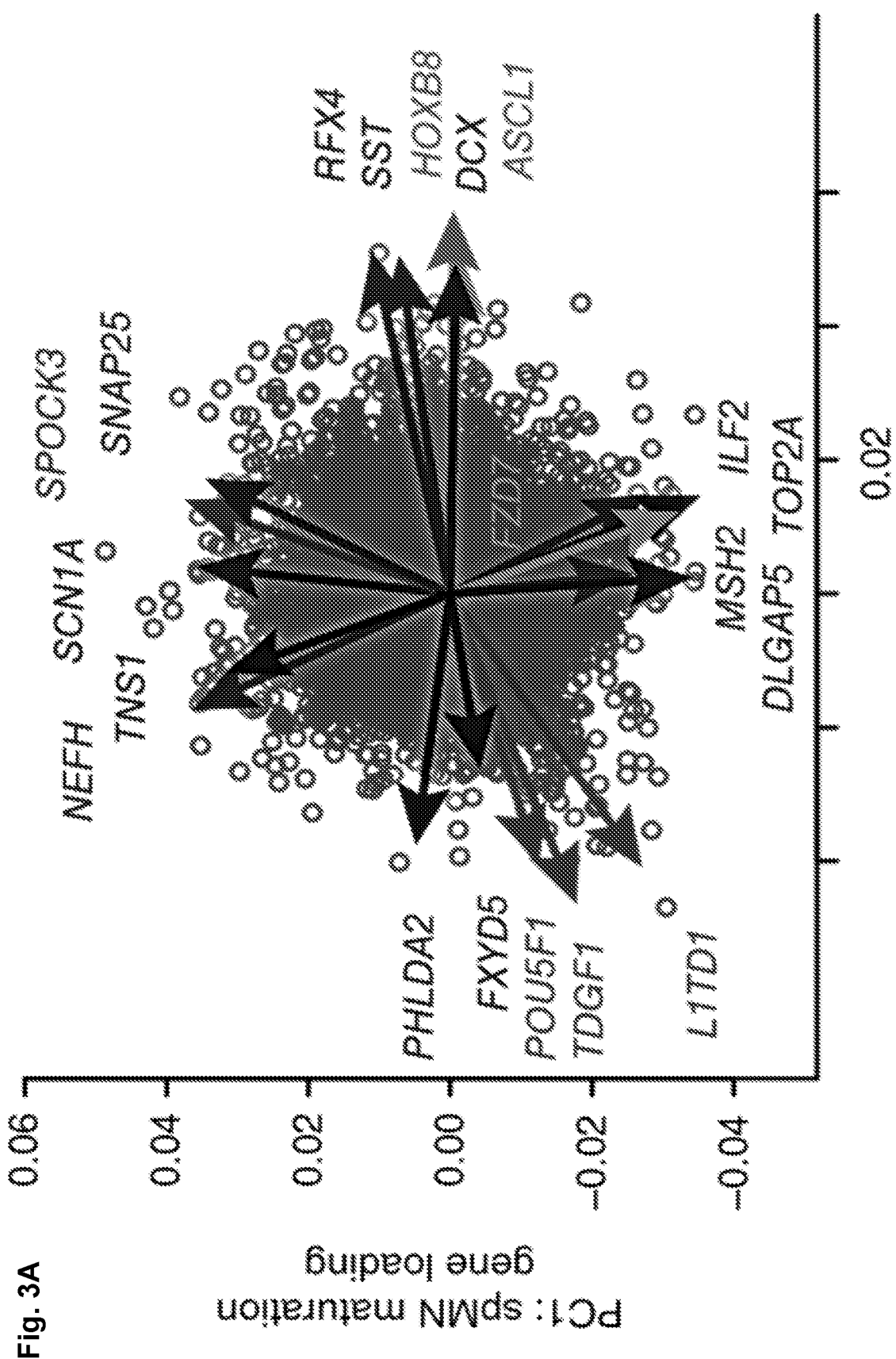

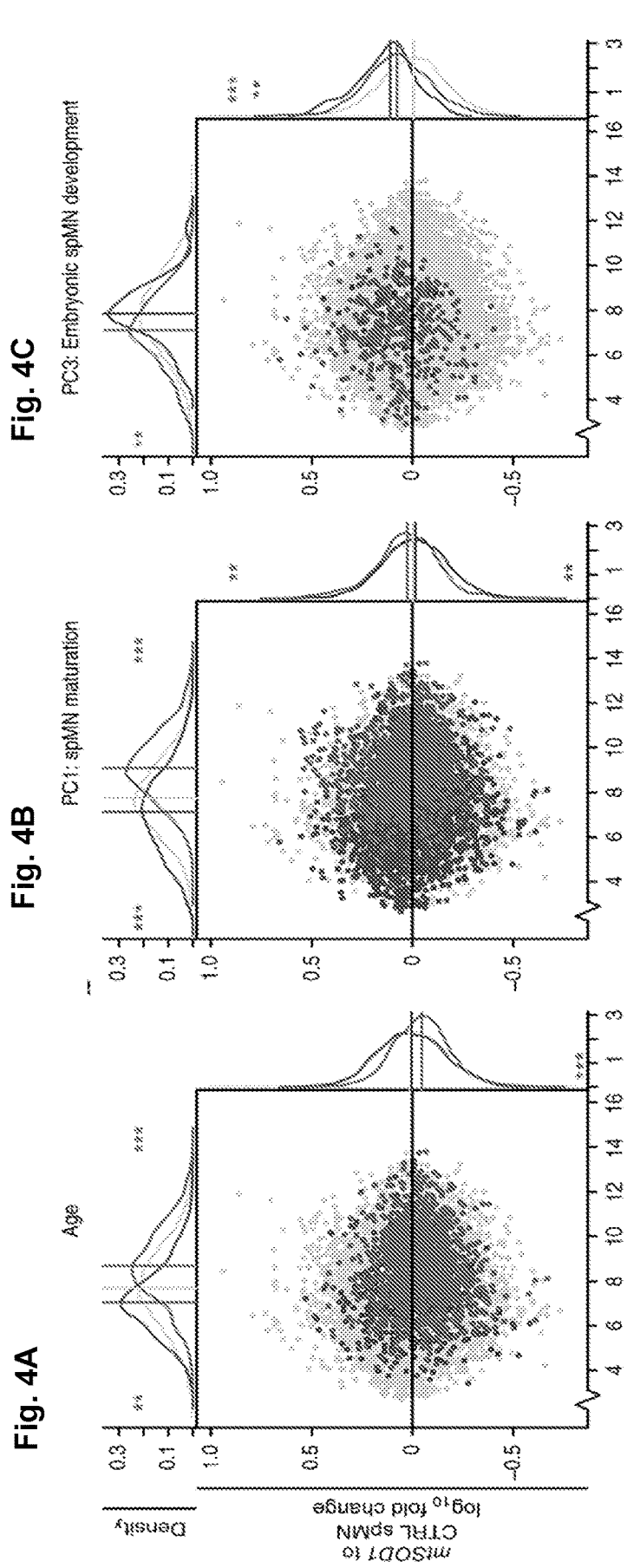

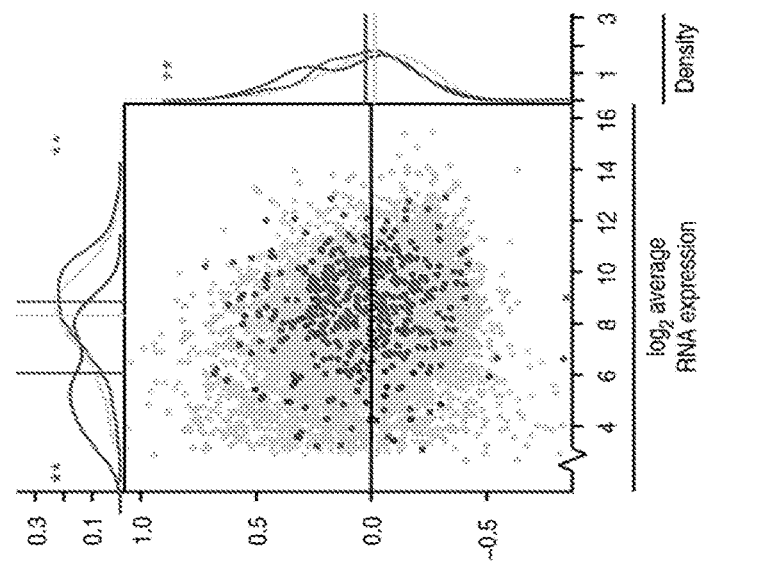
Fig. 4F
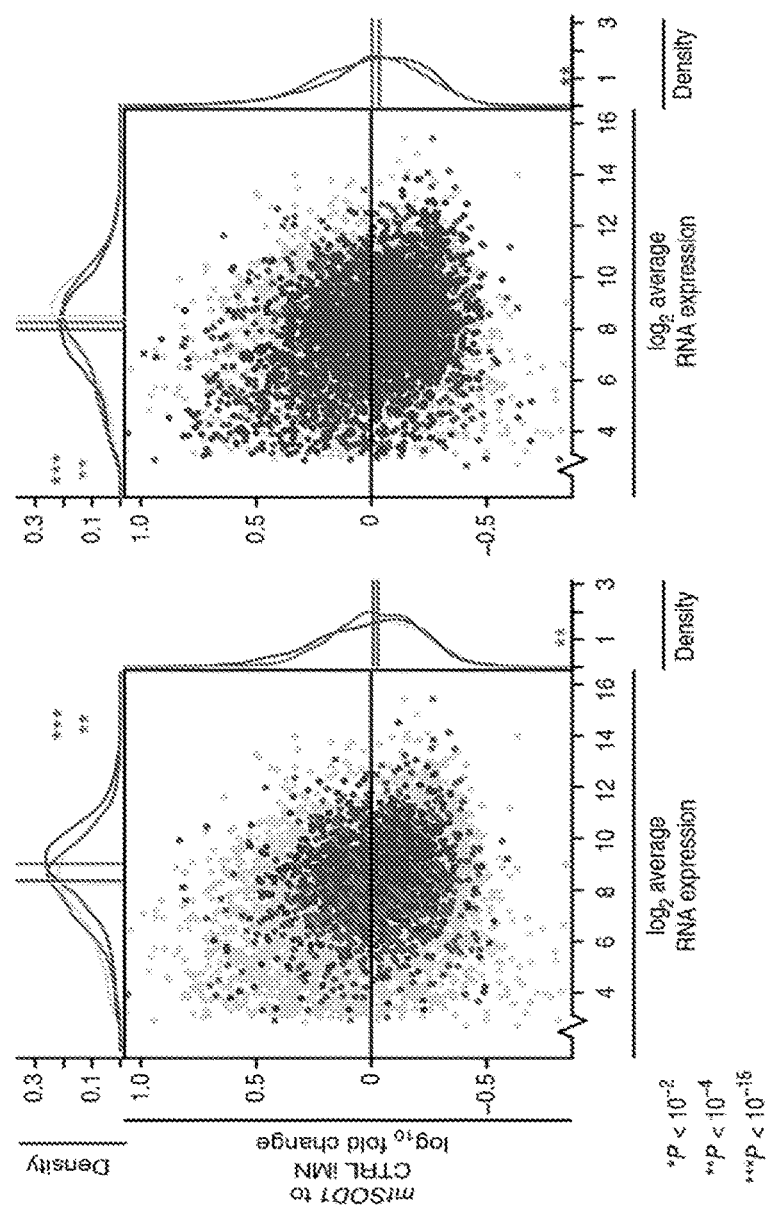
Fig. 4D
Fig. 4D

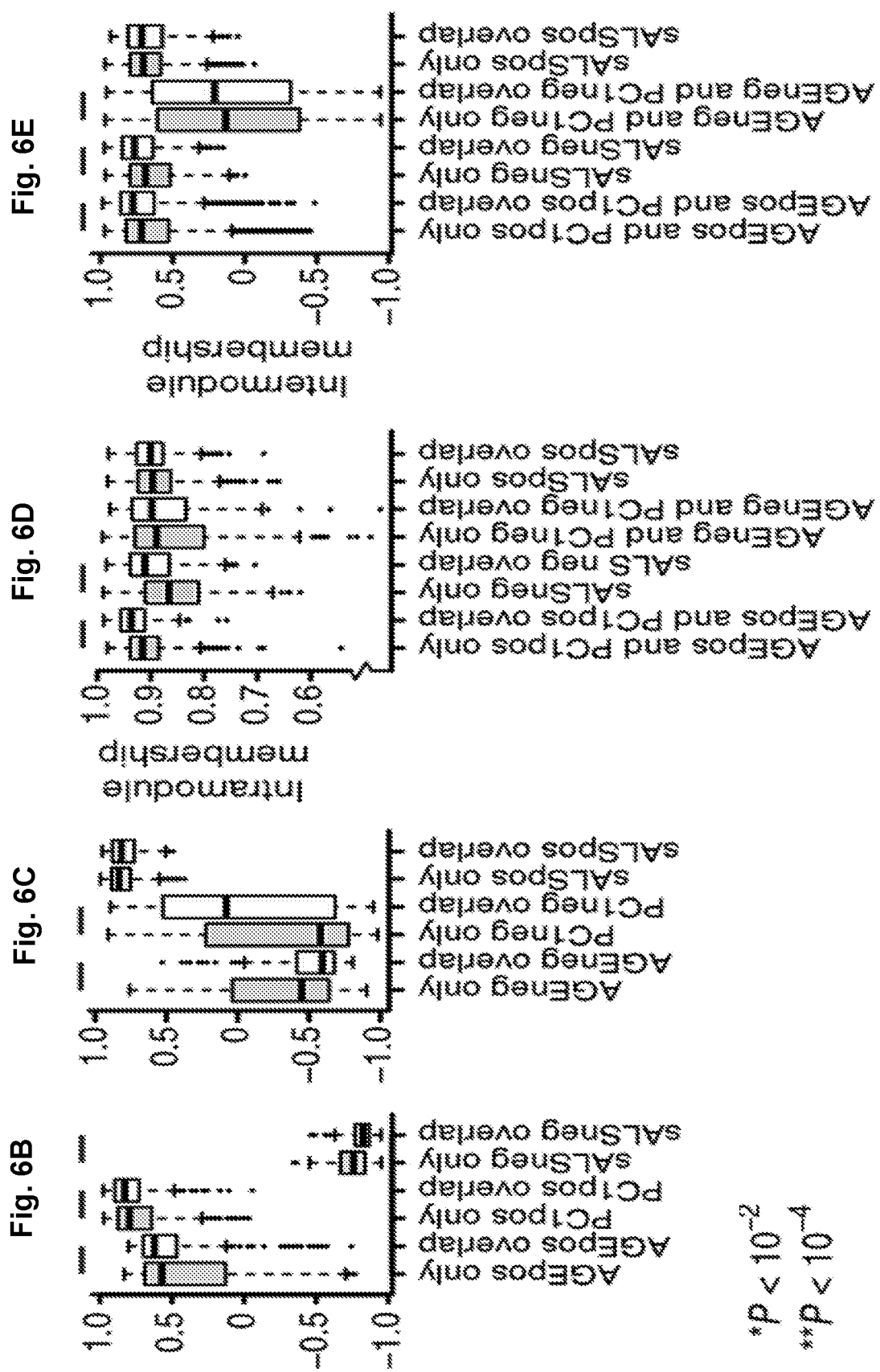

sALS positive

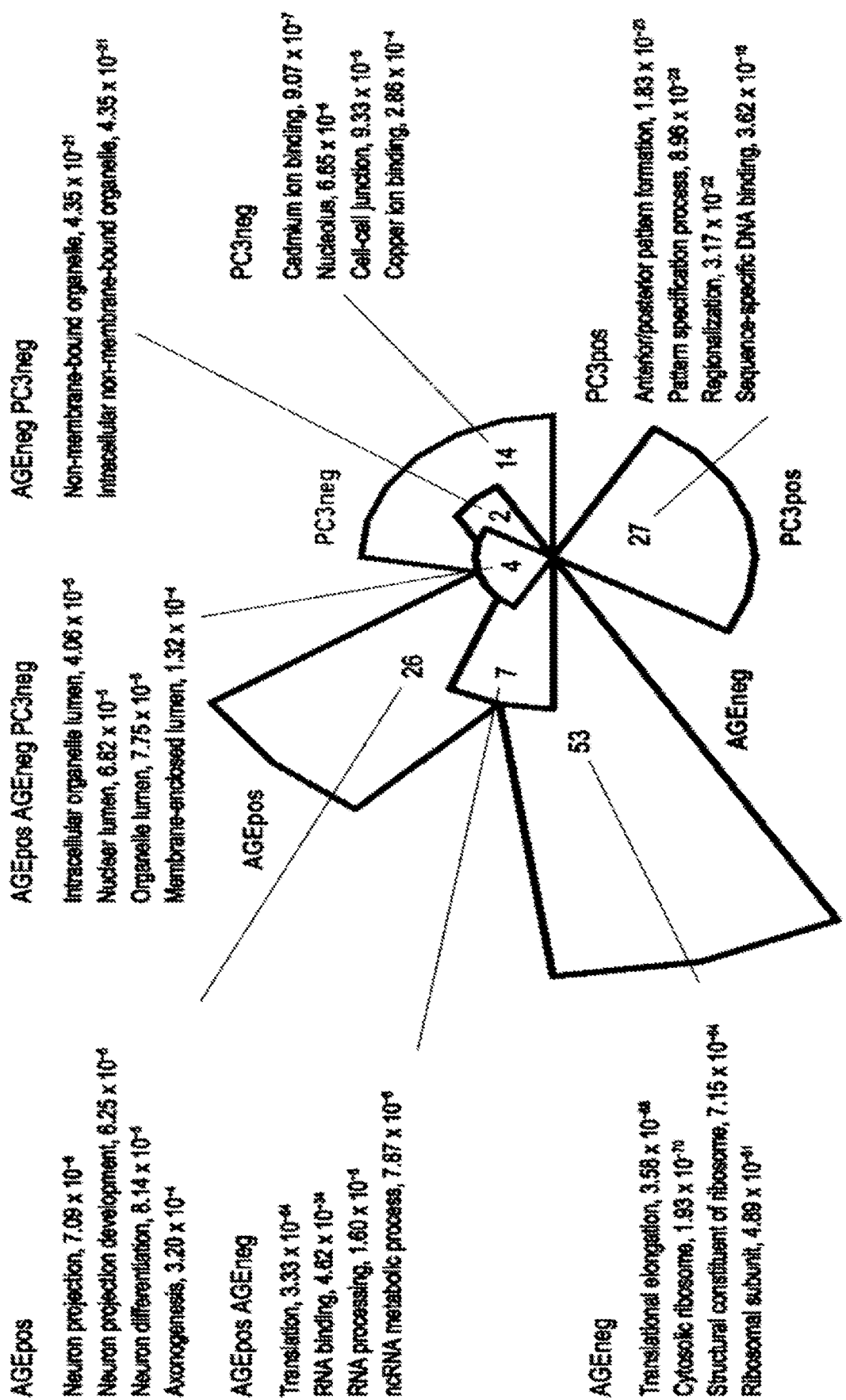

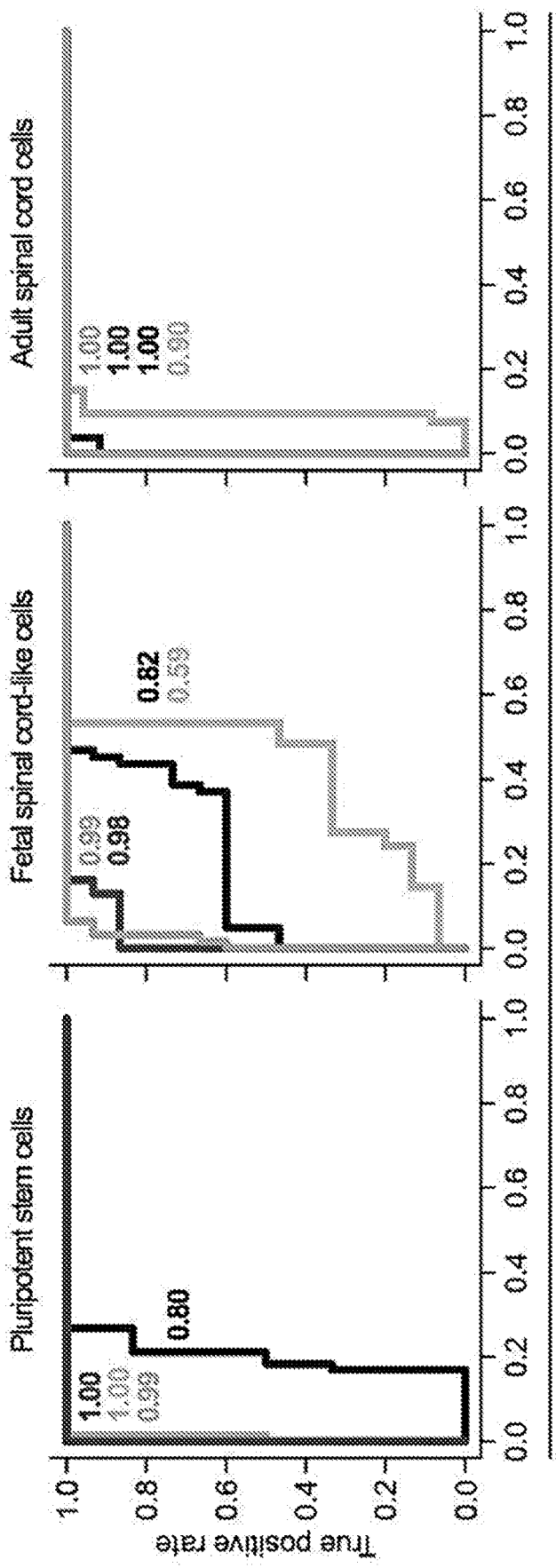

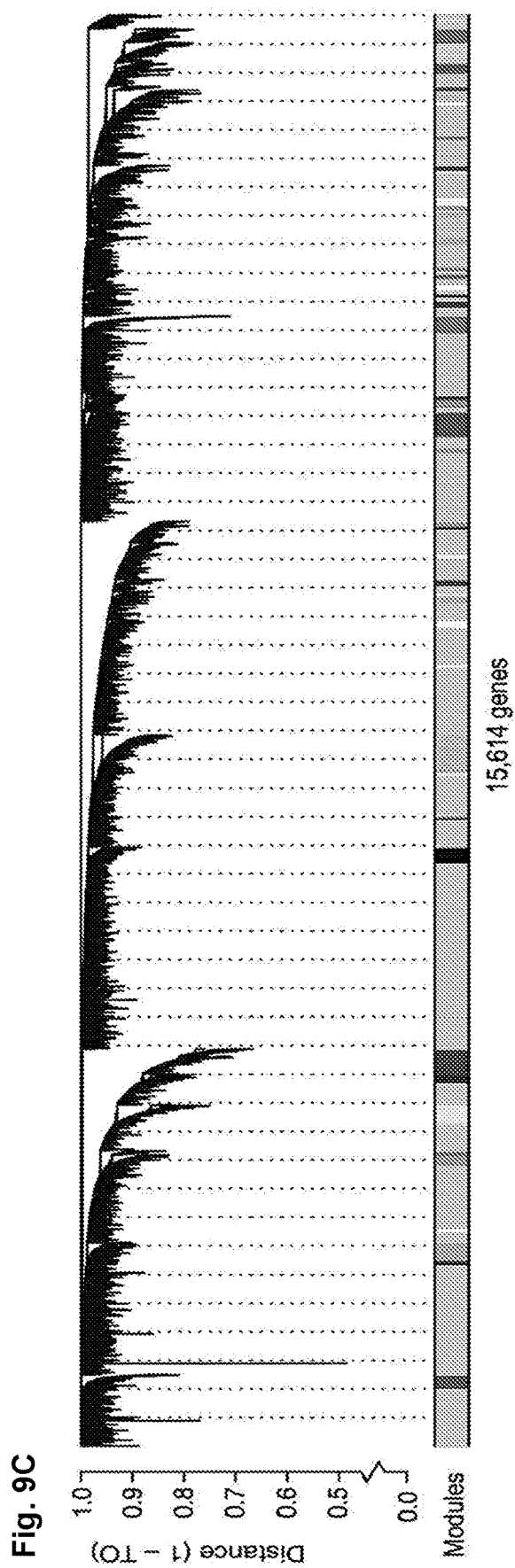

PC3pos sALSpos

Regulation of transcription, DNA-dependent, $1.19 \times 10^{-2}$
Regulation of RNA metabolic process, $1.15 \times 10^{-2}$
Transcription, $2.53 \times 10^{-4}$
Regulation of transcription, $4.51 \times 10^{-5}$
Regulation of transcription from RNA polymerase II promoter, $6.31 \times 10^{-7}$

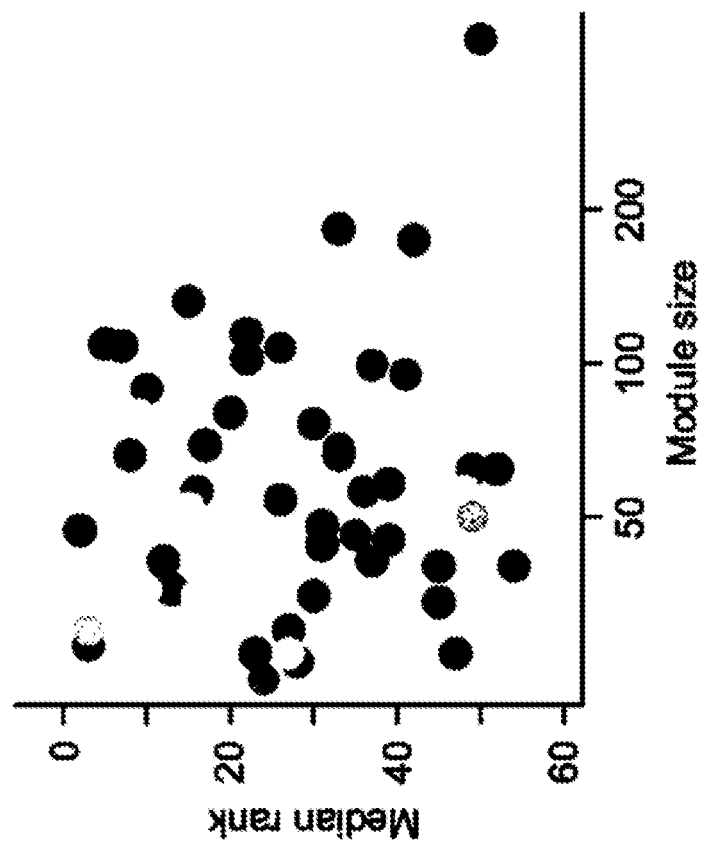
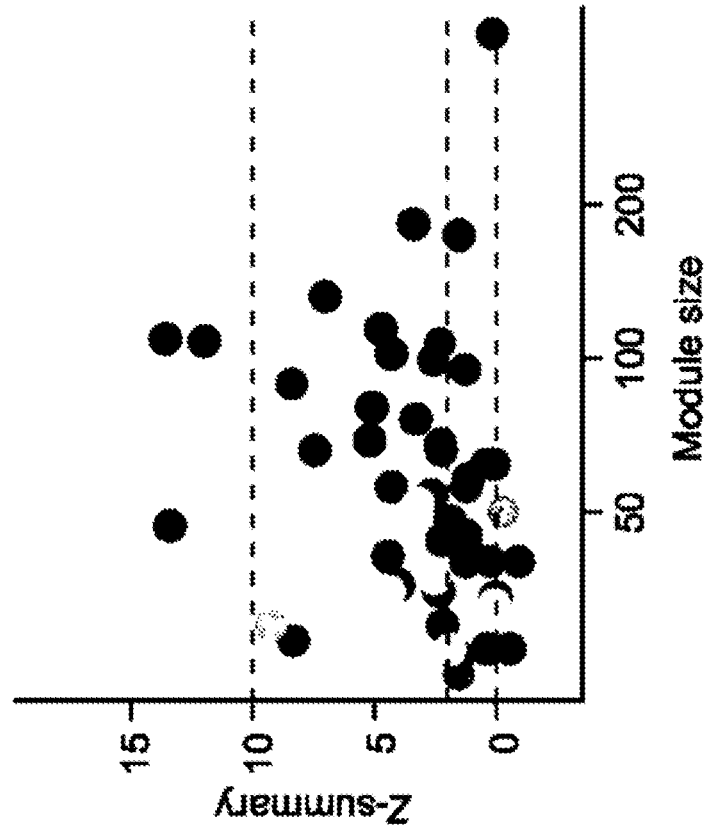
Fig. 13A
Fig. 13B

METHOD TO IDENTIFY KEY MARKERS OF HUMAN PLURIPOTENT CELL-DERIVED SOMATIC CELLS THAT PREDICT MOLECULAR SIMILARITY TO IN VIVO TARGET CELLS

CROSS-REFERENCE TO RELATED APPLICATIONS

This application is a National Phase of International Application No. PCT/US2017/012492, filed Jan. 6, 2017, which designated the U.S. and that International Application was published under PCT Article 21(2) in English. This application claims priority under 35 U.S.C. § 119(e) to U.S. Provisional Application No. 62/276,146, filed Jan. 7, 2016, the contents of which are herein incorporated by reference in their entirety.

FIELD OF THE INVENTION

Described herein are methods and compositions related to characterizing populations of cells differentiated cells from pluripotent stem cells.

BACKGROUND

Amyotrophic Lateral Sclerosis (ALS) is a devastating neurodegenerative disorder characterized by the death of motor neurons (MNs), typically presented in late adulthood, with a poor prognosis and no effective treatments. While animal models of ALS have effectively captured some molecular and physiological aspects of disease onset and progression, inherent genetic differences between humans and animal models limit the interpretation and relevance of these phenotypic results. A powerful, complementary in vitro system to animal models of ALS is patient-derived induced pluripotent stem cells (iPSCs). iPSCs derived from ALS patients possess the inherent advantages of harboring the patient's complex genetic makeup that contributes to their disease. In modeling ALS with iPSCs, the goal is to recapitulate in a dish the embryonic development, maturation, and aging of cell types thought to be involved with ALS pathology. Since spinal MNs (spMNs) are one of the primary cell types susceptible to cell death in ALS, and the embryonic development of spMNs have been well characterized and were the first MNs to be differentiated in vitro from mouse and human pluripotent cells, many studies have focused on optimizing in vitro differentiation protocols producing lower MNs from iPSCs. This methodology would thus enable the monitoring of disease onset in spMNs and reveal molecular mechanisms that can be therapeutically targeted.

However, the process through which ALS-afflicted spMNs progress from the embryonic state to the mature and aged state, the point at which they degenerate in disease occurs over the span of several decades. It therefore remains unclear whether the iPSC-derived MNs (iMNs), which are produced in vitro on the order of several weeks, can faithfully recapitulate the decades worth of complex in vivo events leading to MN degeneration. Notably, a systems level comparison has not been conducted between iMNs and adult spMNs, the in vivo counterparts that iMNs are meant to model. In this regard, there is a great need in the art to understand the similarity between the in vitro model and in vivo cells.

Described herein is a comparison of spMNs and iMNs as well as further examine the expression kinetics of gene networks as cell progress from the pluripotent state to the mature and aging adult state. These analyses indicated that iMNs are more similar to fetal rather than adult spinal tissue and revealed a sequential activation and repression of molecular pathways in spinal motor tissue through distinct stages of human life. Importantly, this approach identified certain networks enriched for clinically documented genetic variants associated with MN disease, revealing that maturation- and age-related pathways may play roles in disease initiation Finally, certain maturation- and aging-associated gene networks are dysregulated in familial and sporadic ALS. Collectively, these findings suggest that strategies to further mature and age iPSC-derived spMNs may provide more relevant iPSC models of ALS, and further identify methods and compositions for diagnosis, prognosis and treatment of these diseases.

SUMMARY OF THE INVENTION

Described herein is a method of characterizing age and/or maturation of a population of cells including providing a population of cells, and detecting expression of one or more genes, wherein expression of one or more of the genes indicates age and/or maturation of the population of cells. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the cells are neuronal cells. In other embodiments, the neuronal cells are obtained from a subject. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others. In other embodiments, the neuronal cells are differentiated from stem cells. In other embodiments, the stem cells are induced pluripotent stem cells (iPSCs). In other embodiments, the stem cells are embryonic stem cells (ESCs). In other embodiments, the neuronal cells are motor neurons.

Further described herein is a device for characterizing age and/or maturation of a population of cells including a device including one or more probes, binding the one or more probes to one or more genes, detecting expression of one or more genes, wherein the probes detect expression of one or more genes, wherein expression of one or more of the genes characterizes age and/or maturation of the population of cells. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the cells are neuronal cells. In other embodiments, the neuronal cells are obtained from a subject. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others. In other embodiments, the device is a microenvironment microarray. In other embodiments, the device is a microfluidic device. In other embodiments, the probes bind to nucleic acid. In other embodiments, the probes bind to proteins and/or peptides.

Further described herein is a method for prognosing and/or diagnosing a neurodegenerative disease and/or condition in a subject including, obtaining a sample from a subject, detecting expression of one or more genes, wherein expression of one or more of the genes prognoses and/or diagnoses a neurodegenerative disease and/or condition in the subject. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the sample includes a population of cells. In other embodiments, the cells are neuronal cells. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others.

BRIEF DESCRIPTION OF FIGURES

FIG. 1. iPSC-derived MNs resemble fetal rather than adult MNs

FIG. 2. Network analysis resolves co-expression modules FIG. 2A: WGCNA clustered 10605 genes across pluripotent cells, iMNs, fetal spinal tissues, and adult spinal tissues based on similar expression patterns. Height metric on dendrogram indicates topological overlap (TO) distance between genes. A dynamic tree-cutting algorithm grouped tightly co-expressed genes, illustrated as low hanging branches, into 55 modules represented by arbitrary colors directly below the branches. Genes falling onto the predominant light grey color are not classified into any module.

FIG. 3. Principal component and network analyses reveal key spMN maturation and embryonic development markers FIG. 3A: Gene loadings for 20 genes selected to best represent spMN maturation and embryonic spMN development. Colored arrows and gene labels depict gene loadings and module assignments for the 20 genes along PC1 and PC3. Open grey circles represent gene loadings for 10585 genes not selected for the panel.

FIG. 4. Gene expression networks are distinctively affected by familial ALS in spMNs and iMNs. Scatter and density plots depicting expression levels and mtSOD1-induced fold changes of age-, spMN maturation-, or embryonic spMN development-associated module genes (red for positive correlation, blue for negative correlation) and non-correlative genes (grey). Number of genes depicted in each like-colored category are indicated. X-axis indicates the normalized log 2 average mRNA expression values between each mtSOD1 to control comparison. Dashed line separates data sets performed on different gene expression profiling platforms. Y-axis indicates the fold change in average mRNA expression due to the mtSOD1 condition. Lines in density plots mark the median value of each distribution. Asterisks indicate the Kolmogorov-Smirnov two-sided P-value for like-colored categories tested against the grey distribution, and its location indicates the direction of the shifted distributions. Top panels FIG. 4A, FIG. 4B, FIG. 4C: mtSOD1 (n=3) versus control (n=3) spMNs (Kirby et al., 2011); bottom panels FIG. 4D, FIG. 4E, and FIG. 4F: mtSOD1 (n=2) versus control (n=3) iMNs (Kiskinis et al., 2014).

FIG. 5. spMN maturation and age modules are dysregulated in sporadic ALS

FIG. 6. Genes associated with spMN maturation, aging, and sALS tend to be hub genes FIG. 6B: Boxplots of gene significance for the overlapping and non-overlapping genes from the comparison depicted in FIG. 6A, left. Asterisks indicate P-values determined by the Wilcoxon rank-sum test. FIG. 6C: Similar presentation as in FIG. 6B, except applied to the overlapping and non-overlapping genes from the comparison depicted in FIG. 6A, right. FIG. 6D: Boxplots of intramodule membership for the overlapping and non-overlapping genes from the comparisons depicted in 6A. FIG. 6E: Boxplots of intermodule membership for the overlapping and non-overlapping genes from the comparisons depicted in 6A.

FIG. 7. Gene co-expression modules that correlate with age, spMN maturation, and embryonic spMN development enrich for distinct and overlapping pathways (Related to FIG. 2) FIG. 7B: Chow-Ruskey diagram illustrating the number of overlapping and distinct GO terms (Bonferroni-corrected p-value <0.05) enriched in modules identified as significantly correlated or anti-correlated to age (AGEpos or AGEneg, respectively) or embryonic spMN development (PC3pos or PC3neg, respectively). Representative pathways are listed in grey boxes extending from the diagram, along with the lowest Bonferroni-corrected p-values across all modules.

FIG. 8. Combined principal component and weighted gene co-expression network analyses reduce the number of key spMN maturation and embryonic development markers (Related to FIG. 3) FIG. 8B-FIG. 8D) ROC analysis performed on three methods classifying samples in the validation data set as pluripotent stem cells (FIG. 8B), fetal-like cells (FIG. 8C), or adult spinal cord cells (FIG. 8D). Classifications were based on sample correlation to the median expression values of target cell types in the training data set (red) or based on sample coordinates along the spMN maturation or embryonic development principal components generated from 6640 genes (black) or 20 genes (blue). The area under the curve (AUC) is shown next to each like-colored curve, and summarizes the overall performance of each classification method.

FIG. 9. Gene co-expression modules in spMNs correlate with sALS disease status (Related to FIG. 5) FIG. 9C: WGCNA clustered 15614 genes across sALS and control spMNs based on similar expression patterns. Height metric on dendrogram indicates topological overlap (TO) distance between genes. A dynamic tree-cutting algorithm grouped tightly co-expressed genes, illustrated as low hanging branches, into 52 modules represented by arbitrary colors directly below the branches. Genes falling onto the predominant light grey color are not classified into any module.

FIG. 11.

FIG. 12. FIG. 13A: Measure of how well 55 modules defined in the iMN data set are preserved in the sALS data set. The Z-summary statistic (y-axis) for is plotted against module size (x-axis). Data points reflect module color. Dashed green line indicate threshold at Z=10, and dashed blue line indicate threshold at Z=2. For the likelihood of module preservation, Z-summary>10 indicates strong evidence; 10>Z-summary>2 indicates moderate to weak evidence, and 2>Z-summary indicates no evidence. FIG. 13B: Measure of how well 55 modules defined in the iMN data set are preserved in the sALS data set, as a relative comparison among modules. The median rank statistic (y-axis) is plotted against module size (x-axis). Data points reflect module color. Low median rank values indicate a high preservation.

DETAILED DESCRIPTION

Figure 1A:
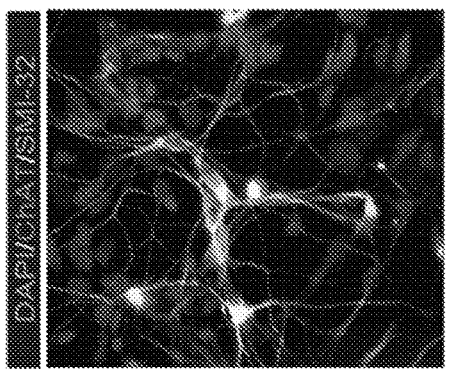
FIG. 1A: Immunostaining of iMNs used in expression profiling. ChAT (red) and SMI-32 (green) positive cells indicate the presence of MNs differentiated from iPSCs. Nuclear DAPI stains are shown in blue.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22$^{nd}$ ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3$^{rd}$ ed., revised ed., J. Wiley & Sons (New York, N.Y. 2006); Smith, March's Advanced Organic Chemistry Reactions, Mechanisms and Structure 7$^{th}$ ed., J. Wiley & Sons (New York, N.Y. 2013); Singleton, Dictionary of DNA and Genome Technology 3$^{rd}$ ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2$^{nd}$ ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 July, 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Amyotrophic lateral sclerosis (ALS), also referred to as Lou Gehrig's disease, is a debilitating disease characterized by degeneration of motor neurons causing rapidly progressive weakness, muscle atrophy, and muscle spasticity. The causes of progressive loss of upper and lower motor neurons in ALS remain largely unknown. Ninety to 95% of cases are sporadic (SALS) and 5-10% of cases are familial (FALS). A number of genes have been discovered as causative for classical familial ALS, namely SOD1, TDP-43/TARDBP, FUS/TLS, OPTN, and VCP These genes collectively account for 25% of familiar ALS (FALS), whereas repeat mutation in C9PORF72 alone can be identified in 40% or more of FALS cases in a population. In addition, studies comparing C9ORF72 mutation with other ALS mutations have demonstrated a more severe disease course with rapid progression, higher rate of bulbar onset (muscle weakness first beginning in the mouth and throat), greater rates of cognitive impairment and frontotemporal dementia (FTD), manifestation at an older age, and generally shorter survival times.

Modeling Amyotrophic Lateral Sclerosis (ALS) with human induced pluripotent stem cells (iPSCs) aims to reenact embryogenesis, maturation, and aging of spinal motor neurons (spMNs) in vitro. As the maturity of spMNs grown in vitro compared to spMNs in vivo remains largely unaddressed, it is unclear to what extent this in vitro system captures critical aspects of spMN development and molecular signatures associated with ALS. Here, the Inventors compared transcriptomes among iPSC-derived spMNs, fetal, and adult spinal tissues. This approach produced a maturation scale revealing that iPSC-derived spMNs were more similar to fetal spinal tissue than to adult spMNs. Additionally, the Inventors resolved gene networks and pathways associated with spMN maturation and aging. These networks enriched for familial ALS genetic variants and were affected in sporadic ALS. Altogether, the Inventors' findings suggest that developing strategies to further mature and age iPSC-derived spMNs will provide more effective iPSC models of ALS.

Described herein is a method of characterizing age and/or maturation of a population of cells including providing a population of cells, and detecting expression of one or more genes, wherein expression of one or more of the genes indicates age and/or maturation of the population of cells. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the cells are neuronal cells. In other embodiments, the neuronal cells are obtained from a subject. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others. In other embodiments, the neuronal cells are differentiated from stem cells. In other embodiments, the stem cells are induced pluripotent stem cells (iPSCs). In other embodiments, the stem cells are embryonic stem cells (ESCs). In other embodiments, the neuronal cells are motor neurons.

Also described herein is a device for characterizing age and/or maturation of a population of cells including a device including one or more probes, binding the one or more probes to one or more genes, detecting expression of one or more genes, wherein the probes detect expression of one or more genes, wherein expression of one or more of the genes characterizes age and/or maturation of the population of cells. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the cells are neuronal cells. In other embodiments, the neuronal cells are obtained from a subject. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others. In other embodiments, the neuronal cells are differentiated from stem cells. In other embodiments, the stem cells are induced pluripotent stem cells (iPSCs). In other embodiments, the stem cells are embryonic stem cells (ESCs). In other embodiments, the neuronal cells are motor neurons.

In other embodiments, the device is a microenvironment microarray. For example, proteins can be spotted in combinatorial format on the array located in a multi-well cell culture dish. Cells are incubated over the array and preferentially bind to certain spots. Further examples of microenvironment microarrays include, for example, Lin et al., (2012) Fabrication and use of microenvironment microarrays (MEArrays). J Vis Exp. 11, 68 and Ranga et al., (2014) 3D niche microarrays for systems-level analyses of cell fate. Nat Commun. 5:4324, which are incorporated by reference herein. In other embodiments, the device is a microfluidic device. In other embodiments, the probes bind to nucleic acid. In other embodiments, the probes bind to proteins and/or peptides.

Further described herein is a method for prognosing and/or diagnosing a neuronal disease and/or condition in a subject including obtaining a sample from a subject, detecting expression of one or more genes, wherein expression of one or more of the genes prognoses and/or diagnoses a neuronal disease and/or condition in the subject. In other embodiments, the one or more genes are selected from the group consisting of: NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2. In other embodiments, the sample includes a population of cells. In other embodiments, the cells are neuronal cells. In other embodiments, the subject is afflicted with a neurodegenerative disease and/or condition. In other embodiments, the neurodegenerative disease and/or condition includes Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others. In other embodiments, expression of one or more genes suggests a treatment regimen.

Described herein is a method of comparing transcription state of in vitro differentiated cells to in vivo counterparts. In various embodiments, qRT-PCR detects one or more genes capable of characterizing a population of cells. In various embodiments, the one or more genes are capable of molecular profiling substantially similar to a larger number of genes using projection and dimensional reduction. For example, 10, 20, 30, or 40 genes are capable of molecular profiling of a population of cells in a substantially similar manner to whole genome transcriptional profiling. In various embodiments the cells are neuronal cells. In other embodiments, the neuronal cells are differentiated from stem cells. In other embodiments, the stem cells are induced pluripotent stem cells (iPSCs). In other embodiments, the stem cells are embryonic stem cells (ESCs). In other embodiments, the neuronal cells are motor neurons.

Example 1

Experimental Procedures for Sample Preparation iMN differentiation was performed as previously described (Sareen et al., 2013). Sareen et al. (2013). Targeting RNA foci in iPSC-derived motor neurons from ALS patients with a C9ORF72 repeat expansion. *Science translational medicine* 5, 208ra149. HB9::GFP positive MNs and HB9::GFP negative cells were produced as previously described in Amoroso et al. (2013). Accelerated high-yield generation of limb-innervating motor neurons from human stem cells. *The Journal of neuroscience: the official journal of the Society for Neuroscience* 33, 574-586. Fetal tissue was obtained from the Birth Defects Research Laboratory at the University of Washington under their approved IRB, consent, and privacy guidelines. All protocols were performed in accordance with the Institutional Review Board's guidelines at the Cedars-Sinai Medical Center under the auspice IRB-SCRO Protocol Pro00021505. Total RNA was isolated from all frozen spinal sections using the RNeasy kit (QIA- GEN) with on column DNase digestion. RNA expression profiling was performed on the Affymetrix GeneChip Human Genome U133 Plus 2.0 Arrays. The accession number for the microarray data produced in this study is GEO: GSE75701. Pearson correlations, statistical tests, and multiple testing corrections were performed in R. Unsupervised hierarchical clustering was performed in Cluster 3.0 and heat maps were visualized using Java Treeview. Principal component analysis (PCA) was performed in Cluster 3.0 or R. WGCNA was performed using its package in R. The ROCR package was used to calculate and plot the Receiver Operator Characteristics and Area Under the Curve analyses. Hypergeometric tests for module enrichment were performed using custom scripts applying the dhyper function in R. Cytoscape 3.0 was used to visualize network topology.

Example 2

Tissue Culture and Processing, RNA Extraction, and Immunofluorescence Analysis iMN differentiation was performed as described in Sareen et al., 2013. Briefly, mTeSR1 medium was removed from confluent iPSC cultures and replaced with Iscove's modified Dulbecco's medium supplemented with 2% B27-vitamin A and 1% N2 (neural induction medium) for six days. The cells were then Accutase-treated to single cell suspension, and centrifuged in 384-well PCR plates in the presence of Matrigel and the neural induction medium (now using Neurobasal medium) that was further supplemented with 0.1 µM all-trans retinoic acid. After suspension culture for nine days, 1 µM purmorphamine was added to the medium and aggregates were cultured for another eight days. Thereafter, dissociated aggregates were plated onto poly-ornithine/laminin-coated coverslips and cultured in Dulbecco's modified Eagle's medium (DMEM)/F12 supplemented with 2% B27, 0.1 µM all-trans retinoic acid, 1 µM purmorphamine, 1 µM dibutyryl cyclic adenosine monophosphate, 200 ng/ml ascorbic acid, 10 ng/ml brain-derived neurotrophic factor, and 10 ng/ml glial cell linederived neurotrophic factor for 7 weeks. HB9::GFP positive MNs and HB9::GFP negative cells were produced as described in Amoroso et al., 2013. Specifically, the samples analyzed in this study were differentiated using 200 ng/ml SHH as a ventralizing factor.

Fetal tissue was obtained from the Birth Defects Research Laboratory at the University of Washington under their approved IRB, consent, and privacy guidelines. All protocols were performed in accordance with the Institutional Review Board's guidelines at the Cedars-Sinai Medical Center. Upon receipt, tissue samples were renamed D52, D53, D63, or D97 to reflect their estimated gestational stage. Samples arrived as fully or partially intact spinal columns, and spinal columns were opened prior to shipment. Vertebrae were removed and were partitioned into cervical, thoracic, and lumbar sections. Since only spinal columns were received, the exact anatomical reference for each somite could not be accurately determined, therefore the labeling of cervical, thoracic, and lumbar sections were estimated.

Figure 11A:
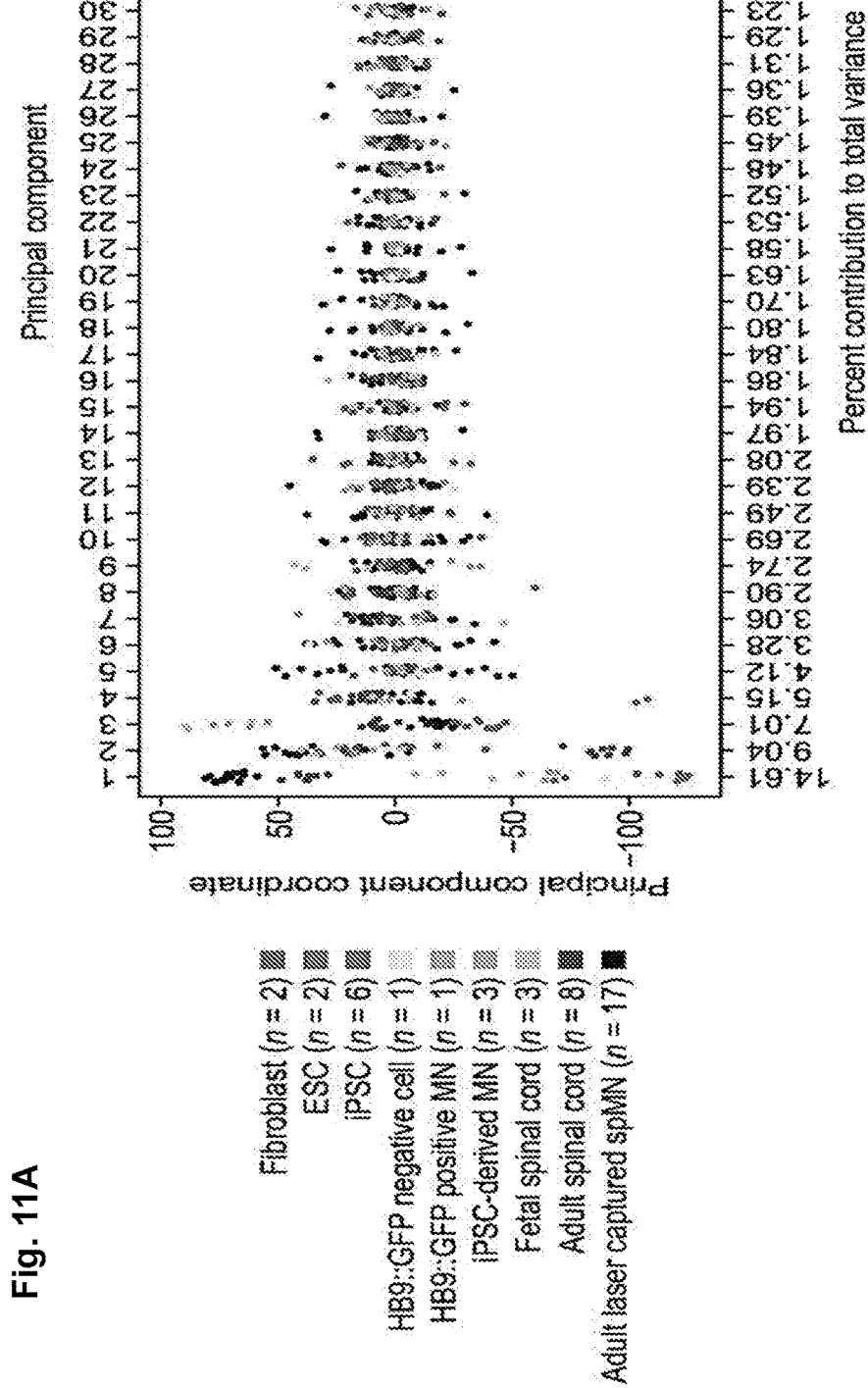
FIG. 11A: Principal component analysis of 10,605 mRNA transcripts in n=43 samples. Y-axis depicts sample coordinate along each principal component. The percent contribution to the total variance of the data by each principal component is shown along the x-axis. In order to reduce obscuration, data points are jittered randomly along the x-axis within each bin. The color legend for tissue types is indicated to the left.
Figure 11B:
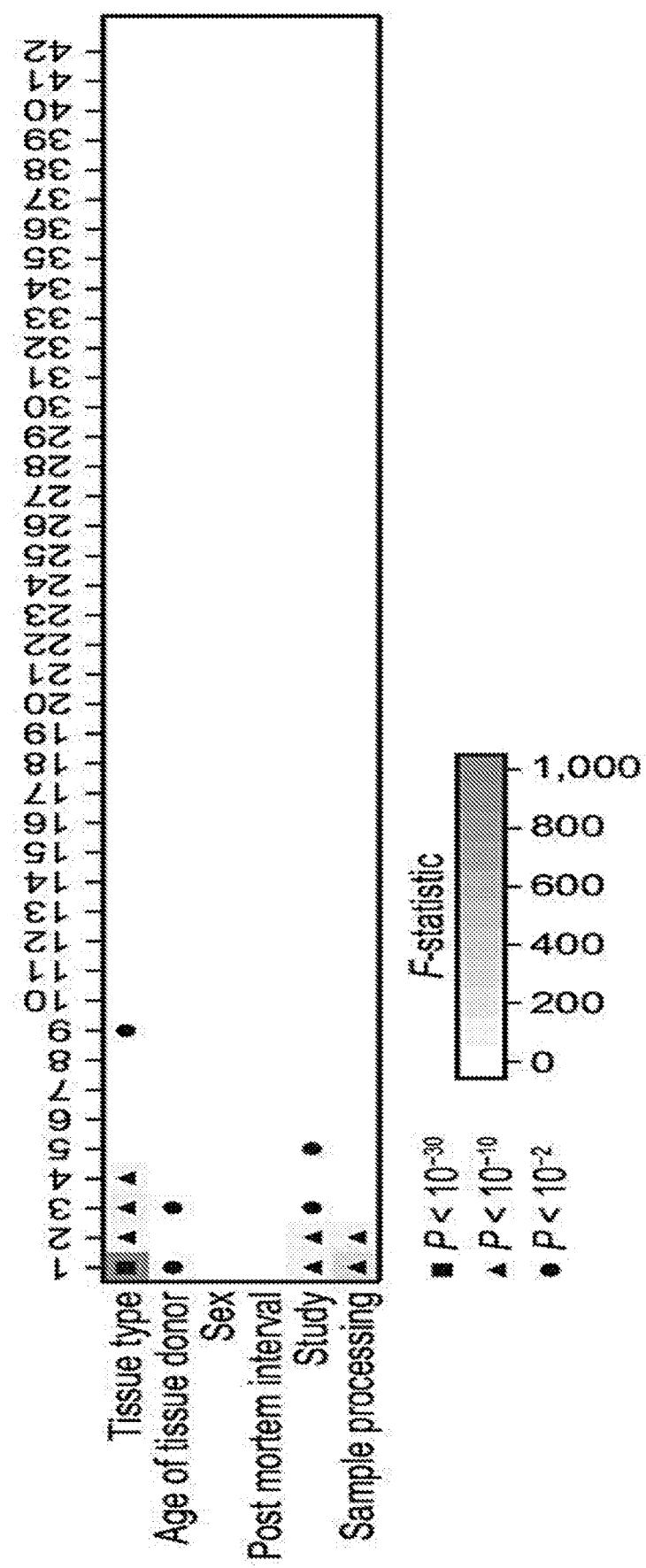
FIG. 11B: Regression analysis of linear models generated by using 6 sample traits as predictors and coordinates along 42 principal component as dependent variables. Heat map indicates F-statistic. Bonferroni-corrected P-values thresholds are indicated. Sample coordinates along PC1 to 4 are best explained by tissue type.
Figure 12A:
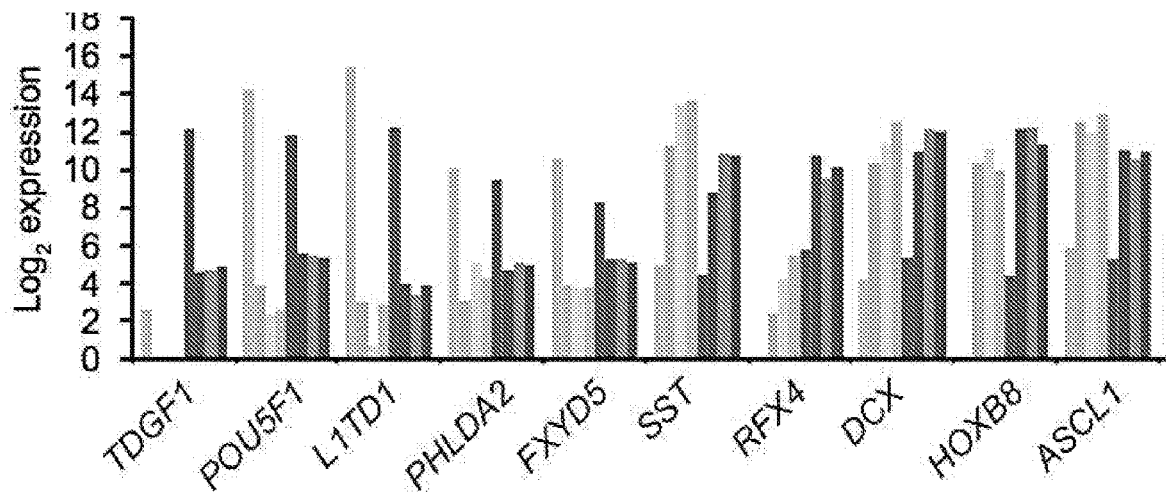
FIG. 12A: mRNA expression values compared between RT-qPCR and microarray for an iPSC line and its iMN derivative, as well as for fetal spinal cord (fSC) samples at gestational days 52 and 53. Data were obtained from the same sample of RNA used in both platforms. RT-qPCR expression values based on the average of n=3 technical replicates.
Figure 12A:
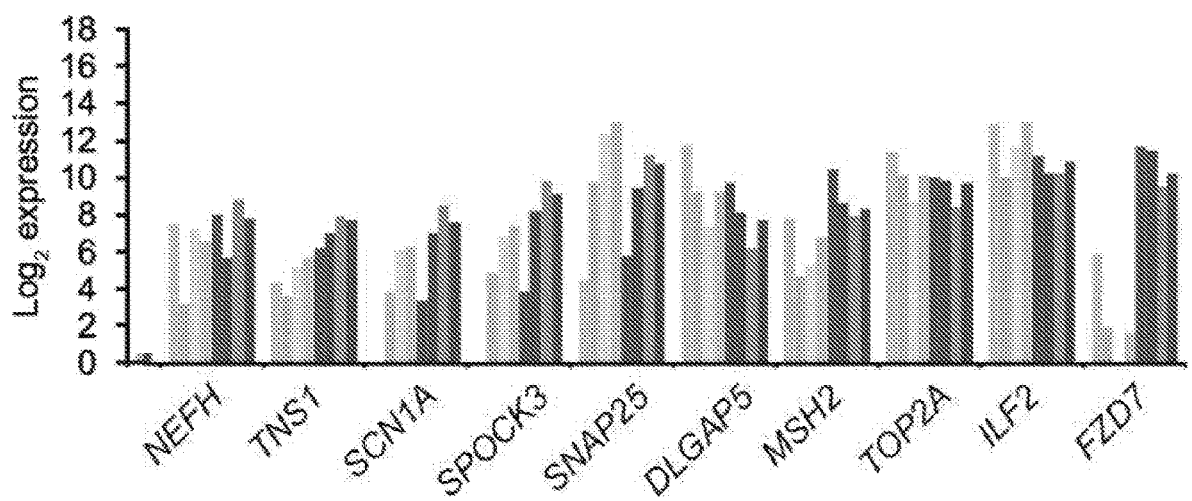
Figure 12A:
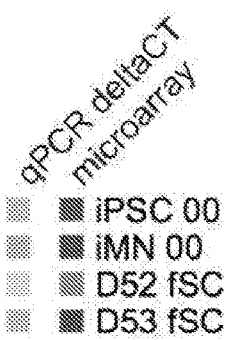
Figure 12B:
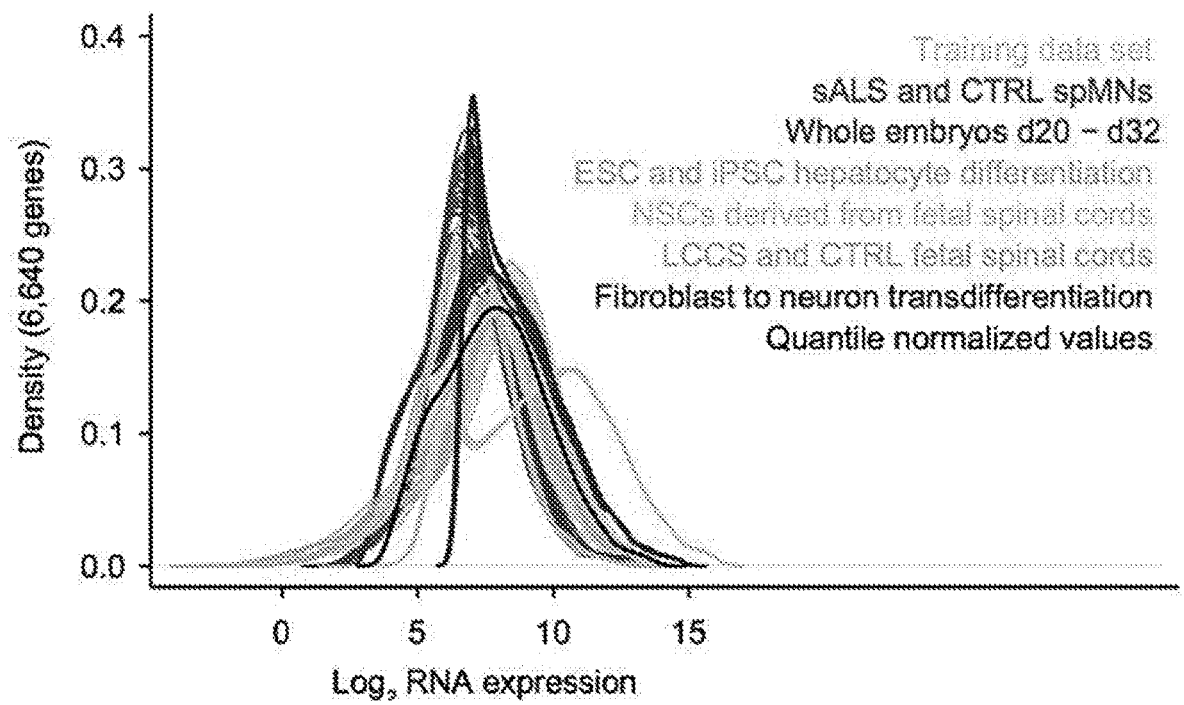
FIG. 12B: Gene expression density plot for 6,640 overlapping genes represented in the training data set as well as in the validation data sets, totaling 120 samples. Each line represents the gene expression distribution from one sample. Colors denote the study from which they were obtained. Black line represents the quantile normalized distribution of all samples.
Figure 12C:
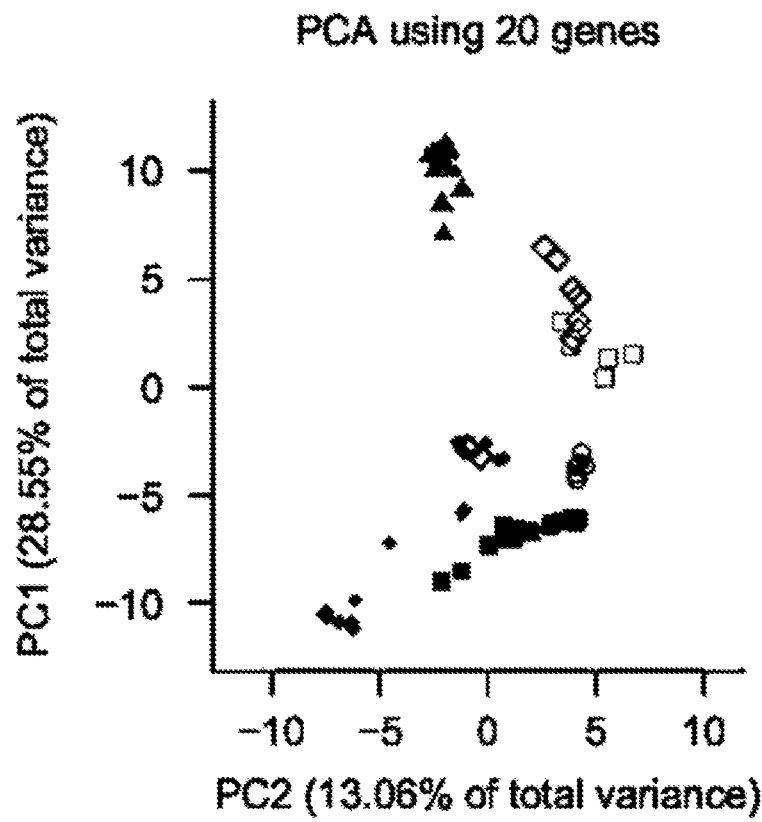
FIG. 12C: Principal component analysis performed on 20 gene expression values across 77 samples represented in b without the 43 samples in the training set. Samples are plotted by their coordinates along PC1 and PC2. ROC analysis performed on four methods classifying samples in the validation data set (in addition to two human fibroblast samples, n=79 samples) as pluripotent stem cells FIG. 13.
Figure 13C:
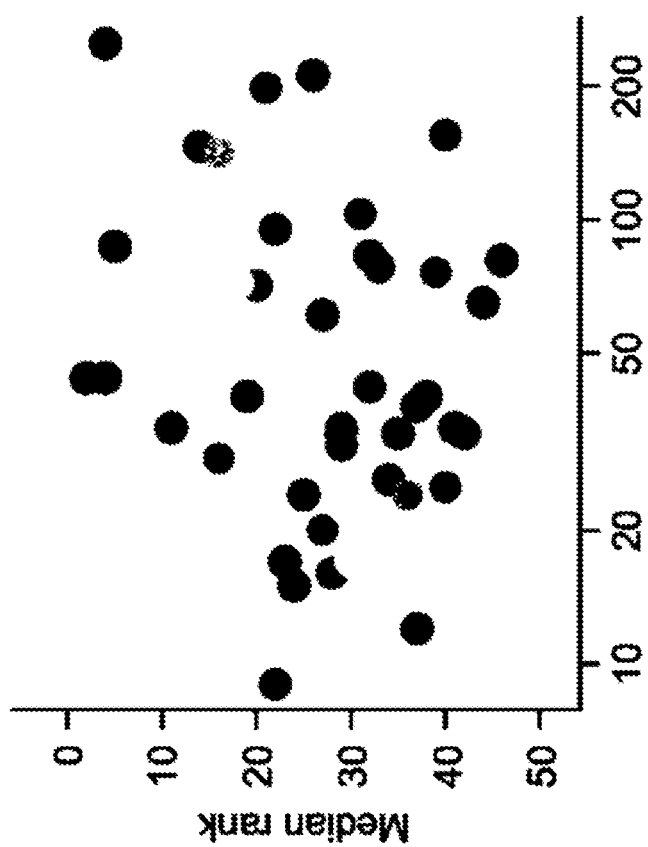
FIG. 13C: As in FIG. 13A, except applied to 52 modules defined in the sALS data set and tested for preservation in the iMN data set.
Figure 13D:
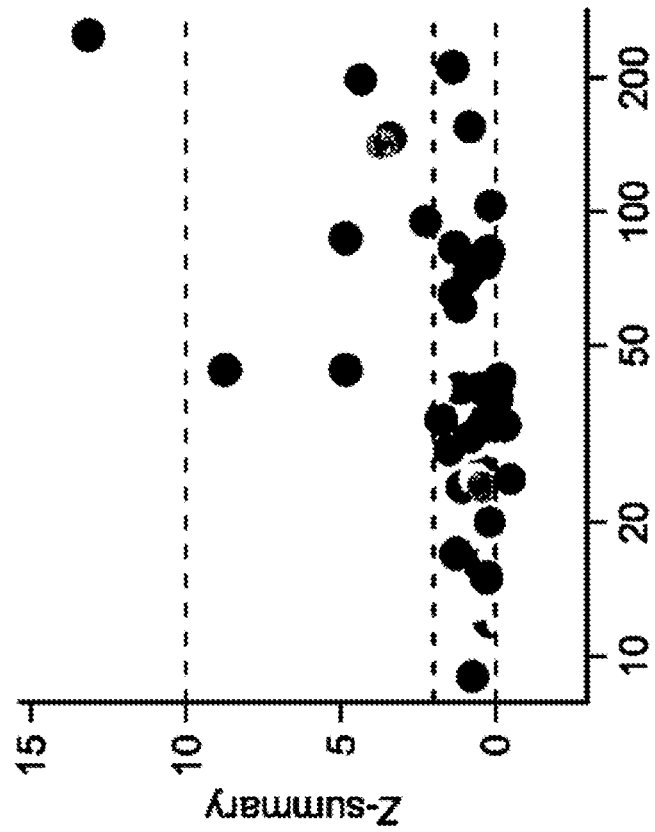
FIG. 13D: As in FIG. 13B, except applied to 52 modules defined in the sALS data set and tested for preservation in the iMN data set.
Figure 13E:
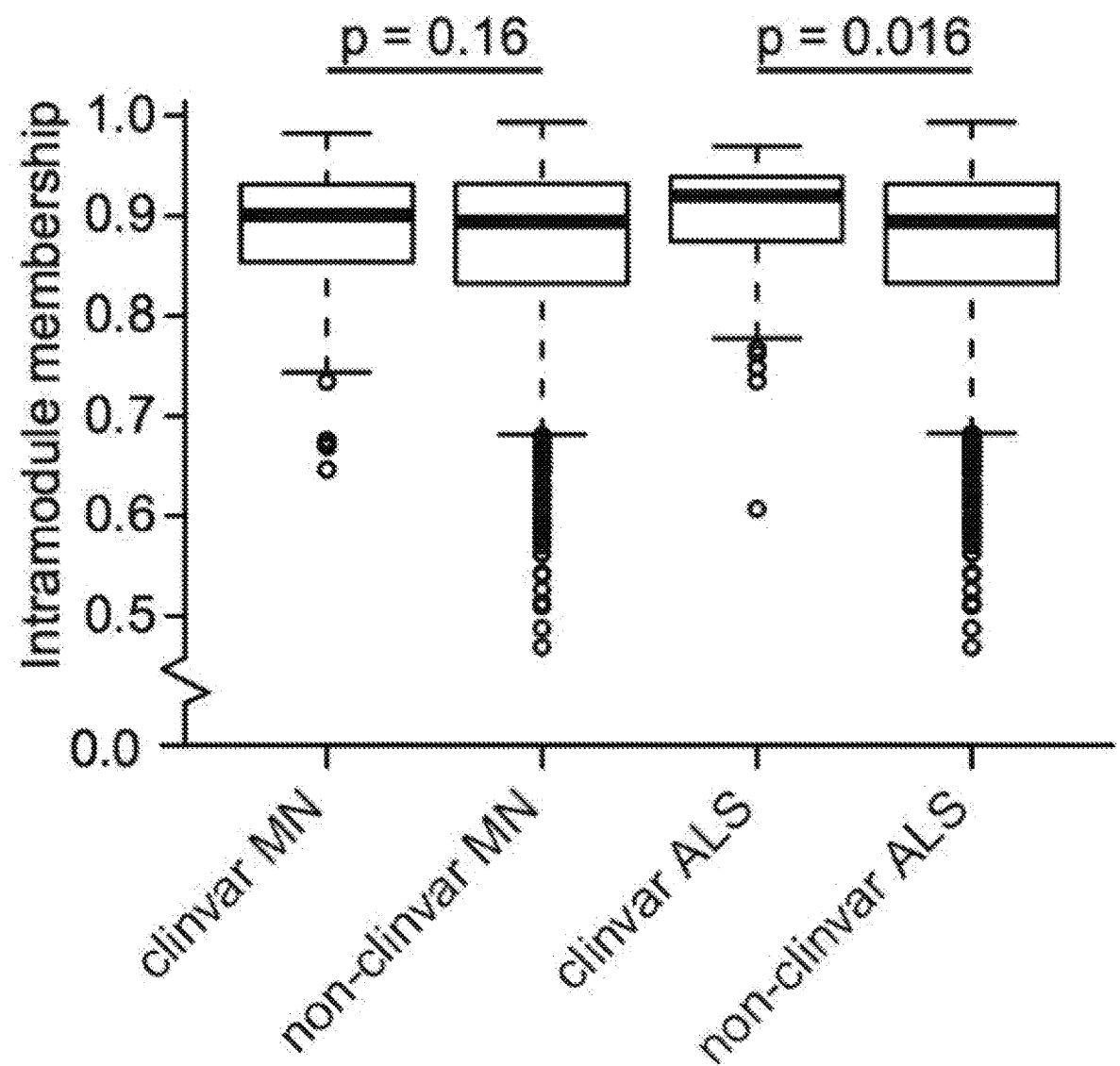
FIG. 13E: Pathogenic ALS genetic variants have higher intramodule membership than genes not affect by variants. Among the 4,711 genes classified into modules, genes were divided by either those affect by pathogenic variants versus unaffected genes for either motor neuron disease (first and second bins, respectively with n=139 and n=4,572) or ALS (third and fourth bins, respectively with n=67 and n=4,644). Significance was tested using the Wilcoxon rank-sum test. For MN, W=339, 949, for ALS, W=182,087, and P-values are indicated above comparisons. The median intramodule membership of MN disease variants is higher than unaffected genes, but not significantly. The ALS variants have a significantly higher intramodule membership than unaffected genes.

Total RNA was isolated from all frozen spinal sections using the RNeasy kit (QIAGEN) with on column DNase digestion. For each fetal spinal cord, equal amounts of total RNA from each section were pooled for expression profiling. For D63, spinal cord was isolated as before and fixed in 4% paraformaldehyde for 48 hours. 25 µm sections were taken using cryostat (Leica) at −20° C. and directly mounted on glass slides (Fisher Scientific). Lumbar tissue section was blocked in PBS containing 5% normal Donkey Serum (Sigma) and 0.25% Triton-X for 1.5 hours. Primary antibody solution containing antimouse SMI32 (Covance) and anti-goat Islet-1 (R&D) were incubated overnight at 4° C. Donkey anti-mouse Alexa-flour 488 and donkey anti-goat 594 secondary antibodies (Life Technologies) were incubate for one hour at room temperature. Samples were mounted in Fluoromount-G (SouthernBiotech) and acquired at 10× using automated stitching on a Leica DM 6000 microscope. RNA from iMNs and ESC-derived MNs were obtained directly from samples reported on by Sareen et al., 2013 and Amoroso et al., 2013, respectively. Prior to expression profiling, all RNA samples were run through RNeasy kit columns with on column DNase digestion to produce similarly sized products as the fetal spinal cord samples. RNA expression profiling was performed on the Affymetrix GeneChip Human Genome U133 Plus 2.0 Arrays at the UCLA microarray core facility. A list of all expression data sets used (either generated by or downloaded) in this study is given in FIG. 11.

Example 3

Expression Data Pre-Processing

Previously published mRNA microarray expression data from human fibroblasts (n=2), embryonic stem cells (ESCs) (n=2), and iPSCs (n=3) were chosen to represent cell types relevant to human somatic cell reprogramming (Chin et al., 2009; Maherali et al., 2008). Chin et al., (2009). Induced pluripotent stem cells and embryonic stem cells are distinguished by gene expression signatures. *Cell stem cell* 5, 111-123. Maherali et al. (2008). A high-efficiency system for the generation and study of human induced pluripotent stem cells. *Cell stem cell* 3, 340-345. To represent mature in vivo whole spinal cord, the Inventors obtained previously published mRNA microarray expression data from adult spinal cords (n=8, age range=23-53 years, median=36.5 years) (Roth et al., 2006) and for mature in vivo spMNs data from laser capture micro-dissected spMNs from familial ALS and control patients (Cox et al. 2010; Kirby et al., 2011). Roth et al., (2006). Gene expression analyses reveal molecular relationships among 20 regions of the human CNS. *Neurogenetics* 7, 67-80. Cox et al., (2010). Mutations in CHMP2B in lower motor neuron predominant amyotrophic lateral sclerosis (ALS). *PloS one* 5, e9872. Kirby et al., (2011). Phosphatase and tensin homologue/protein kinase B pathway linked to motor neuron survival in human superoxide dismutase 1-related amyotrophic lateral sclerosis. *Brain: a journal of neurology* 134, 506-517. Additionally, expression data for spMN and oculomotor neurons from non-ALS patients were included. Brockington et al., (2013). Unravelling the enigma of selective vulnerability in neurodegeneration: motor neurons resistant to degeneration in ALS show distinct gene expression characteristics and decreased susceptibility to excitotoxicity. *Acta neuropathologica* 125, 95-109. These 17 in vivo laser-captured MN specimens came from individuals with an age range from 40 to 80 years (median age, 63 years).

All CEL files considered for use in this study were submitted to ArrayAnalysis.org to inspect RNA and microarray hybridization quality, and samples that failed to meet the recommended standards were removed from further analysis. Affymetrix GeneChip Human Genome U133 Plus 2.0 Array CEL files downloaded from GEO as well as produced in this study were normalized together with Robust Multichip Analysis (rma) using the affy package in Bioconductor R. The accession number for the microarray data produced in this study is GEO: GSE75701. Non-informative probesets were then filtered out using pvac package in R. Filtered probesets were then annotated to their HGNC symbol using the Affymetrix annotation file for the GeneChip Human Genome U133 Plus 2.0 Array Release 35, summarized to the gene level by taking the probeset with the maximum expression value to represent the maximal transcriptional activity associated with that gene, and the resulting gene expression values were quantile normalized on the linear scale using the normalize.quantiles function in the preprocessCore package. The processed Affymetrix Human Genome U133 Plus 2.0 Array expression values for 10605 genes. For Kiskinis et al. 2014 RNAseq data, normalized counts for each sample as they were provided through GEO accession series GSE54409 were compiled into an expression table for 14422 Ensembl identifiers, re-annotated to HGNC symbols based on gene symbols selected through Ensembl BioMart, and summarized to the gene level by taking the transcripts with the maximum expression value to represent the maximal transcriptional activity associated with each gene. This produced the expression table for 13530 genes. Kiskinis et al., (2014). Pathways disrupted in human ALS motor neurons identified through genetic correction of mutant SOD1. *Cell stem cell* 14, 781-795.

For Rabin et al. 2010 Affymetrix Human Exon 1.0 ST Array data, CEL files downloaded from GEO accession series GSE18920 and normalized with Robust Multichip Analysis (rma) using the oligo package in Bioconductor R with the pd.huex.1.0.st.v2 array library. Expression values for transcript clusters were re-annotated to Affymetrix Human Genome U133 Plus 2.0 Array probesets, summarized to the gene level by taking the probeset with the maximum expression value to represent the maximal transcriptional activity associated with that gene, and the resulting gene expression values were quantile normalized on the linear scale using the preprocessCore package. This produced the expression table for 15614 genes. Rabin et al., (2010). Sporadic ALS has compartment-specific aberrant exon splicing and altered cell-matrix adhesion biology. *Human molecular genetics* 19, 313-328.

Example 4

Gene Expression Analysis

Pearson correlations, statistical tests, and multiple testing corrections were performed in R. Unsupervised hierarchical clustering was performed in Cluster 3.0 and heat maps were visualized using Java Treeview. Principal component analysis (PCA) was performed in Cluster 3.0 or R. The signed values for principal component coordinates of samples and gene loadings were reversed as necessary to maintain consistency across analyses. PCA plots, as well a scatter, density, and box plots were visualized in R with the basic R plotting tools. Venn and Chow-Ruskey diagrams were generated using the Vennerable package in R. Gene Set Enrichment Analysis (GSEA) was performed on pre-ranked lists generated using PCA gene loadings with 1000 permutations of the gene sets to generate a null distribution. Gene ontology (GO) enrichment was performed using DAVID, and genes represented on the Affymetrix GeneChip Human Genome U133 Plus 2.0 Array or Affymetrix Human Exon 1.0 ST Array were used as background. Adjusted P-value or FDR q-value thresholds for enriched gene sets and GO terms are indicated for each figure in their respective legends.

Figure 7A:
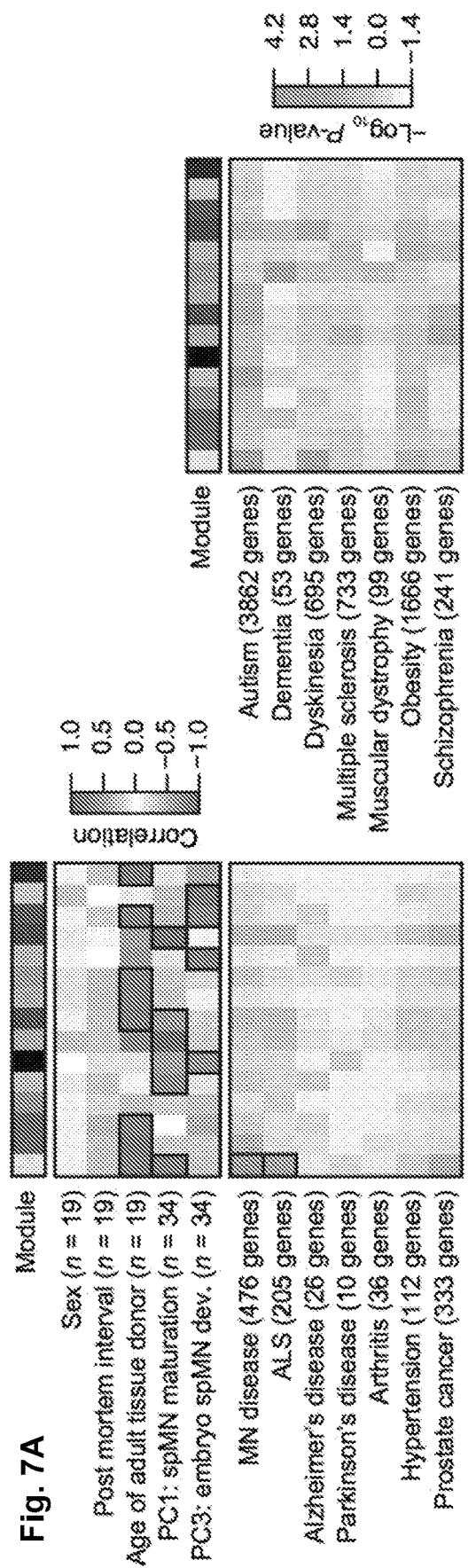
FIG. 7A: Weighted gene co-expression network analysis (WGCNA) clustered 10605 genes across human pluripotent cells, iMNs, fetal spinal tissues, and adult spinal tissues based on similar expression patterns. Six familial ALS spMN samples were left out so that only non-ALS samples contributed to the network building. WGCNA grouped tightly co-expressed genes into 15 modules. Upper and middle panel: Summary expression values for each module, known as module eigengenes, are correlated in a pair-wise manner to external traits of the samples, such as the sex, post mortem interval, or age of adult tissue donor, or correlated to the principal component coordinate of each sample along PC1 and PC3. n=number of samples for which there is data for the indicated sample trait, and thus used in the correlation. Colors on heat map indicate Pearson's pairwise correlation between module eigengene and sample trait. Correlations outlined in black denote values with a Bonferroni-corrected P-value <0.01. Lower panel: Gene variants associated with diseases in the ClinVar database were tested against each of the 15 modules for enrichment. n=number of genes with variants associated with the indicated disease, represented on the human microarray platform, and thus used in the enrichment analysis. The Benjamini-Hochberg corrected negative log 10 P-value from each hypergeometric test is indicated by the green heatmap. Corrected P-values <0.05 are called significant and outlined in black. Gene variants associated with "MN disease" and "Amyotrophic Lateral Sclerosis" are enriched in the yellow module, which significantly correlated with spMN maturation and age, while gene variants associated with other age-related diseases are not significantly enriched in any modules.

WGCNA was performed using its package in R. The two fibroblast samples as well as the HB9::GFP negative sample were removed before network building. Key parameters used for both the Affymetrix GeneChip Human Genome U133 Plus 2.0 Array (iMN) and Human Exon 1.0 ST Array (sALS) expression data sets were as follows: 30 and 21, respectively, were chosen as the soft threshold powers to transform each of the similarity matrices into adjacency matrices, yielding networks with scale-free topology model fits that were greater than 0.8, a value satisfying the proposed scale-free topology criterion. The one step network construction and module detection command blockwiseModules was used, with power=30 or 21, maxBlockSize=10606 (iMN data set) or 15615 (sALS data set), deepSplit=3, pamStage=FALSE, TOMType="signed", networkType="signed", minModuleSize=30, reassignThreshold=0, mergeCutHeight=0, numericLabels=TRUE, pamRespectsDendro=FALSE, saveTOMs=TRUE, saveTOMFileBase="mnTOM", and verbose=3. In the data set excluding the familial ALS spMNs, 10605 genes were used for WGCNA, the soft threshold power was set to 30, and the mergeCutHeight was set to 2.5. This produced the results shown in FIG. 7A. The eigengenes of the resulting modules were then correlated to the samples traits or principal component coordinates, the P-values of each correlation were determined based on the degrees of freedom for each test, (sample size minus 2), and P-values were Bonferroni-corrected based on the number of modules tested (55 for the iMN data set, 52 for the sALS data set, and 15 for the iMN data set lacking familial ALS spMNs). The gene module assignments and correlations to sample traits are described with Bonferroni-corrected P-values <0.01 were called significant and kept for GO term enrichment analysis through DAVID for iMN and sALS.

To identify the 20 key marker genes, fibroblasts were removed from the iMN data set, and PCA was applied to the resulting "training data set" of 10605 genes in 41 samples to produce 41 principal components. The gene loading values for each gene in each principal component were squared and multiplied by the percentage contribution of each principal component. This value is regarded as the weighted gene loading. For each gene, the weighted gene loadings in all principal components, with the exception of PC1, were averaged, and this average was subtracted from the weighted gene loading in PC1. The resulting value is the preferential gene loading for PC1. The preferential gene loading was also calculated for PC3. Genes were partitioned into the gene loading classes PC1neg, PC1pos, PC3neg, and PC3pos based on the signed value of their gene loadings in PC1 or PC3. Scores for preferential gene loading, gene significance, and intramodule membership were calculated by dividing each value by the maximum value within each category. The total gene scores were summed from all three properties and ranked form largest to smallest. The ROCR package was used to calculate and plot the Receiver Operator Characteristics and Area Under the Curve analyses. Predictions were based on correct classification of pluripotent stem cells, fetal-like cells, and adult spinal cord cells. Tests were performed using either 1) the Pearson correlation between the expression values in the test data set and the median expression values among those cell types in the training data set, or 2) the coordinate along PC1 (negative threshold below PC1 coordinate for pluripotent stem cells, positive threshold above PC1 coordinate for adult spinal cord cells, and positive threshold above PC7 coordinate (6640 genes) or PC2 coordinate (20 genes) for fetal-like cells. PC coordinates were generated by performing PCA with 6640 or 20 genes on all samples from both the training and test data sets.

Hypergeometric tests for module enrichment were performed using custom scripts applying the dhyper function in R, and the resulting hypergeometric P-values were corrected with the Benjamini-Hochberg method. For Clinvar enrichment in the iMN modules, 22608 genes represented on the Affymetrix GeneChip Human Genome U133 Plus 2.0 Array were used as the background number of genes. For iMN module enrichment in the sALS modules, 21279 genes represented on both the Affymetrix GeneChip Human Genome U133 Plus 2.0 and Human Exon 1.0 ST Arrays were used as the background number of genes. Cytoscape 3.0 was used to visualize network topology for each of the four classes of human networks depicted in FIGS. 6F-6I. For each class, the 99th percentile of edge weights were filtered followed by filtering for source nodes with at least 30 edges with target nodes. Edge and node attributes, as well as graphical layout constraints are described in the figure legends.

Example 5 iPSC-Derived MNs Resemble Fetal Rather than Adult MNs

Figure 1B:
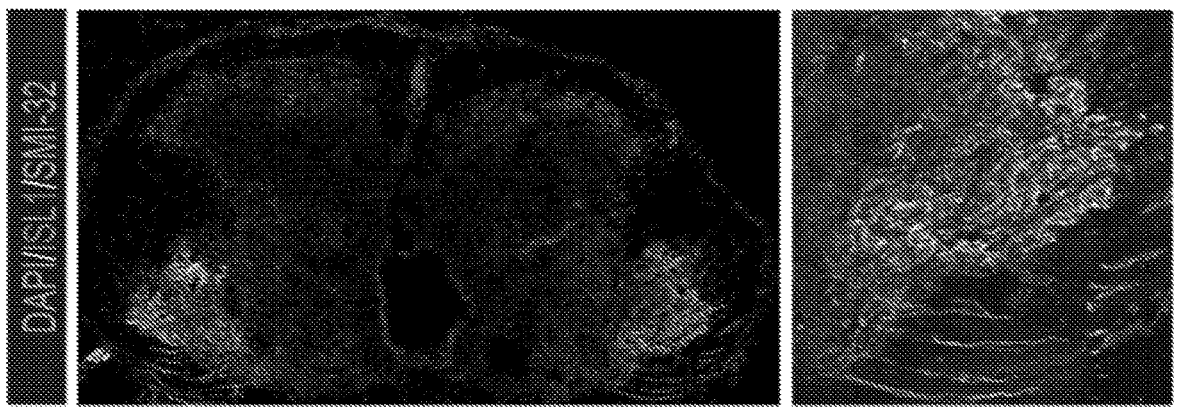
FIG. 1B: Immunofluorescence staining of a 63-day-old fetal spinal cord. Inset depicts ISL1 (red) and SMI-32 (green) positive cells in the motor horn with ventrally projecting processes, indicating the presence of MNs at this developmental stage. Nuclear DAPI stains are shown in blue.
Figure 1C:
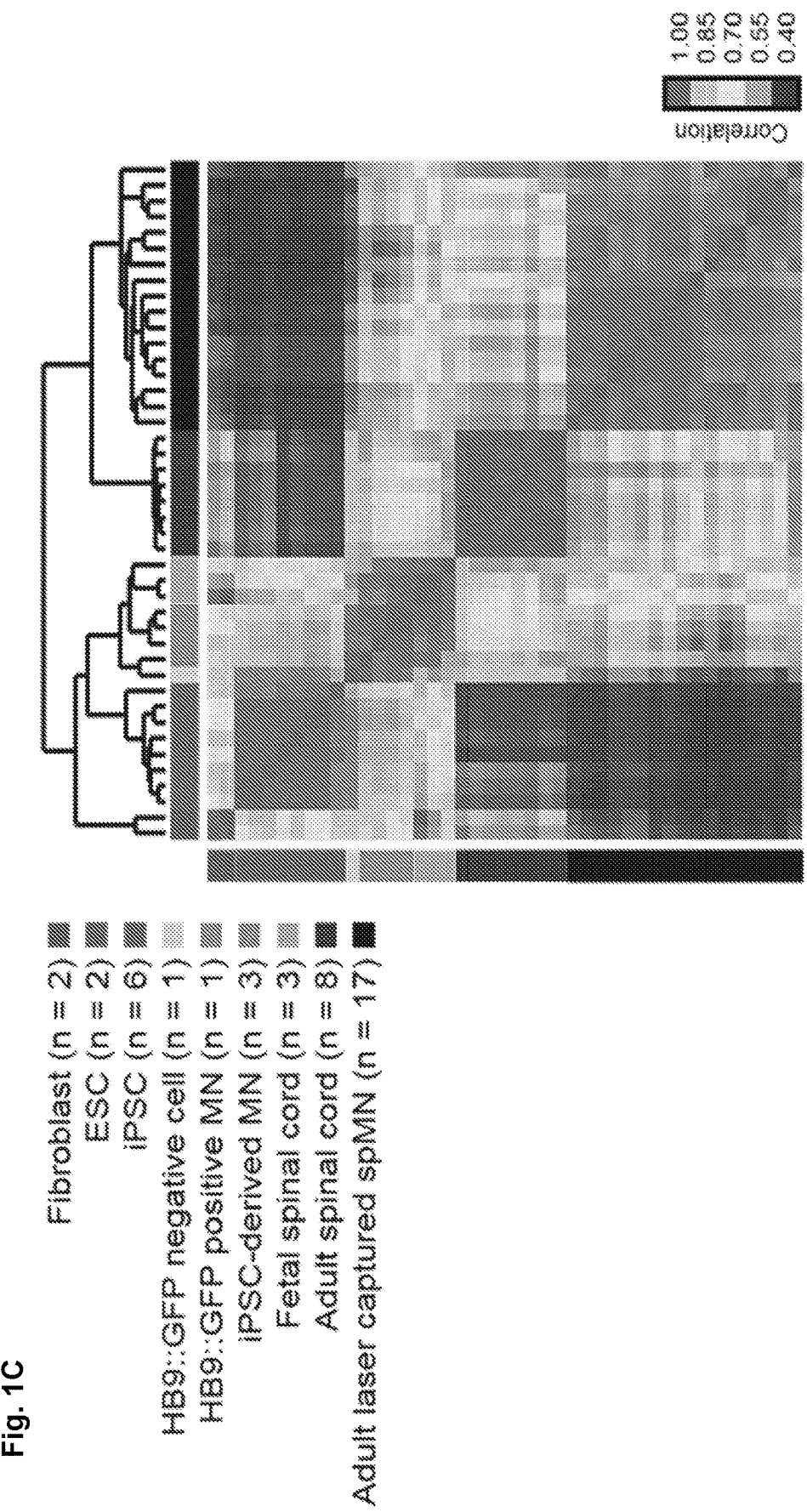
FIG. 1C: Unsupervised hierarchical clustering of mRNA transcripts. Heatmap indicates Pearson's correlation between pairwise sample comparisons and dendrogram indicates average linkage distance between samples. The color legend for sample types refers to FIG. 1D and FIG. 1E as well.
Figure 1D:
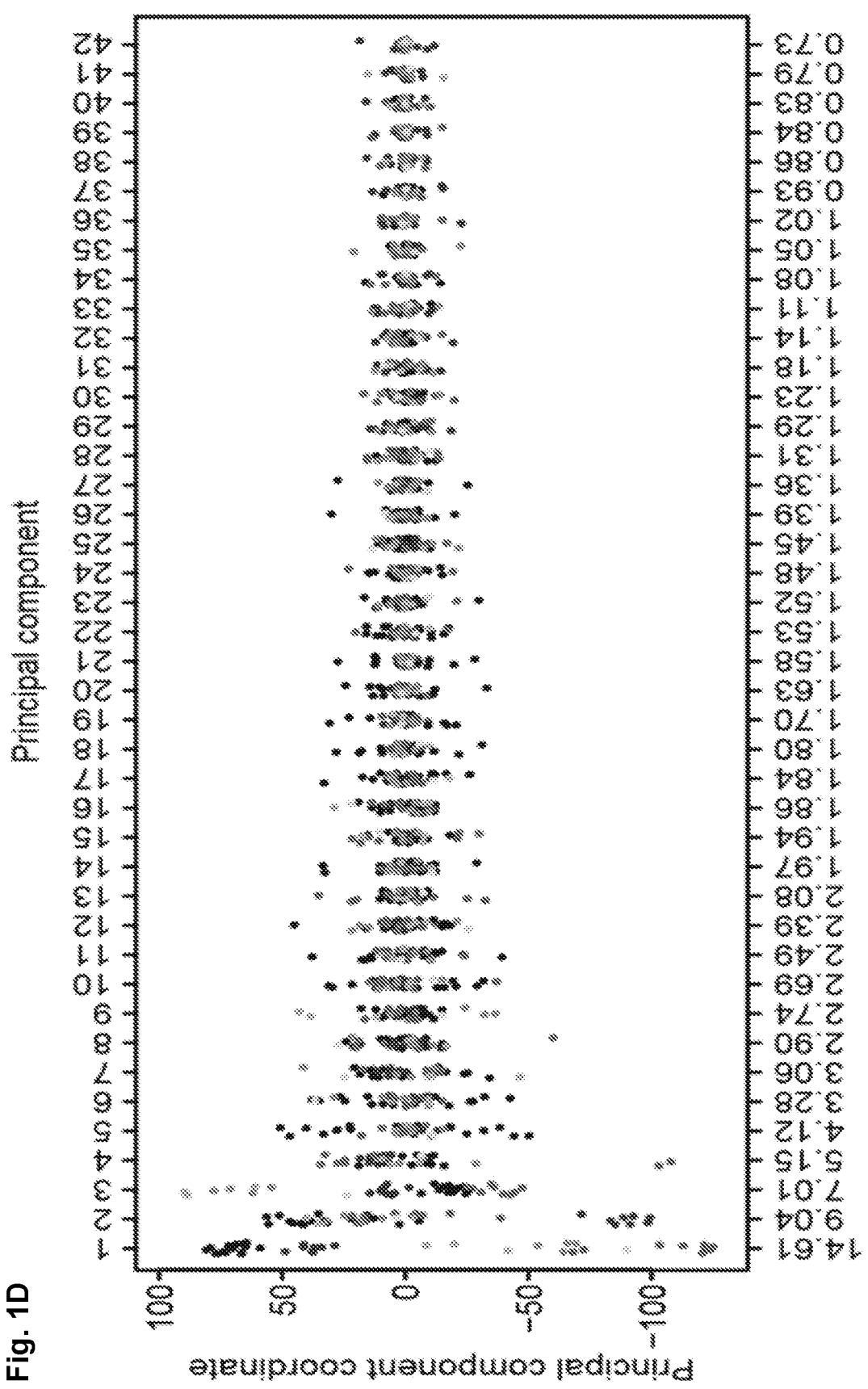
FIG. 1D: Principal component analysis of mRNA transcripts. Y-axis depicts sample coordinate along each principal component. The percent contribution to the total variance of the data by each principal component is shown along the x-axis. In order to reduce obscuration, data points are jittered randomly along the x-axis within each bin. Sample colors refer to FIG. 1C.
Figure 1E:
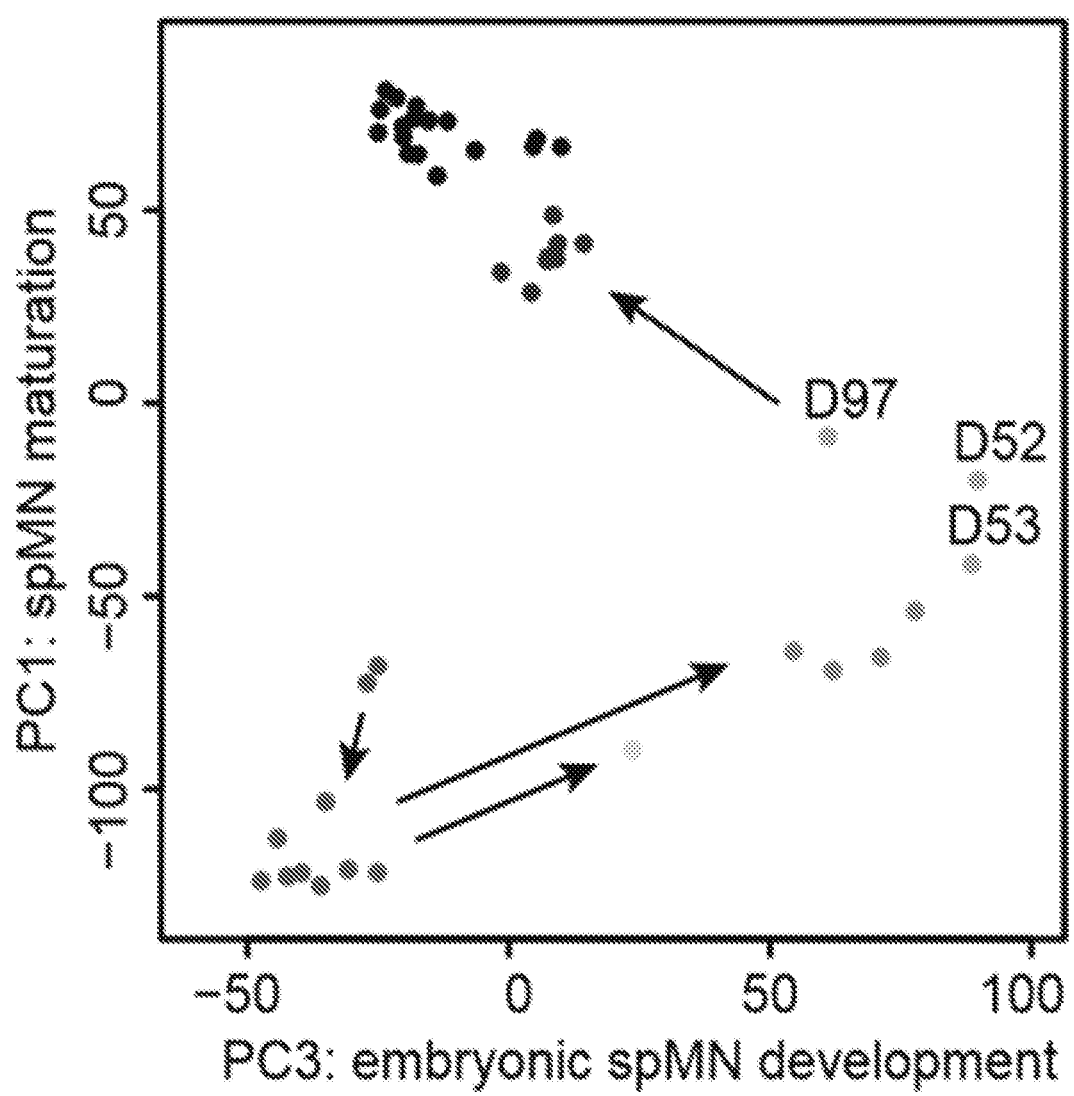
FIG. 1E: Principal components (PC) 1 and 3 are the major features that meaningfully illustrate relationship among all samples that were analyzed. Sample colors refer to FIG. 1C. Arrows depict the progression of fibroblasts (magenta) reprogrammed to iPSCs (red), the subsequent differentiation of iPSCs into either HB9::GFP negative cells (yellow) or HB9::GFP positive MNs (green), which project towards fetal spinal cords (cyan). Arrows also depict the progression of fetal spinal cords towards adult spinal tissues (blue and black). The days post conception of fetal spinal cord donors are indicated next to the cyan data points.
Figure 1F:
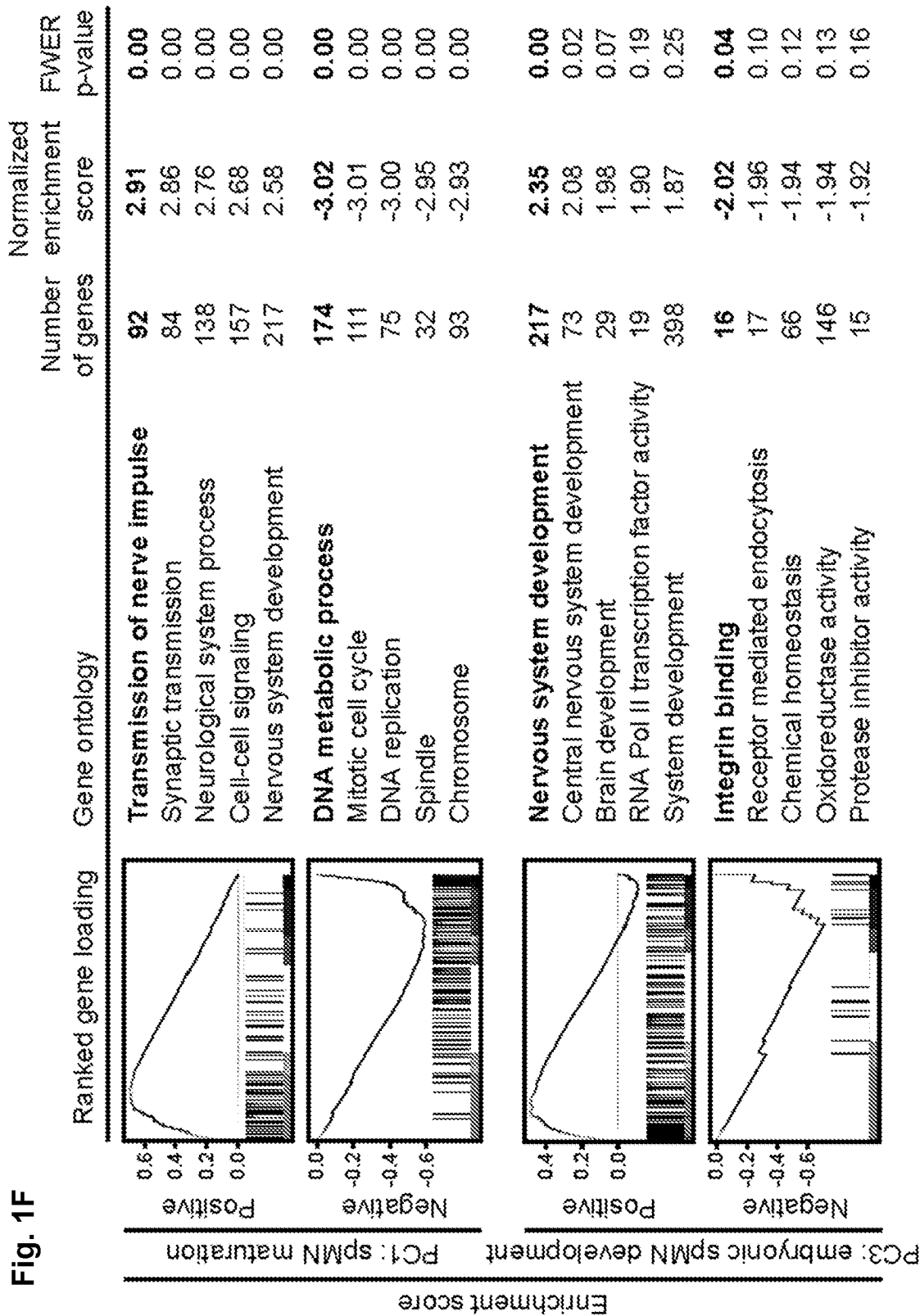
FIG. 1F: Gene set enrichment analysis of ranked gene loadings from PC1 and PC3 for gene ontology (GO) terms. "Positive" and "Negative" categories indicate GO terms enriched among genes whose loadings contribute most to the respective positive or negative direction of each principal component. Enriched GO terms for each category are listed along with family-wise error rate (FWER) corrected P-values. Enrichment plots are shown for bolded GO terms.

The Inventors first compared gene expression profiles in a spectrum of cell types including fibroblasts, iPSCs, fetal spinal cord, whole adult spinal cord and laser captured MNs from the spinal cord of control and ALS patients. The Inventors selectively included expression profiles that use the same microarray platform. This reduced the likelihood of confounding batch effects. iMNs were generated using an established protocol in order to derive 33-45% choline acetyl transferase (ChAT)- and SMI-32-double positive differentiated motor neurons in vitro by seven weeks (FIG. 1A). The Inventors also obtained mRNA expression data for MN cultures from human ESCs containing an HB9::GFP motor neuron reporter, which were sorted into GFP positive and negative fractions. To represent immature in vivo spinal tissue during embryonic development, the Inventors generated microarray expression data from human fetal spinal cords. Histological immunostaining for ISL1 and SMI-32 revealed that motor neurons were present in the ventral horn of these spinal cords (FIG. 1B). After combining, preprocessing, and normalizing the expression data for all of the above samples together (n=43), hierarchical clustering and Pearson correlation analyses revealed that iMNs were globally more similar to fetal rather than adult spinal cord tissue or the parental iPSCs from which they were differentiated (FIG. 1C). Principal component analysis (PCA) revealed that the most prominent feature distinguishing cell types by expression differences was between pluripotent cells and adult spMNs (FIG. 1D, principal component 1). Within this first component, fibroblasts, iMNs, and fetal spinal cords were situated between pluripotent cells and adult spinal tissues. This suggests that the gene expression changes contributing most to this component were associated with the progression from pluripotency through embryogenesis to the adult state. Principal component 2 distinguished non-laser captured adult spinal tissues from all other samples, possibly due to strong gene expression contributed by heterogeneous adult spinal tissue that were absent in the other samples. Notably, principal component 3 distinguished iMNs and fetal spinal cords from all other samples. When considering only principal components 1 and 3 (FIG. 1E), an intuitive progression of MN development can be visualized, where PC1 is best described as spMN maturation, and PC3 is best described as embryonic spMN development. Next, the molecular pathways involved in spMN maturation and embryonic spMN development were examined. Gene set enrichment analysis (GSEA) was performed on the ranked gene loadings for PC1 and PC3 in order to detect classes of genes that concordantly place each sample along spMN maturation and embryonic spMN development, respectively (FIG. 1F). Notably, pathways related to synaptic transmission were enriched among genes that were upregulated during spMN maturation along PC1, consistent with the idea that MN maturation is characterized in part changes in electrophysiology. Conversely, pathways related to cell cycle and DNA repair were enriched among genes that were downregulated during neuronal maturation. Furthermore, pathways related to nervous system development were enriched among genes that increase with embryonic spMN development along PC3. Interestingly, genes associated with integrin binding, which regulate neuronal migration during embryonic development, decrease as cells positively progress along PC3. Together, these data account for differences in global gene expression as well as specific pathways across all samples, further supporting the idea that iMNs are molecularly restricted to a fetal-like state.

Example 6

Figure 2B:
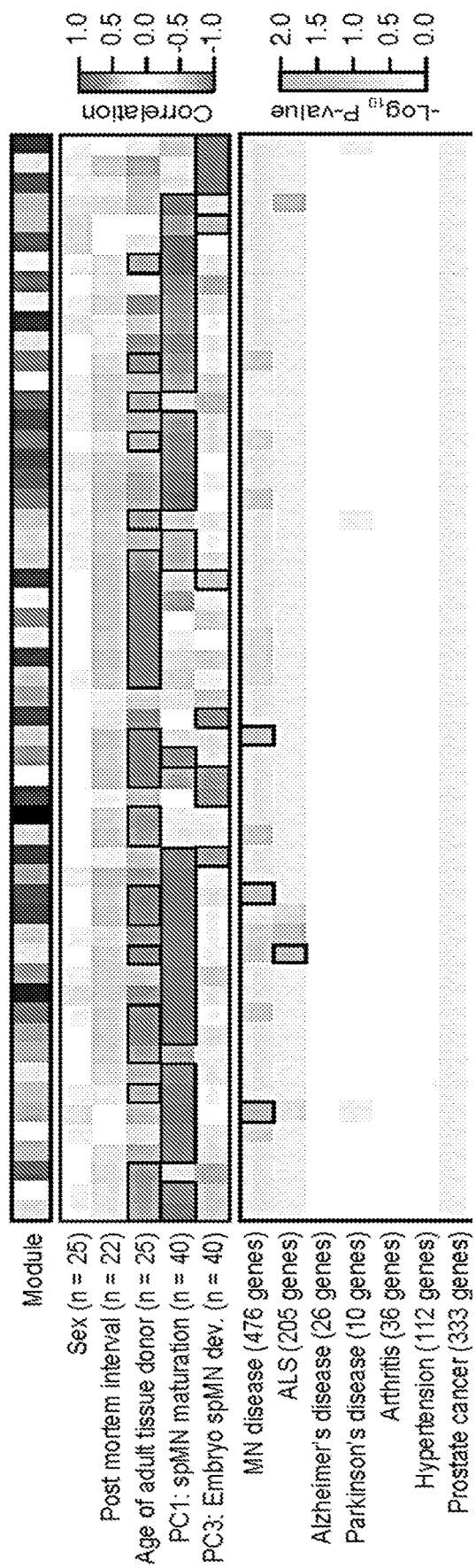
FIG. 2B: Upper and middle panel: Heatmap indicates Pearson's correlation of module eigengenes with external traits of the samples, such as the sex, post mortem interval, or age of adult tissue donor, or correlated to the principal component coordinate of each sample along PC1 and PC3. n=number of samples for which there is data for the indicated sample trait, and thus used in the correlation. Outlined panels indicate correlations with a Bonferroni-corrected P-value <0.01, and these modules were kept for subsequent GO analysis. Lower panel: Gene variants associated with diseases in the ClinVar database were tested against each of the 55 modules for enrichment. n=33 number of genes with variants associated with the indicated disease, represented on the human microarray platform, and thus used in the enrichment analysis. Green heatmap indicates the Benjamini-Hochberg corrected negative log 10 P-value from each hypergeometric test. Corrected P-values<0.05 are called significant and outlined in black.
Figure 2C:
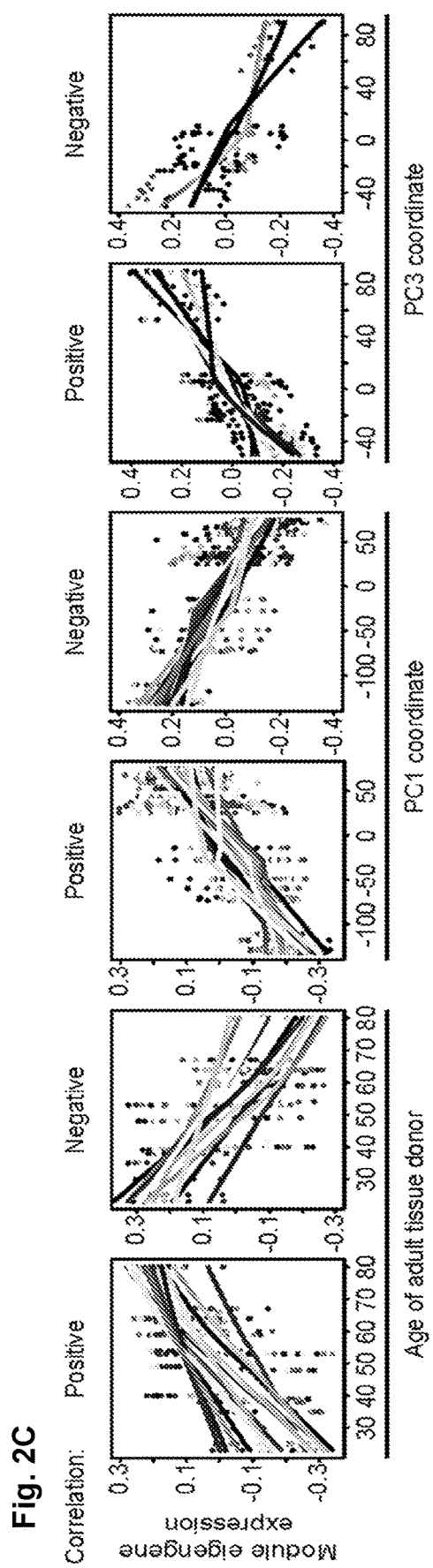
FIG. 2C: For each module eigengene that significantly correlates (Positive) or anti-correlates (Negative) with age, PC1, or PC3 (Bonferroni-corrected P-value <0.01), the module eigengene expression values are graphed in a scatter plot against either sample age or PC coordinate. Locally weighted scatterplot smoothing lines are graphed for each module.

Network Analysis Resolves Expression Modules in Development, Maturation and Aging Gene co-expression network analysis has been demonstrated to be a useful method to link tightly co-expressed gene modules to phenotypic traits. Using weighted gene coexpression network analysis (WGCNA), 10605 genes across all 43 samples were hierarchically clustered based on topological overlap (FIG. 2A). This analysis identified 55 modules ranging in size from 30 to 511 genes with a median size of 66 genes. Altogether, 4711 genes were assigned to modules (FIG. 2A, colored bars) and 5894 genes were not classified into any modules (FIG. 2A, grey bars). When the expression of each module eigengene was correlated against an external trait of a sample, only the age of the spinal tissue donor significantly correlated positively or negatively to a subset of module eigengenes (FIG. 2B, Age of adult tissue donor, outlined panels). In addition to external traits, each sample analyzed by PCA was assigned a coordinate along each principal component. When the expression of each module eigengene was correlated against PC1, the component that describes spMN maturation, or against PC3, the component that describes embryonic spMN development, subsets of module eigengenes were also significantly correlated to each principal component in an independent manner (FIG. 2B, PC1 and PC3, outlined panels). This analysis thus identified gene coexpression networks that are strongly associated with age, spMN maturation, and embryonic spMN development (FIG. 2C).

While neuron maturation and aging are two physiological features believed to play roles in the presentation of ALS and other late onset, neurodegenerative diseases, their distinction has been difficult to define. Interestingly, the correlation analysis revealed that some modules significantly correlated with spMN maturation but not age and vice versa (FIG. 2B, Age of adult tissue donor and PC1, outlined panels). Additionally, some modules correlated with both spMN maturation and age in the same direction, while other modules correlated with both in opposite directions. This analysis was thus able to resolve gene co-expression networks associated with the processes of neuron maturation and aging. spMN maturation and aging are disrupted by genetic variants causing ALS To test if any of the 55 modules identified by WGCNA were associated with age-related diseases, an enrichment analysis was performed using the ClinVar database. Strikingly, pathogenic genetic variants associated with the search terms "motor neuron" were enriched in the dark grey, purple, and light green modules, and those associated with "Amyotrophic Lateral Sclerosis" were enriched in the yellow module (FIG. 2B, MN disease and ALS, outlined panels). Notably, these four modules were significantly correlated with spMN maturation, age, or both (FIG. 2B, Age of adult tissue donor and PC1, outlined panels). Enrichment for MN disease and ALS genetic variants in these modules were specific, as there was no significant enrichment for genetic variants associated with other age-related disease such as Alzheimer's disease, hypertension, or prostate cancer (FIG. 2B, lower panels). Modules identified using WGCNA on a data set where all familial ALS samples were removed yielded similar results (FIG. 7A), suggesting that the age- and spMN maturation correlated modules are indeed modifiers of ALS and MN disease presentation. The Inventors decided to pursue subsequent analyses using modules built with the expression data set that included the familial ALS samples so as to 1) increase the sample size of spMNs, thereby increasing the robustness of the detected modules and 2) provide some representation of co-expression networks as they occur in spMNs from familial ALS patients.

Example 7

Figure 2D:
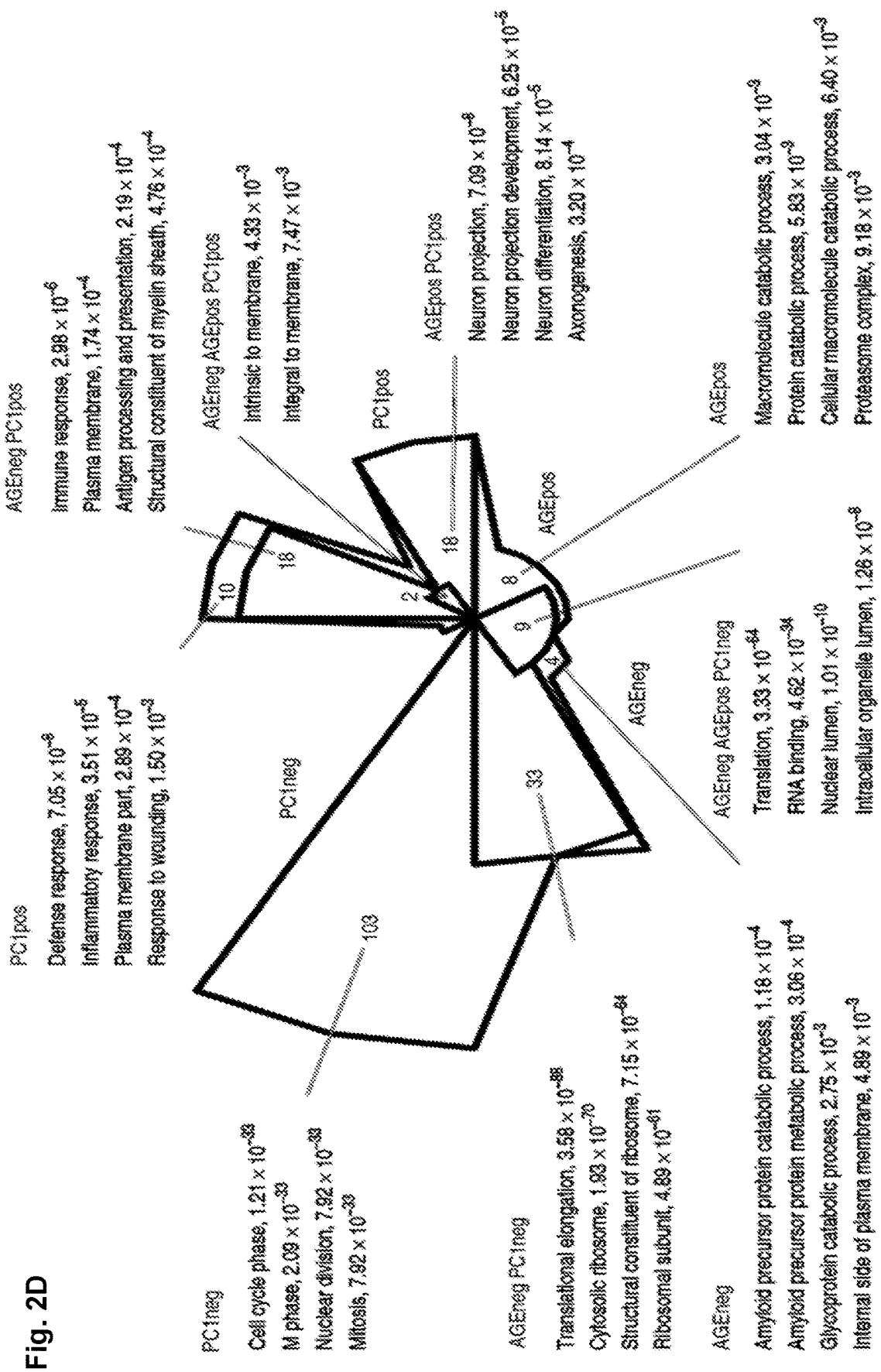
FIG. 2D: Chow-Ruskey diagram illustrating the number of overlapping and distinct GO terms (Bonferroni-corrected p-value <0.05) enriched in modules identified as significantly correlated or anti-correlated to age (AGEpos or AGEneg, respectively) or spMN maturation (PC1pos or PC1neg, respectively). Representative pathways are listed in grey boxes extending from diagram, along with the lowest Bonferroni-corrected p-values across all modules.
Figure 7C:
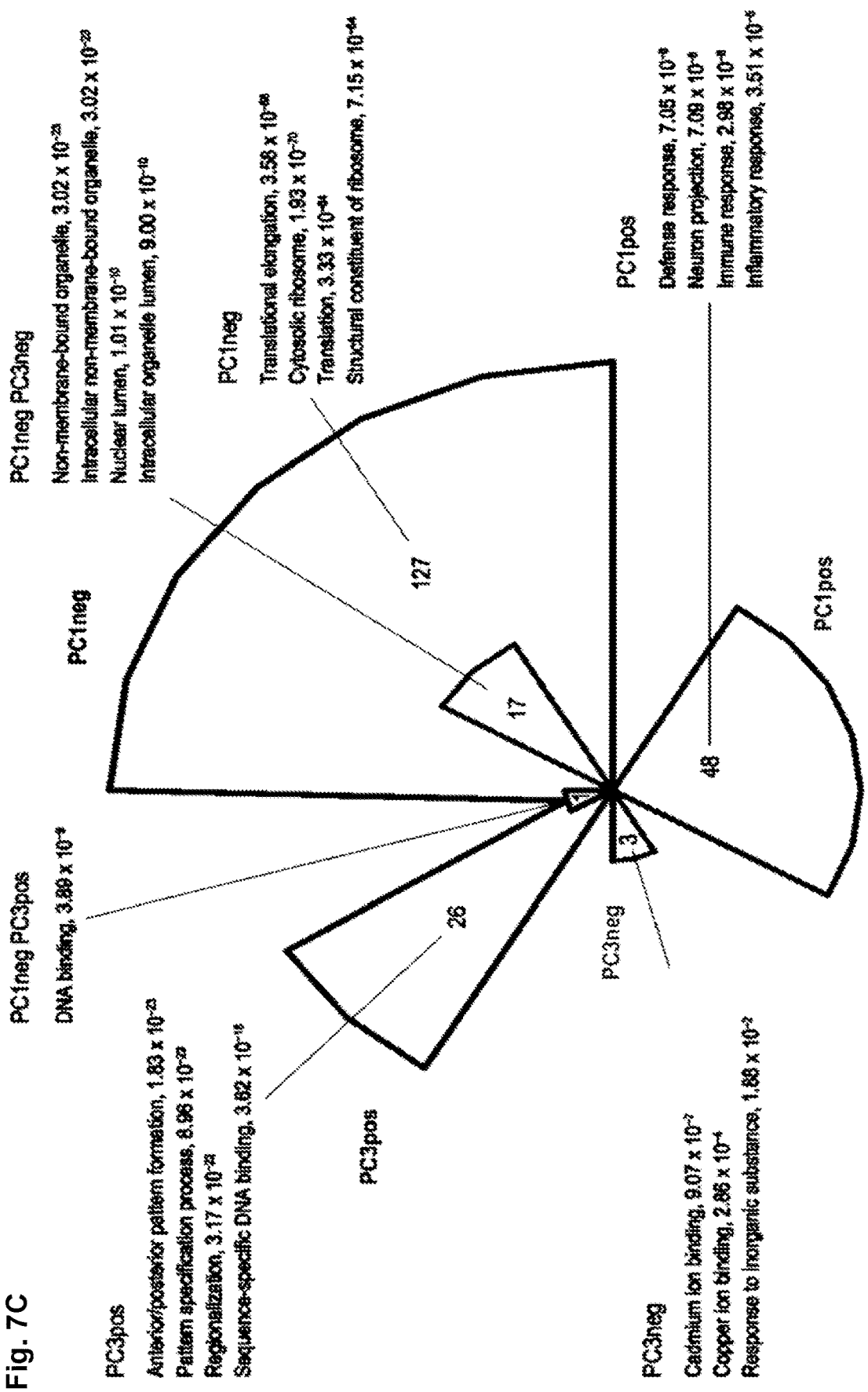
FIG. 7C: As in FIG. 7B, except illustrating the number of overlapping and distinct GO terms in spMN maturation (PC1pos or PC1neg, respectively) or embryonic spMN development (PC3pos or PC3neg, respectively).

Network Enrichment Analysis Resolves Pathways Related to spMN Maturation and Aging To gain a biological understanding of these network-to-sample trait relationships, the age- or spMN maturation-associated modules were tested for enrichment of genes belonging to gene ontology (GO) terms for biological process, molecular function, or cellular compartment. Each of the 55 modules was grouped into four classes: those that significantly correlated with spMN maturation positively (PC1pos) or negatively (PC1neg), and those with age positively (AGEpos) or negatively (AGEneg). Performing a four-way intersection, this analysis revealed the relative number of overlapping and distinct GO terms enriched in each class (FIGS. 2D, 7B, 7C).

Pathways involved in cell cycle and mitosis were exclusively enriched in modules that negatively correlated with PC1 (FIG. 2D), consistent with GSEA results from the ranked PC1 gene loading values (FIG. 1F). Neuron projection modules positively correlated with both PC1 and age, suggesting that axonogenesis is a continual process throughout spMN maturation and aging. Translation and ribosomal pathways were enriched in modules that negatively correlated with both PC1 and age (FIG. 2D), indicating that co-regulated gene networks associated with protein production decline in cells during spMN maturation as well as aging. Conversely, proteasome-associated genes increased with age, suggesting an increasing role for protein degradation and catabolism in older cells. Notably, amyloid precursor processing genes were enriched in modules that negatively correlated with age, indicating a progressively declining ability to prevent glycoprotein aggregates in older cells. Interestingly, immune response and myelin sheath genes were enriched in modules that positively correlated with PC1, but negatively correlated with age (FIG. 2D), suggesting that these gene networks increase in expression during spMN maturation, but decrease in expression during aging. Altogether, these pathway enrichment analyses of gene networks effectively resolve biological processes that are associated with spMN maturation, aging, or both traits.

Example 8

Principal Component and Network Analyses Reveal 20 Key spMN Maturation and Embryonic Development Markers Having identified gene expression networks that significantly associated with the processes of spMN maturation and embryonic spMN development, the Inventors investigated if the properties of genes within those networks could identify key markers of both processes. A reduced list of key markers would enable a robust comparison among samples that were expression profiled on different microarray platforms and provide a robust indicator of the embryonic developmental and maturation status of pluripotent cell-derived MN cultures. To achieve this reduced list, the Inventors scored each of the 10605 genes along three properties with respect to principal components 1 and 3 that reflect spMN maturation and embryonic spMN development, respectively (FIG. 1E). These three properties were 1) preferential gene loading, 2) gene significance, and 3) intramodule gene membership. The preferential gene loading was defined as the net contribution of each gene to one particular principal component and minimal contribution to all other principal components.

After generating gene scores for each of these three properties, genes were partitioned into four classes: PC1pos, PC1neg, PC3pos, and PC3neg, based on the signed value of their gene loadings in PC1 or PC3. Once partitioned, gene scores for each property were weighted to a maximum score of one, and a total gene score was summed from all three properties and ranked from largest to smallest. From each of these four ranked lists, five genes were selected based on the best gene scores, as well as selected for diverse representation of module colors and prior knowledge of biological relevance to spMN maturation or embryonic spMN development. Together, this totaled 20 genes that best predicted the sample clustering along the axes of PC1 and PC3. Plotting the gene loadings for these 20 genes along PC1 and PC3 with respect to the other 10585 genes illustrated the preferential gene contribution, significance, and module color variety to each component (FIG. 3A).

Figure 3B:
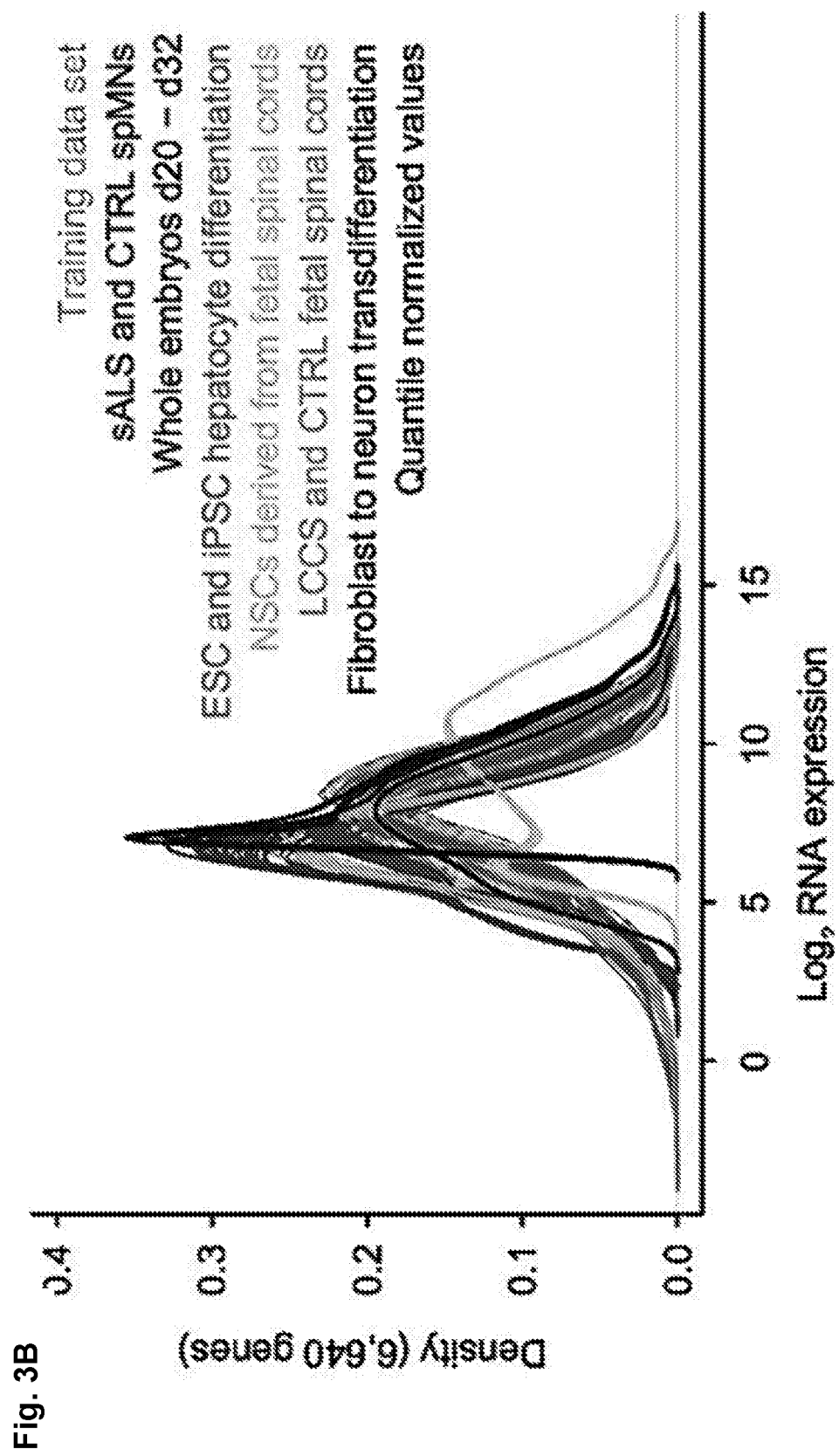
FIG. 3B: Gene expression density plot for 6640 genes represented in the training data set as well as in the validation data sets. Each line represents the gene expression distribution from one sample. Colors denote the study from which they were obtained. Black line represents the quantile normalized distribution of all samples.
Figure 3C:
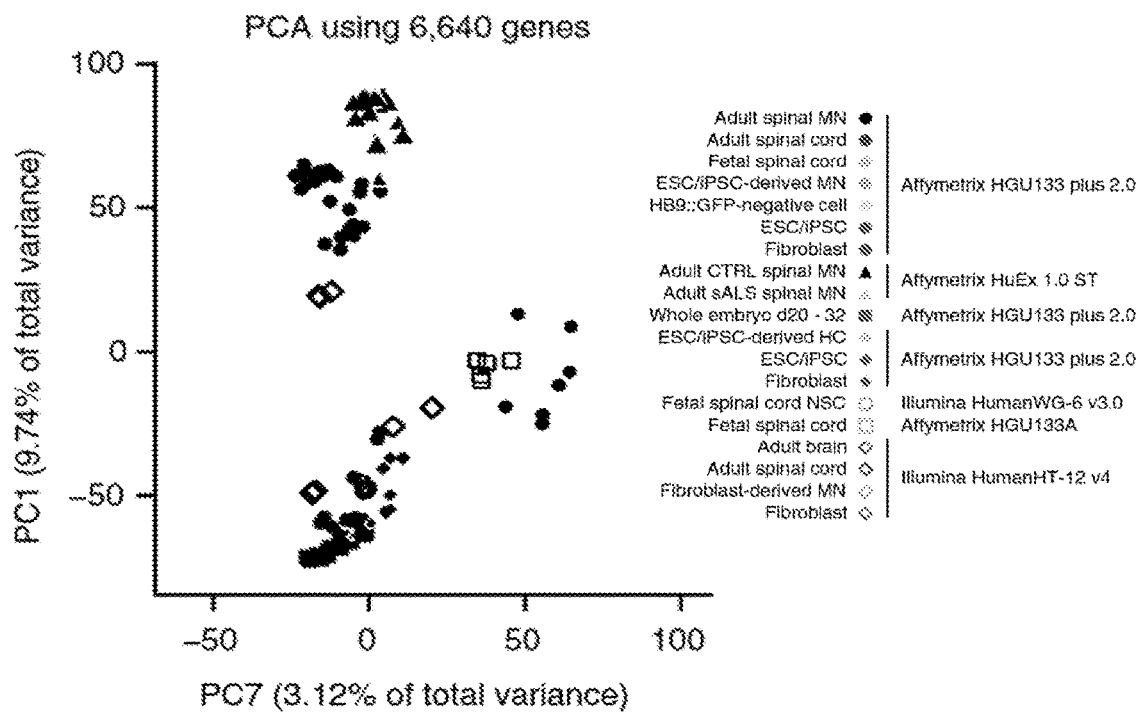
FIG. 3C: Principal component analysis performed on 6640 quantile normalized gene expression values across 120 samples represented in FIG. 3B. Samples plotted by their coordinates along PC1 and PC7. Sample legend is shown on the far right. Colors of data points indicate similar sample types, and shapes of data points indicate the study from which the data were obtained. Microarray platforms are also indicated.
Figure 3D:
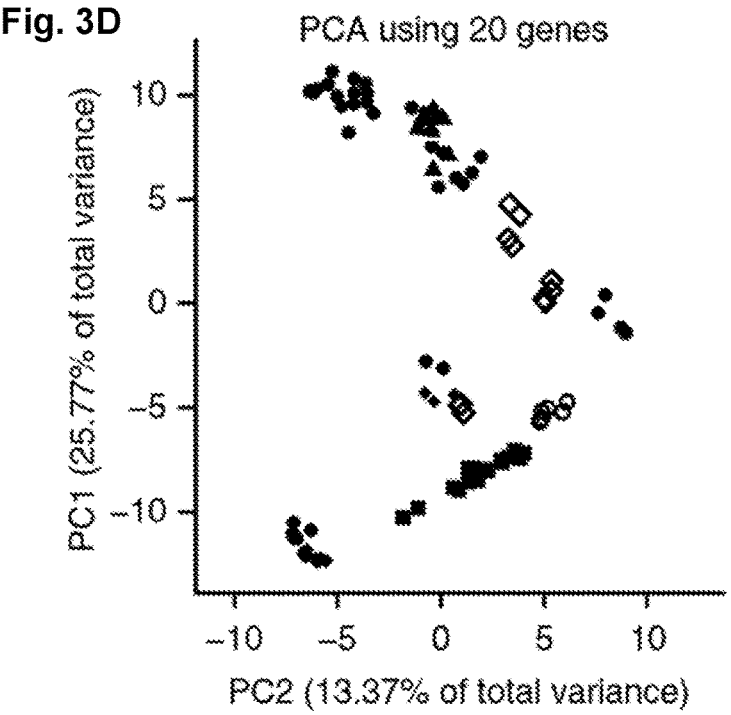
FIG. 3D: As in FIG. 3C, except PCA was performed using 20 genes depicted in FIG. 3A. Samples plotted by their coordinates along PC1 and PC2. Sample legend is shown on the far right.
Figure 3E:
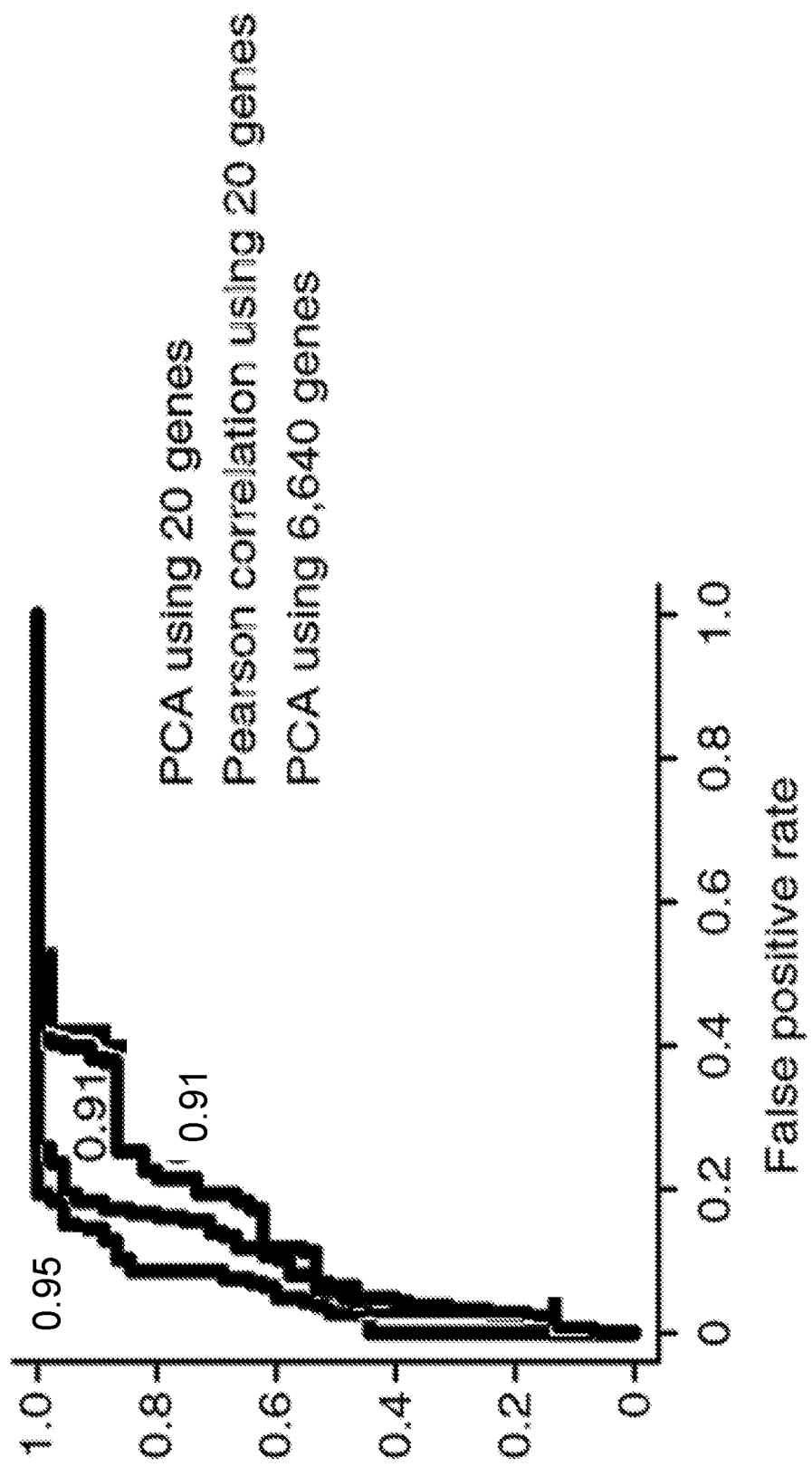
FIG. 3E: ROC analysis performed on three methods classifying samples in the validation data set as pluripotent stem cells, fetal-like cells, or adult spinal cord cells. Classifications were based on sample correlation to the median expression values of target cell types in the training data set (red) or based on sample coordinates along the spMN maturation or embryonic development principal components generated from 6640 genes (black) or 20 genes (blue). The area under the curve (AUC) is shown next to each like-colored curve, and summarizes the overall performance of each classification method.
Figure 8A:
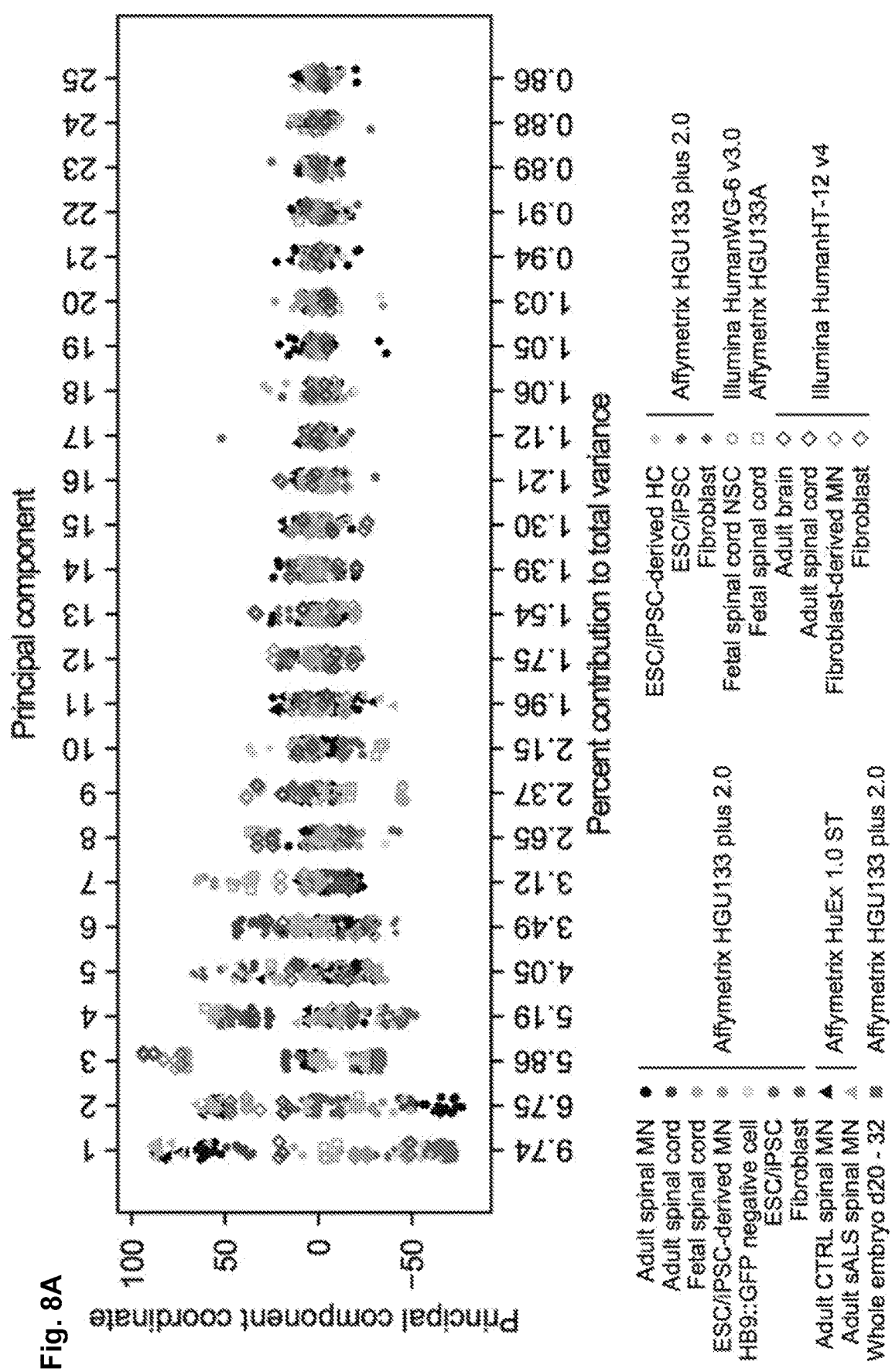
FIG. 8A: Principal component analysis of mRNA transcripts from training and validation samples illustrates the major features that define the samples with respect to one another. The y-axis depicts the coordinate along each principal component for each sample. The percent contribution to the total variance of the data by each principal component is shown along the x-axis. In order to reduce obscuration, data points are jittered randomly along the x-axis within each bin. Sample legend is shown on the far right. Colors of data points indicate general sample type, and shapes of data points indicate the study from which the data were obtained. Microarray platforms are also indicated.

To test the robustness of this panel of genes to assay spMN maturation and embryonic spMN development, gene expression data were downloaded from additional published studies as validation data sets that utilized a variety of five distinct microarray platforms. Expectedly, gene expression values produced from different microarray platforms, as well as from different studies, exhibited varied distribution patterns (FIG. 3B, colored curves). To minimize these differences across microarray platforms and studies while preserving gene expression relationships within samples, gene expression distributions were quantile normalized to conform all values to a single distribution pattern (FIG. 3B, black curve). Performing PCA on all 6640 quantile normalized genes produced principal components that resembled the spMN maturation and embryonic spMN development components similar to the training data set (FIGS. 1E, 3C and 8A). Specifically, PC1 again best described spMN maturation and PC7 in this instance best described embryonic spMN development. Notably, PC3 captures variation due to differences between Illumina and Affymetrix microarray platforms, despite efforts to minimize these differences using quantile normalization (FIGS. 3B and 8A). Strikingly, PCA performed using the 20 key genes reflected spMN maturation in PC1 and embryonic spMN development in PC2 (FIG. 3D). Importantly, variations arising from differences between microarray platforms were not noticeably captured. A receiver operating characteristic (ROC) analysis tested the ability to sensitively and accurately classify samples from the validation data set. The ratio of true to false positive classifications of pluripotent stem cells, fetal-like cells, and adult spinal cord cells using the 20 genes outperformed the same analysis using 6640 genes as well as routinely used Pearson correlations with all 6640 genes, yielding a higher area under the curve (AUC) score (FIGS. 3E and 8B-8D). These observations support the efficacy and universal adaptability of combining PCA and WGCNA to identify key markers of spMN maturation and embryonic spMN development.

Example 9

Gene Expression Networks are Distinctively Affected by Familial ALS in spMNs and iMNs The expression of modules associated with age, spMN maturation, and embryonic spMN development were next investigated in spMN and iMN samples comparing a familial form of ALS (fALS) cause by mutant SOD1 (mtSOD1) to controls (FIG. 4) (Kirby et al., 2011; Kiskinis et al., 2014). mtSOD1 significantly affected several module classes. Most notably, modules correlated or anti-correlated to age were respectively downregulated or upregulated by mtSOD1 in spMNs (FIG. 4A). These age-associated modules in mtSOD1 spMNs were dysregulated in the opposite manner in which they are endogenously expressed during human aging. This suggests that the aging process enacts homeostatic gene expression programs that may protect spMNs, which otherwise undergo cell death due to misexpression of these transcriptional programs in the mtSOD1 condition. Interestingly, all of the embryonic spMN development-associated modules were significantly upregulate in mtSOD1 spMNs (FIG. 4C), indicating that some embryonic pathways are also disrupted in mtSOD1-induced ALS.

Mapping the expression of these trait-associated modules in an independent data set for mtSOD1 and control iMNs (Kiskinis et al., 2014) revealed a pattern that was distinct from spMNs. When comparing module expression levels between mtSOD1 and control iMNs, the modules correlated to age were significantly downregulated (FIG. 4D). However, modules anti-correlated to age were not significantly upregulated. These results suggest that age-associated gene expression networks affected by mtSOD1 ALS in spMNs may be recapitulated to some extent in iMNs. Yet, the expression of modules correlated to spMN maturation was not significantly different in iMNs (FIGS. 4B and 4E). These observations thus suggest that iMNs do not faithfully recapitulate the expression profile of mature spMNs affected by mtSOD1. Lastly, modules correlated or anti-correlated to embryonic spMN development were respectively upregulated or downregulated in iMNs (FIG. 1F). Thus, the expression pattern of these embryonic spMN development-associated modules in an independent expression data set supports the idea that iMNs are more similar to fetal spinal tissue than adult spMNs.

Example 10 spMN Maturation and Age Modules are Dysregulated in Sporadic ALS

Figure 5A:
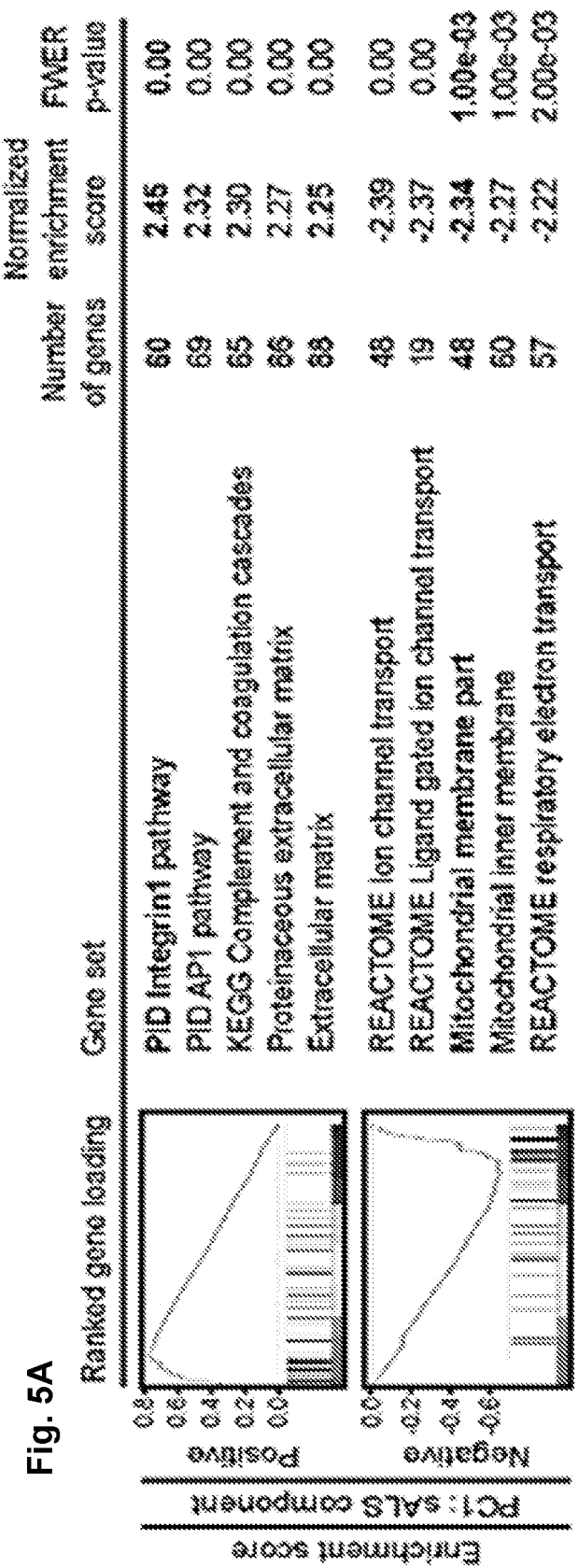
FIG. 5A: Gene set enrichment analysis of ranked gene loadings from PC1 for pathways and GO terms. "Positive" and "Negative" categories indicate gene sets enriched among genes whose loadings contribute most to the respective positive or negative direction of the sALS component. Enriched gene sets for each category are listed along with familywise error rate (FWER) corrected P-values. Enrichment plots are shown for bolded gene sets.
Figure 9A:
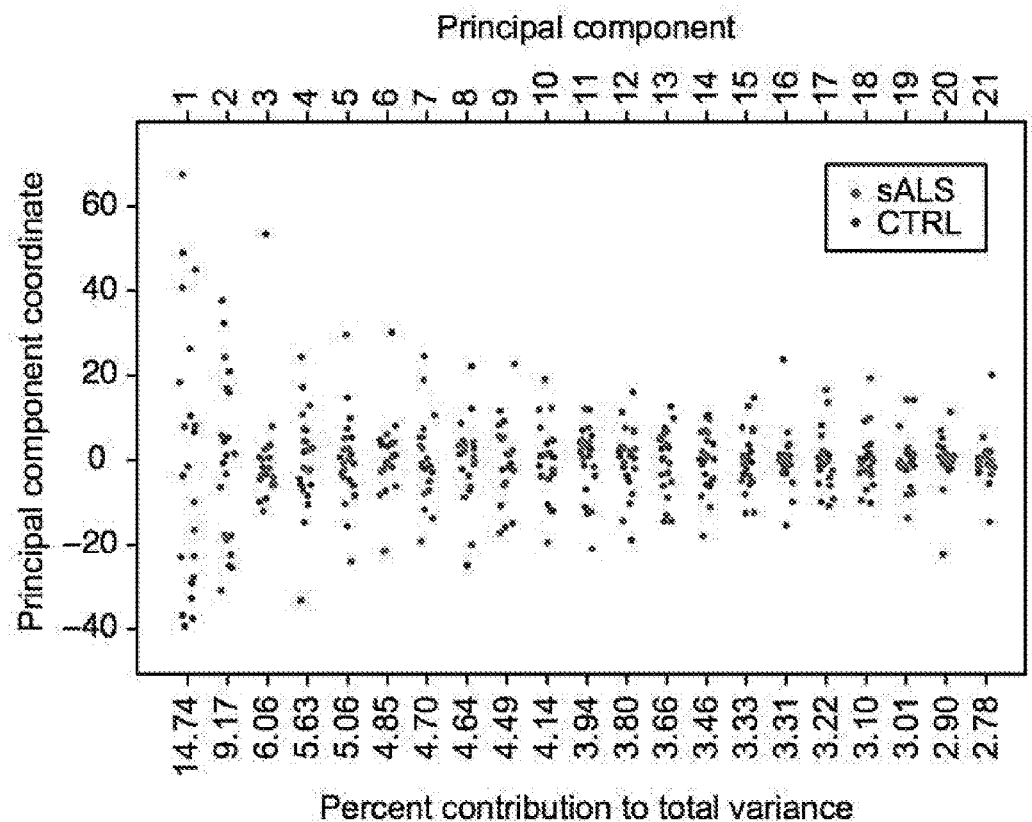
FIG. 9A: Principal component analysis of mRNA transcripts from sALS and control spMN samples illustrates the major features that define the samples with respect to one another. The y-axis depicts the coordinate along each principal component for each sample. The percent contribution to the total variance of the data by each principal component is shown along the x-axis. In order to reduce obscuration, data points are jittered randomly along the x-axis within each bin.
Figure 9B:
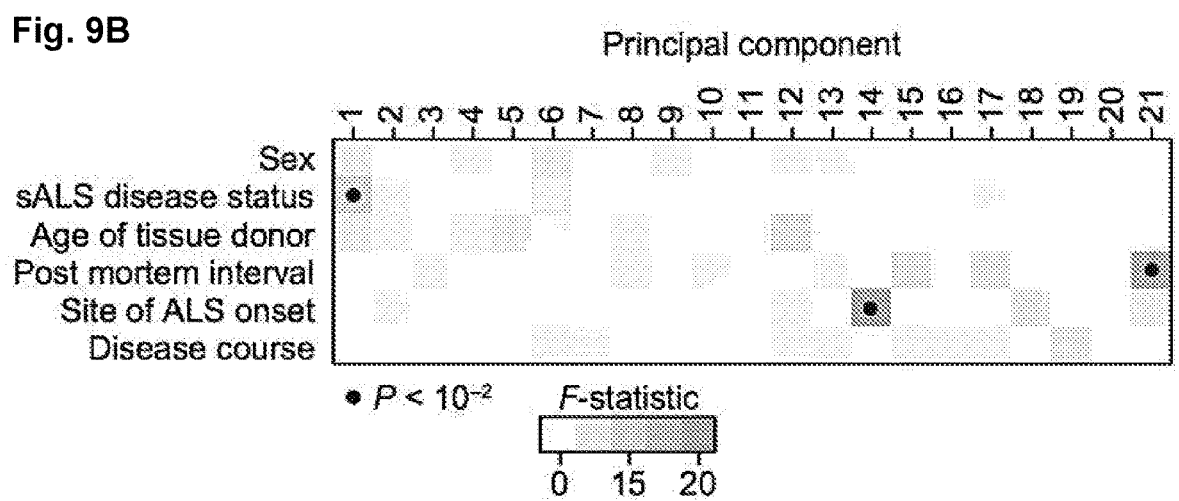
FIG. 9B: Pearson correlation for traits and all principal component coordinates. Correlation co-efficient is indicated for each comparison, and red and blue hues reflect these correlative or anti-correlative values, respectively. NA=not applicable, as the continuous variables of site of ALS onset and Disease course apply only to sALS samples. Correlating these traits to sALS disease status, where sALS samples were coded as 1 and control samples were coded as 0, results in a standard deviation of 0.
Figure 9D:
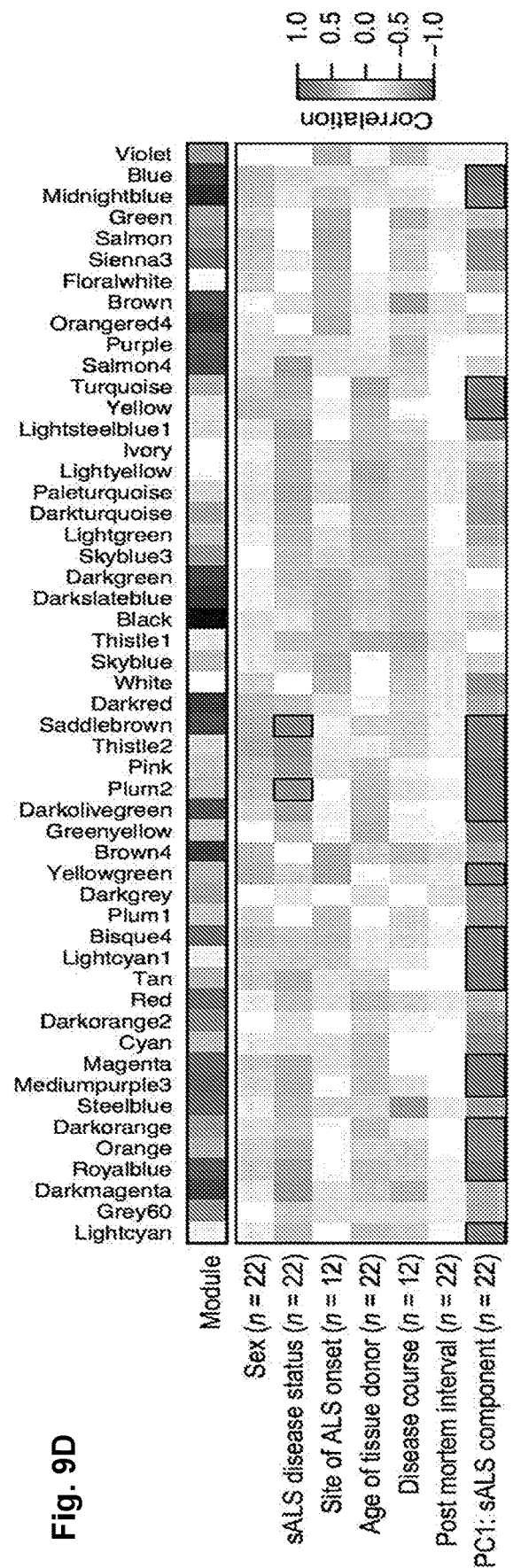
FIG. 9D: Summary expression values for each module, known as module eigengenes, are correlated in a pair-wise manner to external traits of the samples, such as the sex, sALS disease status, site of ALS onset, age of tissue donor, disease course, or post mortem interval, or correlated to the principal component coordinate of each sample along PC1 (the sALS component). n=number of samples for which there is data for the indicated sample trait, and thus used in the correlation. Colors on heat map indicate Pearson's pairwise correlation between module eigengene and sample trait. For PC1, correlations outlined in black denote values with a Bonferroni-corrected P-value <0.01, and these modules were kept for subsequent GO analysis. For sALS disease status, Benjamini-Hochberg-corrected P-values <0.05 are outlined in black. Some modules uniquely correlate or anti-correlate with a sample trait, while others correlate to more than one sample trait.

WGCNA with the composite data set analyzed thus far (hereinafter referred to as the iMN expression data set) did not identify modules significantly correlated to ALS conditions (data not shown). This was likely due to an insufficiently large representation of samples associated with familial ALS in the data set, perhaps also compounded by distinct expression changes induced by the two forms of familial ALS represented: mtSOD1 and mtCHMP2B. Thus, a separate analysis was performed to identify gene networks that significantly associate with the ALS condition in spMNs. An independent transcriptomic data set of 15614 genes that specifically focused on comparing gene expression between sporadic ALS (sALS) and control spMNs (Rabin et al., 2010) was analyzed (n=22, age range=47-81 years, median=73 years). This data set, also used in the gene reduction validation analysis described above (FIG. 3B), similarly compared the transcriptional profiles of laser capture micro-dissected spMNs between 12 sALS patients and 10 control subjects. PCA performed on this expression data set (hereinafter referred to as the sALS expression data set) revealed that PC1 best segregated sALS from control spMNs (FIGS. 9A and 9B), therefore this principal component was best described as the sALS component. GSEA was performed on the ranked gene loadings for this component to explore pathways and gene ontologies enriched among genes that were dysregulated in sALS spMNs (FIG. 5A). Interestingly, pathways related to extracellular matrix were enriched among genes that were upregulated in sALS, consistent with previously described gene expression changes found in this data set (Rabin et al., 2010). Conversely, pathways related to mitochondrial ion and electron transport were enriched among genes that were downregulated in the sALS. These observations were not previously described for this data set (Rabin et al., 2010), highlighting the sensitivity of GSEA using PCA gene loadings to detect enriched pathways without thresholding on an arbitrarily assigned, fold change cut-off. Next, gene co-expression networks were built using only expression data from the sALS expression data set. WGCNA on this data set identified 52 modules ranging in size from 31 to 401 genes with a median size of 51 genes. Altogether 4444 genes were assigned to modules (FIG. 9C, colored bars) and 11170 genes were not classified into any modules (FIG. 9C, grey bars). Each module eigengene was then correlated against sex, sALS disease status, site of ALS onset, age of tissue donor, disease course, and post mortem interval. Additionally, each module eigengene was correlated against the sALS component. Among these sample traits, only sALS disease status and the sALS component significantly correlated or anti-correlated to a subset of modules (FIG. 9D, outlined panels).

Figure 5B:
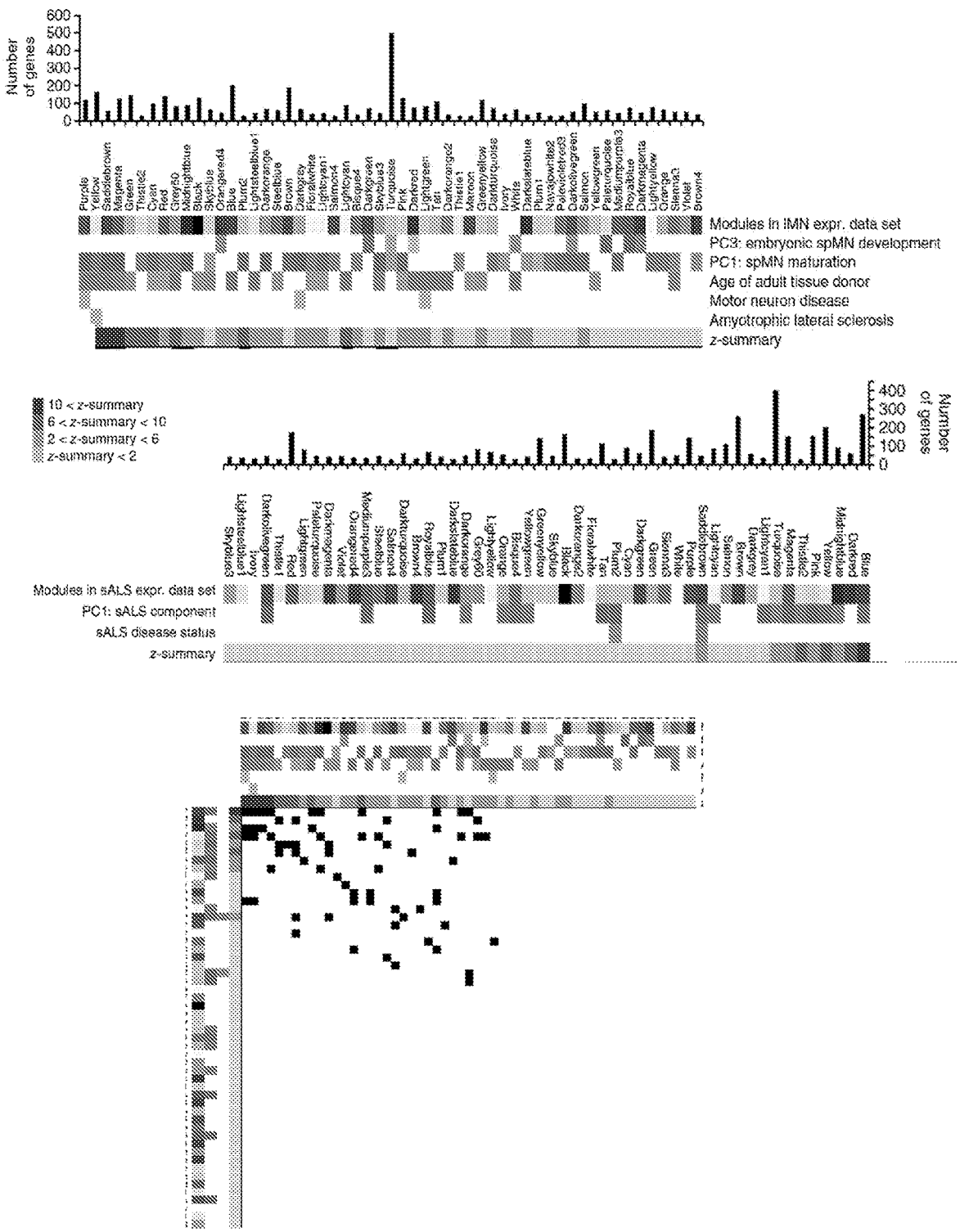
FIG. 5B: For each of the 52 sALS modules, a hypergeometric test was performed to detect enrichment for genes from each of the 55 iMN modules. Upper panel: iMN modules are displayed along with the sample traits with which they are significantly correlated or anticorrelated, as identified in FIG. 2B. Bar graphs above indicate the number of genes assigned to each iMN module that were also represented by probe sets on the Affymetrix Human Exon 1.0 ST Array. Left panel: sALS modules are displayed along with the sample traits with which they are significantly correlated or anti-correlated, as identified in FIG. 9D. Bar graphs to the left indicate the number of genes assigned to each sALS module that were also represented by probe sets on the Affymetrix GeneChip Human Genome U133 Plus 2.0 Array. A matrix of P-values from hypergeometric tests performed for each iMN and sALS module overlap were corrected by the Benjamini-Hochberg method, and subsequent P-values <0.05 are marked as a black square panels and illustrated in the matrix diagram.

Given this observation, the possibility that these gene modules were also involved with spMN maturation and age was hypothesized. Therefore, the extent of overlap were examined between modules defined in the iMN and sALS expression data sets, hereinafter referred to as iMN and sALS modules, respectively. To this end, each sALS module was systematically tested for enrichment of each iMN module (FIG. 5B). This analysis demonstrated that some iMN modules significantly overlapped with one or more sALS modules, and vice versa, indicating that similar module networks were defined in both expression data sets.

Despite an imperfect one-to-one module correspondence, overlapping iMN and sALS modules tended to significantly correlate or anti-correlate to sample traits in a consistent way. For instance, iMN modules that significantly correlated with age and spMN maturation tended to have strong overlap with sALS modules that significantly anti-correlated to the sALS component.

Figure 10A:
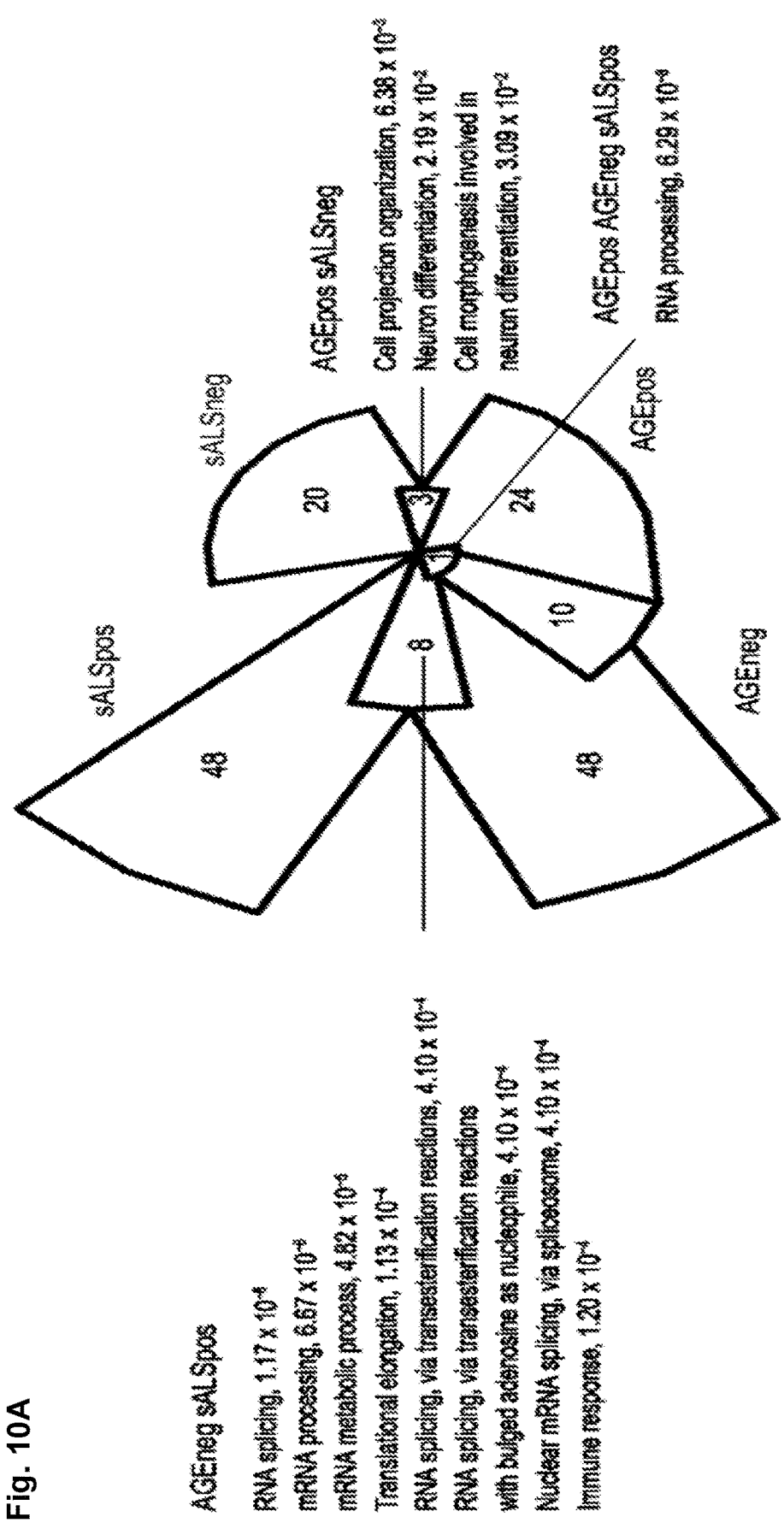
FIG. 10A: age (AGEpos or AGEneg)
Figure 10B:
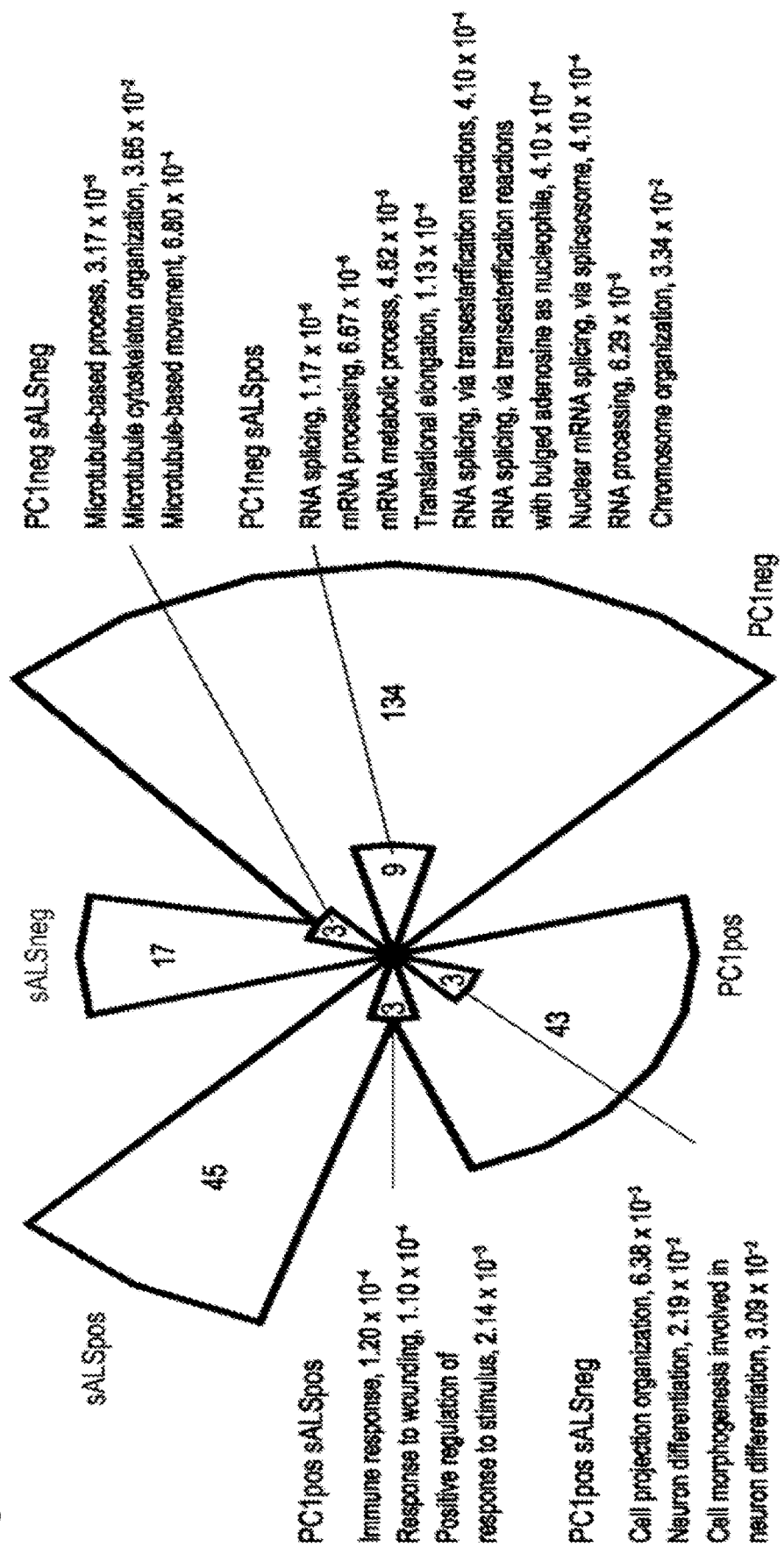
FIG. 10B: spMN maturation (PC1pos or PC1neg), or FIG. 10C embryonic spMN development (PC3pos or PC3neg). Pathways are listed in grey boxes extending from the diagrams, along with Bonferroni-corrected P-values of enrichment in sALS modules.
Figure 10C:
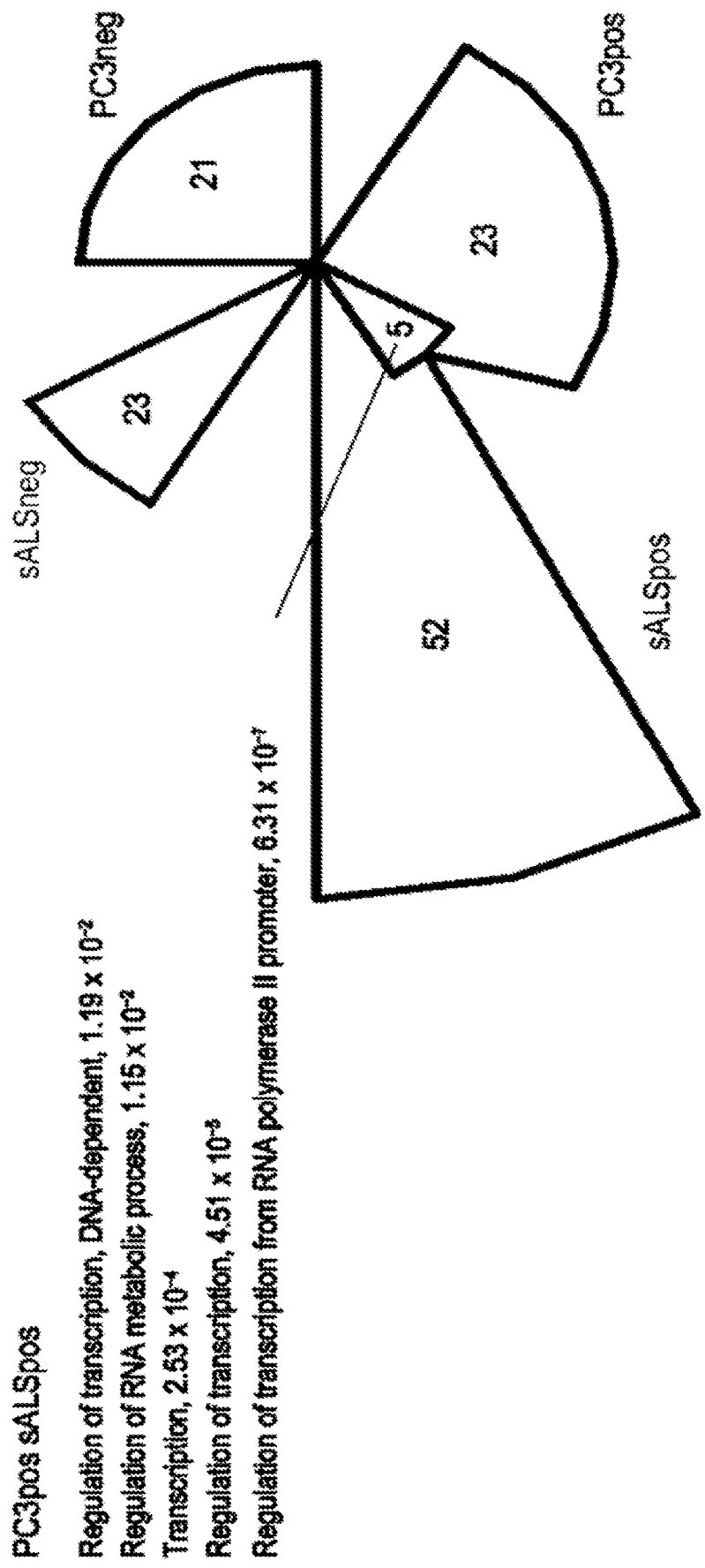
FIG. 10. Gene co-expression network modules in spMNs associated with sALS enrich for similar pathways as spMN maturation and age modules (Related to FIG. 5) Chow-Ruskey diagrams illustrating the number of overlapping and distinct GO terms enriched in modules identified as significantly correlated or anti-correlated with the sALS component (sALSpos or sALSneg, respectively)

Conversely, iMN modules that significantly anti-correlated with age and spMN maturation tended to have strong overlap with sALS modules that significantly correlated to the sALS component. Additionally, three of the four modules that enriched for genetic variants associated with MN disease or ALS significantly overlapped with at least one sALS module that in turn significantly associated with the sALS component or sALS disease status. These observations thus support the idea that gene networks involved in spMN maturation and age are also affected in sALS. To gain a biological understanding of these module-to-trait relationships, enrichment analysis was performed on each significantly associated module for GO terms. Modules were then classified into two groups: those that significantly correlated with the sALS component positively (sALSpos) or negatively (sALSneg). Performing a four-way intersection analysis with either AGEpos and AGEneg, PC1pos and PC1neg, or PC3pos and PC3neg (FIGS. 2D, 7B, and 7C), these analyses revealed the number of overlapping and distinct GO terms enriched in each of the different groups (FIG. 10). Interestingly, pathways such as RNA processing and translational elongation, which are enriched within modules that decline with age and spMN maturation, are also enriched within modules whose expression increases along the sALS component (FIGS. 10A and 10B). Notably, the immune response pathway, which is enriched within modules that increase with spMN maturation and decrease with age, is also enriched in modules whose expression increases along the sALS component (FIGS. 10A and 10B). Conversely, pathways such as neuron differentiation and cell projection, which are enriched within modules that increase with age and spMN maturation, are also enriched within modules whose expression decreases along the sALS component (FIGS. 10A and 10B). To a lesser extent, some transcriptional pathways, which are enriched within modules that increase during embryonic spMN development, are also enriched within modules whose expression increases in sALS (FIG. 10C).

Example 11

Genes Associated with spMN Maturation, Aging, and sALS Tend to be Hub Genes

Figure 6A:
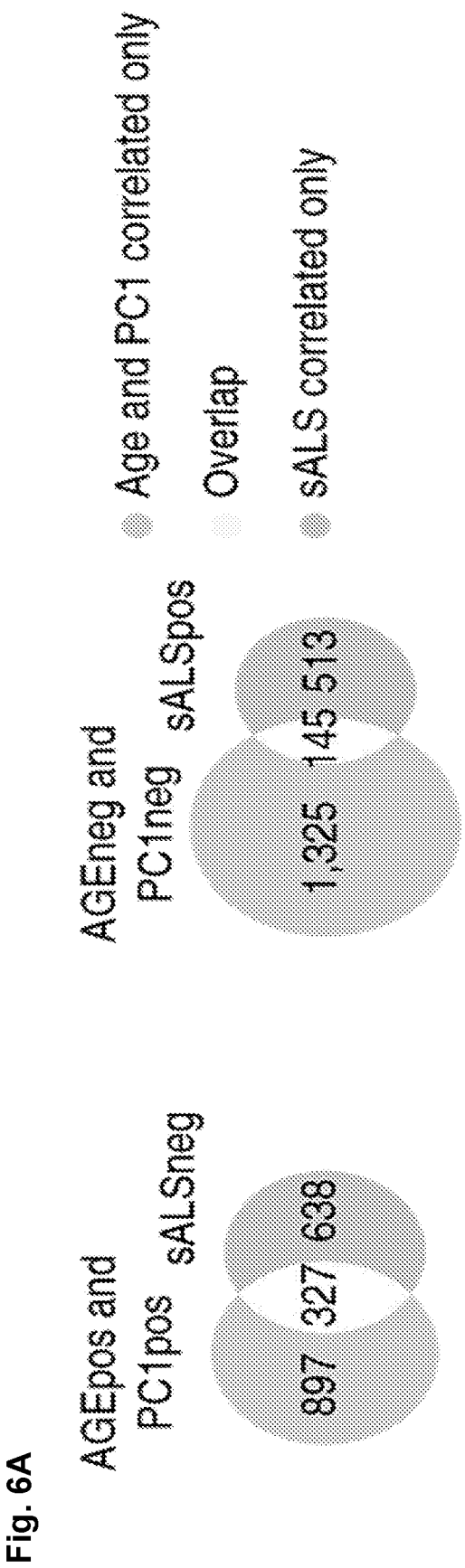
FIG. 6A: Overlap analysis of genes that are represented in WGCNA modules independently built in either the iMN expression data set or in the sALS expression data set.

An alternative approach was taken to explore the network properties of genes affected by maturation, aging, and ALS. Four module classes were defined: modules that 1) increased or 2) decreased expression with maturation and aging (Age and PC1 positive or negative, respectively), modules that 3) increase or 4) decrease with sALS (sALS positive or negative, respectively). Consistent with overlap comparisons performed on a module-by-module basis (FIG. 5B), this comparison of combined modules demonstrates that age and spMN maturation modules had extensive overlap with sALS modules in opposite directions (FIG. 6A). Having identified which genes within the module classes are commonly affected (hereinafter referred to as overlaps), the gene expression networks in both the iMN and sALS expression data sets were observed for any properties that distinguished overlaps from genes that were specifically found in either of the module classes (hereinafter referred to as nonoverlaps).

Figure 6F:
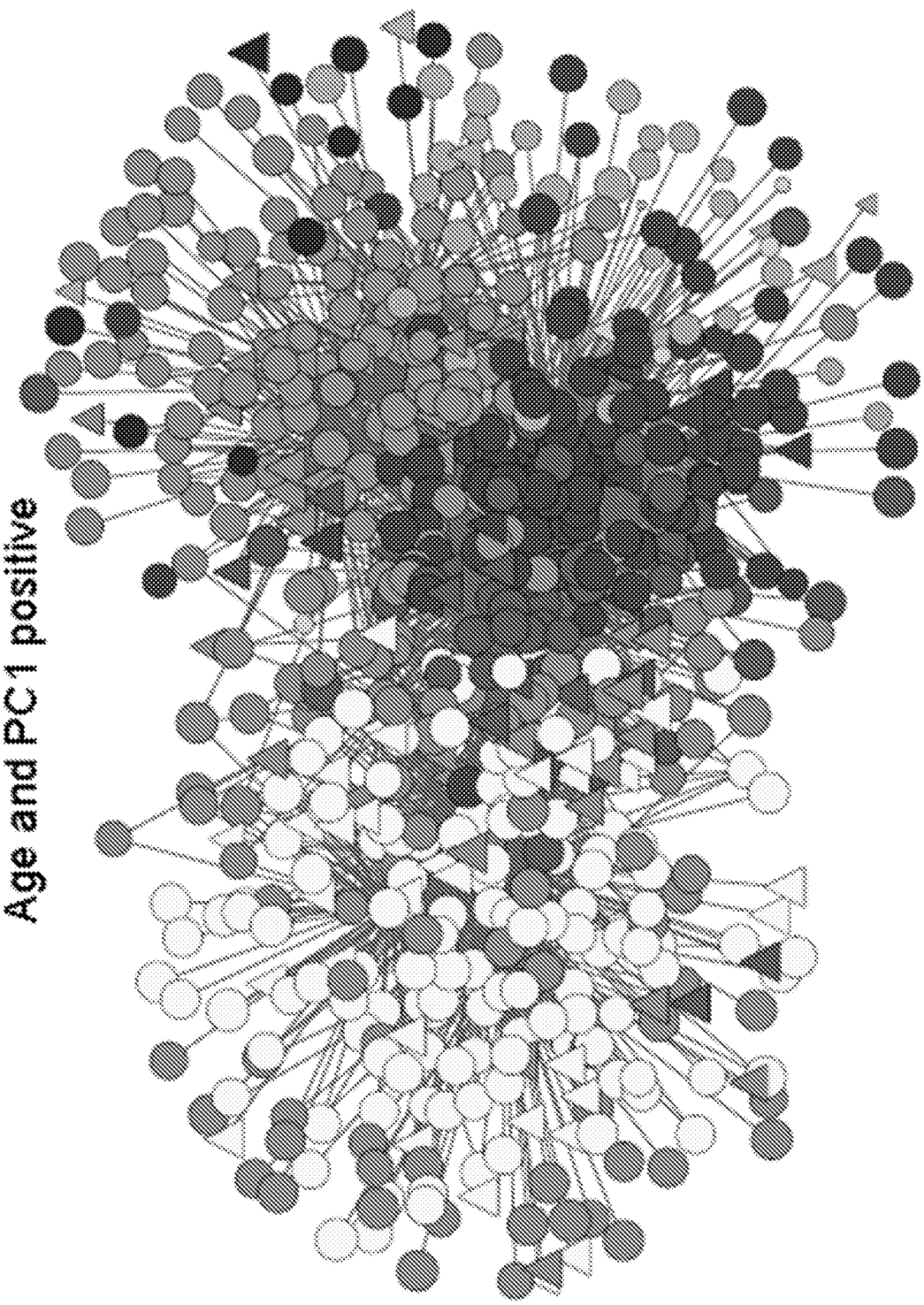
FIG. 6F: Cytoscape network maps for iMN gene modules significantly correlated to age and spMN maturation (PC1) in the iMN expression data set. Node colors indicate module assignments. Circular nodes represent genes correlated with age and spMN maturation in the iMN expression data set, and also anti-correlated with the sALS component in the sALS expression data set. Triangular nodes represent genes detected in the iMN modules that correlate with age and spMN maturation, but are not detected in sALS modules that anti-correlate with the sALS component. The relative sizes of all nodes reflect their gene significance towards age in the iMN expression data set. The $99^{th}$ percentile of edge weights were filtered for display and plotted using the prefuse force layout method.
Figure 6G:
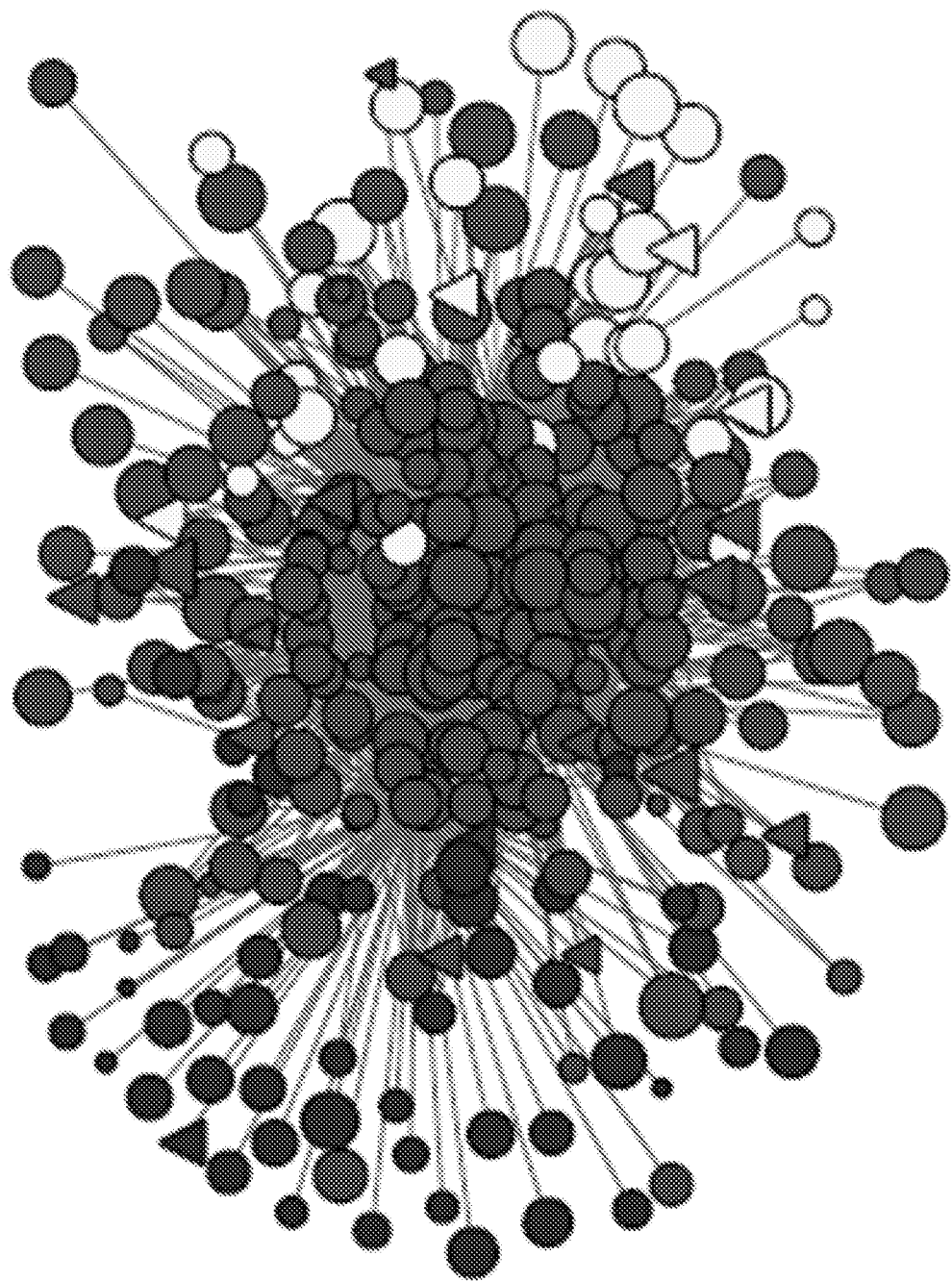
FIG. 6G: As in FIG. 6F, except for sALS gene modules significantly anti-correlated to the sALS component in the sALS expression data set. Larger nodes in this instance have gene significance values closer to −1 and are therefore more anti-correlated to the sALS component.
Figure 6H:
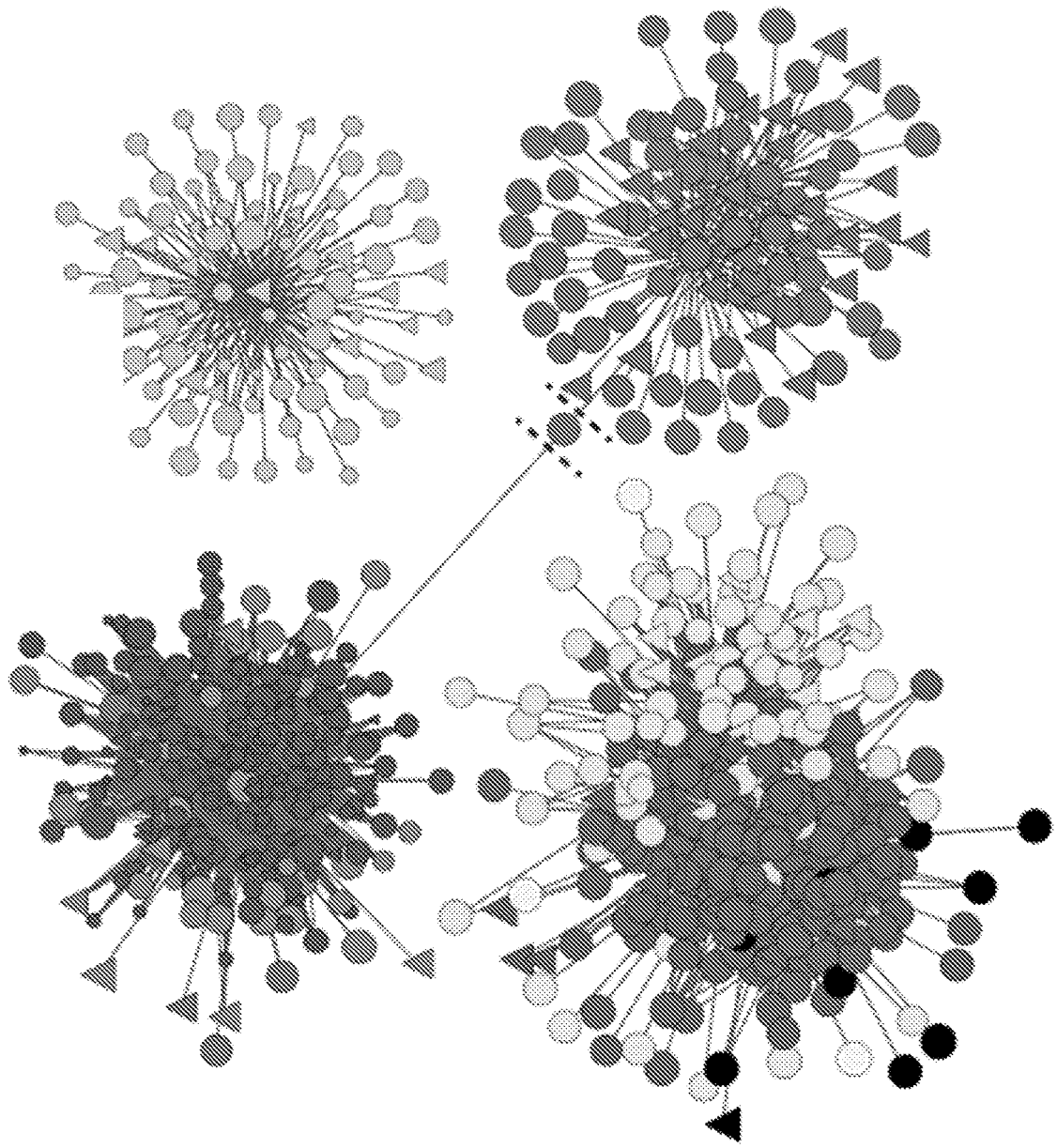
FIG. 6H: As in FIG. 6F, except for iMN gene modules significantly anti-correlated to age and spMN maturation (PC1) in the iMN expression data set. Larger nodes have gene significance values closer to −1 and are therefore more anti-correlated to age. Since there are three distinct, contiguous network clusters with no edges connecting them, they were rotated and repositioned relative to each other so that node shapes are more visible. Therefore, node-to-node spatial relationships within, but not across, contiguous network clusters are preserved. Edges that intersect with dashed lines were shortened and repositioned in order to scale the diagram for visibility. No other modifications to the layout were made.
Figure 6I:
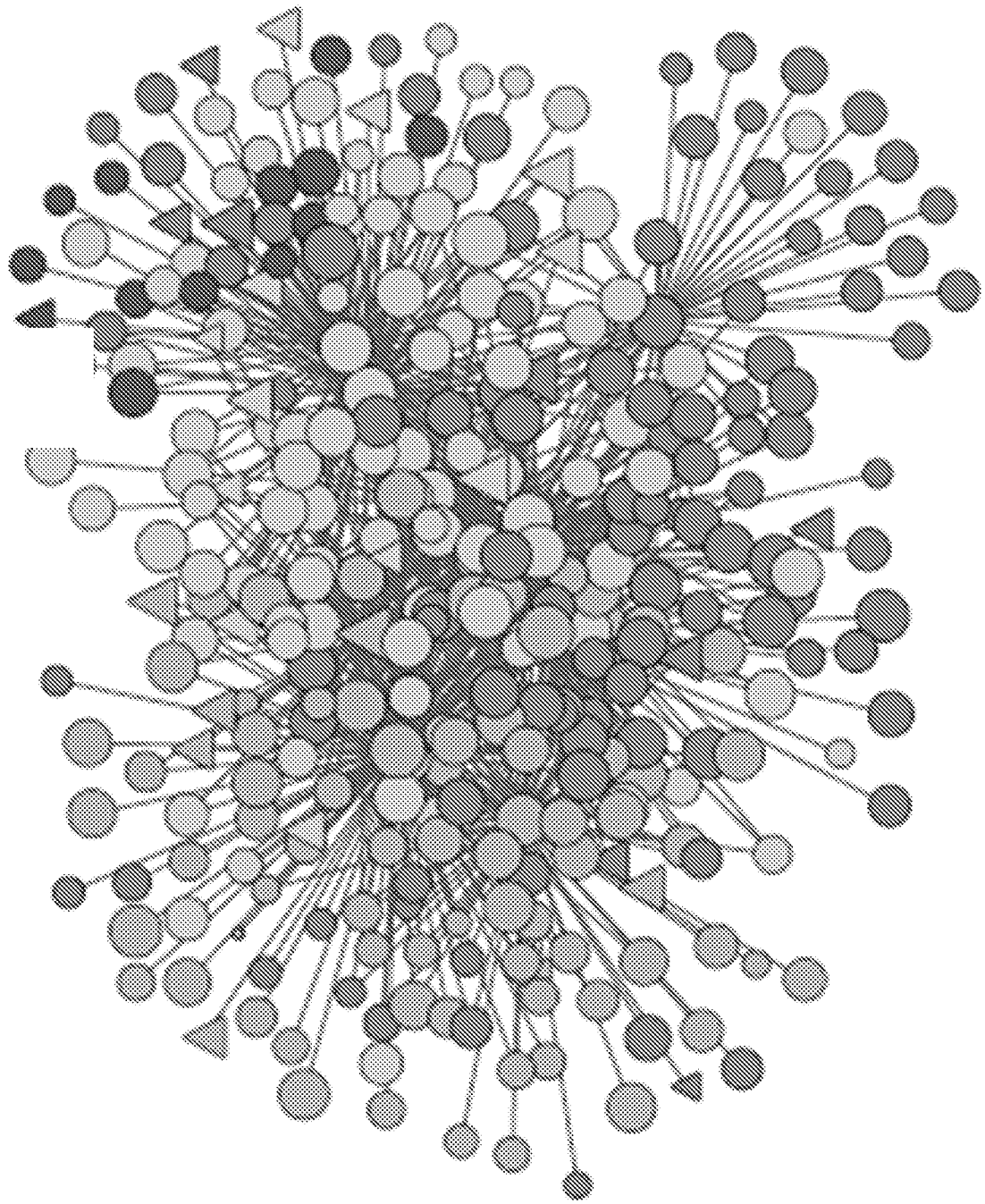
FIG. 6I: As in FIG. 6G, except for sALS gene modules significantly correlated to the sALS component in the sALS expression data set. Larger nodes have greater gene significance towards the sALS component.

When comparing the network property of gene significance, overlaps had more biologically significant roles than non-overlaps. This is particularly the case for genes classified as Age and PC1 positive and sALS negative (FIG. 6B) but not the case for genes classified as Age and PC1 negative and sALS positive (FIG. 6C). Additionally, overlaps tended to have higher intramodule membership within Age and PC1 positive modules as well as within sALS negative modules (FIG. 6D). These observations further support a more prominent role for overlaps. Lastly, intermodule membership for each gene measures its expression correlation to the eigengenes of other modules that significantly correlate or anti-correlate to the same sample trait. This metric can be used to identify hub genes that connect multiple modules. This comparison showed that overlaps tended to have higher intermodule membership within Age and PC1 positive modules as well as within sALS negative modules (FIG. 6E), suggesting that they are functionally conserved as intermodule hub genes. These gene network properties can be simultaneously visualized as network maps (FIGS. 6F-I). For Age and PC1 positive modules, a network map filtered for the strongest gene-to-gene connections comprised of multiple interconnected modules (FIG. 6F). This network contained far more overlaps (circular nodes) than non-overlaps (triangular nodes), and overlaps tended to have greater gene significance with respect to age (relative node size) and also tended to have greater intramodule membership (central positions within like-colored clusters). Non-overlaps demonstrated a lower degree of intramodule membership compared to overlaps, as they occupied more peripheral positions within like-colored clusters (FIG. 6F). The same trends were observed in sALS negative modules (FIG. 6G), Age and PC1 negative modules (FIG. 6H), and sALS positive modules (FIG. 6I). Altogether, these data illustrate a highly conserved function of hub genes within networks associated with MN maturation and aging that are also targeted in sALS.

Example 12

Discussion

In this study, the Inventors directly compared genome-wide expression profiles of human-derived iPSCs, iMNs, fetal and adult spinal cords, and adult spMNs. From this composite data set, the Inventors described gene co-expression network behaviors as they relate to spMN development, maturation, age, fALS, and sALS. The Inventors show for the first time that iPSC-derived MNs are transcriptomically more similar to fetal rather than adult tissues, and that the signature from iPSC to mature spMNs can be described based on the expression of just 20 key genes.

Another key finding from this analysis was that genetic variants associated with MN disease and fALS were enriched specifically in modules that significantly correlated with spMN maturation and age. Thirdly, the Inventors also revealed the expression kinetics of pathways during spMN maturation and aging, and how ALS caused expression changes that either exacerbated or antagonized the trajectory of those endogenous expression patterns. In many models where iPSCs have been used to generate tissues such as heart, pancreas or the nervous system, they have been found to represent an immature or fetal stage of development. This is presumably due to the resetting of the epigenetic state to that of an embryo during iPSC production, which can occur even when the patient was over 90 years old. In the current study the Inventors wholly demonstrate that iPSC derived MNs are more similar to their fetal in vivo counterparts than adult MNs based on their transcriptome. In the Inventors' network analysis, the Inventors developed a method to reliably predict the state of spMN maturation by reducing the key number of hub genes to 20 that drove principal component analysis. Through an unbiased, genome wide approach, the Inventors identified network hub genes that have previously been described as either markers or functional drivers of neuronal development or maturation. For example, DCX, NEFH, and SNAP25 have previously been described as histological markers of early, intermediate, and late neuronal maturation, respectively. Additionally, loss of function mutations in SCN1A have been implicated in a failure of interneurons to develop mature action potentials in Dravet syndrome, and ASCL1 was shown to be the key pioneering transcription factor driving direct conversion of fibroblasts to induced neurons, which subsequently demonstrate slower maturation kinetics. Using only these 20 key genes, the Inventors effectively reduced the number of genes tested and thereby circumvented microarray platform-specific biases that confounded the accurate comparison of maturation states across samples. This technique will be extremely helpful as the Inventors develop more efficient ways to mature MNs in the dish. Furthermore, this approach can be applied to iPSC-derived cell types other than spMNs, such as upper MN models of ALS, given the relative abundance of transcriptomic data available for in vivo brain tissues at different developmental stages. In order to use MNs to model neurological disease it may be necessary to age them in the dish. Prior attempts have been described to simulate aspects of aging in iPSC-derived neurons by either prolonging time in culture or introducing agents of cellular stress by chemical or genetic means so as to induce late-onset, neurodegenerative phenotypes. Notably, these strategies are able to concomitantly bring about age-related molecular features along with phenotypes believed to be associated with neurodegeneration. However, the Inventors' data indicate that the molecular processes of neuronal aging and neuronal maturation are distinct, substantiating a perspective held by others. Therefore, it is not clear whether these techniques accelerated the progression of iPSCs from the embryonic to a mature neuronal state or simply induced isolated aging pathways in immature cells. Since cellular age is collectively a multi-faceted, syndromic condition, it is most effectively assayed in a systems wide manner. Thus, the global gene expression and network analysis the Inventors have employed here is well suited to assay cellular maturity as well as cellular age and can provide a useful method to comprehensively assess iPSC-derived tissue models undergoing stress-induced conditions.

More recent studies using direct reprogramming techniques have shown that the matured epigenetic state may be maintained when neurons are directly converted from aged adult human fibroblasts. While MNs have been directly converted from embryonic and fetal human fibroblasts, it would be of interest to see if similar techniques performed on aged human fibroblasts indeed maintain a more mature state through the transition process. However, one challenge with direct conversion methods and disease modeling will always be the genomic stability of the primary somatic cells (such as fibroblasts) upon expansion in culture and subsequent differentiation when compared to iPSCs, which express telomerase and can be expanded indefinitely in culture. Nevertheless, the Inventors provide a data set and method that future studies can directly apply in addressing these questions.

There are a growing number of genetic variants reported to be associated with a multitude of human diseases in the ClinVar database. Strikingly, a few modules that correlated with maturation or age (or both) enriched for genes with variants documented as pathogenically linked to ALS or MN disease. This observation lends strong evidence for maturation- and age-associated networks and pathways acting as causative effectors of late onset diseases. In the future, characterization of novel genetic variants classified as risk factors may also explain how they act collectively within these networks to modify the penetrance or onset time of disease in individual patients. The mitochondrial free radical theory of aging posits that as cells age, the stability of their electron transport chain activity declines, thereby producing an accumulating amount of reactive oxygen species that cause oxidative damage to all biomolecules in the system, including nuclear and mitochondrial DNA. The Inventors' analysis revealed that the mitochondrial respiratory chain components decreased in expression during spMN maturation rather than during aging, consistent with observations seen in blood from ALS patients. Additionally, DNA repair pathways also decreased in expression as spMNs mature, suggesting a reduced ability to mitigate oxidative damage to DNA. The Inventors' analysis also revealed that sALS further downregulated mitochondrial respiratory chain genes. Thus, the combination of spMN maturation and sALS can exacerbate a condition in which spMNs are prone and vulnerable to oxidative damage. Notably, these mitochondrial components were also previously reported to be downregulated in mtSOD1 iMNs (Kiskinis et al., 2014), indicating that despite being in a fetal context, some key pathways can already be affected.

Interestingly, the Inventors also highlighted a dynamic expression pattern of gene networks associated with antigen presentation and immune response. Whereas these processes increased in expression as spMNs mature, they decreased in expression as spMNs age. This model is consistent with the role of microglia and astrocytes in targeting and pruning synaptic connections during neuronal maturation, but proposed to be hyperactive in late-onset diseases. The Inventors also observed that the immune response and complement activation pathways are upregulated in sALS. In summary, sALS antagonizes the endogenous expression pattern of these immune activation pathways as well as that of protein translation and degradation. These observations therefore support the idea that the expression kinetics for these pathways serve a homeostatic, protective role in aging spMNs that can be derailed by ALS, resulting in neurodegeneration. In addition to identifying pathways dysregulated by ALS, the Inventors' network analysis provided another dimension to the role of genes within maturation and aging expression networks. The scale-free architectures of all natural systems are robustly tolerant against errors, attacks, and perturbations to the majority of its nodes, but at the cost of being vulnerable to disruptions targeting their hub nodes. The Inventors' observation that sALS preferentially disrupts hub genes within maturation and aging expression networks underscores its devastation to critical cellular systems. Understanding which central genes are the most vulnerable to ALS will guide effective therapies aimed at rescuing the function of these targeted hub genes.

Altogether, the Inventors' findings support a strong interaction between gene networks and pathways that are associated with spMN maturation and aging and those that are affected in ALS. This suggests that reenacting the endogenous spMN maturation and aging pathways in iMNs can sensitize them to ALS-induced dysfunction. Nevertheless, it is possible that achieving a mature and aged state in iMNs is superfluous to effective ALS modeling. Strong, disease-relevant phenotypes have been gleaned from immature iMNs, including RNA foci, protein inclusion bodies, altered electrophysiology, nuclear pore deficits, and cell death. While some of these phenotypes have spurred attempts at therapeutic strategies in ALS patients, it remains to be seen whether they are indeed relevant to the disease etiology in adults. For instance, if ALS patients treated with retigabine, an antiepileptic drug that reduces hyperexcitability in mtSOD1 iMNs, demonstrate a positive response to the treatment, this would validate the efficacy of current iMN models in predicting events that occur in adult spMNs. Otherwise, maturation and aging pathways should be considered as strong modifiers of disease presentation, and the Inventors' present findings lay the groundwork for future efforts to achieve a higher fidelity model of the molecular, pathological events of ALS as they occur in vivo.

The advent of induced pluripotency in cells isolated from a patient marks a major turning point in the field of regenerative medicine. However, the challenge remains to properly harness iPSC technology to faithfully isolate in vitro the desired in vivo cellular state to be examined. We now have a method to assess developmental maturity of in vitro motor neuron cultures derived from iPSCs. This methodology is widely applicable to other neural and nonneural cell types. Future aims include integrating expression data with genetic (DNA motifs) and epigenetic (ChIP-seq) data sets from in vivo cell types to help find regulators of maturation or aging. Importantly, this methodology may also uncover critical pathways or disease associated genetic variants that play a role in disease progression. Defining combinatorial epigenetic and proteomic states present in our motor neuron cultures will further aid strategies to promote cellular maturation and perhaps aging in vitro.

Example 13

Validation Studies

The Inventors have validated 20 key gene markers that are capable of assessing the maturation state of pluripotent stem cell-derived motor neurons. Using quantitative polymerase chain reaction (qPCR), one can recapitulate the results that found using microarray data. Namely, by measuring NEFH, TNS1, SCN1A, SPOCK3, SNAP25, RFX4, SST, HOXB8, DCX, ASCL1, ILF2, TOP2A, MSH2, DLGAP5, L1TD1, TDGF1, POU5F1, FXYD5, FZD7, PHLDA2.

Figure 14:
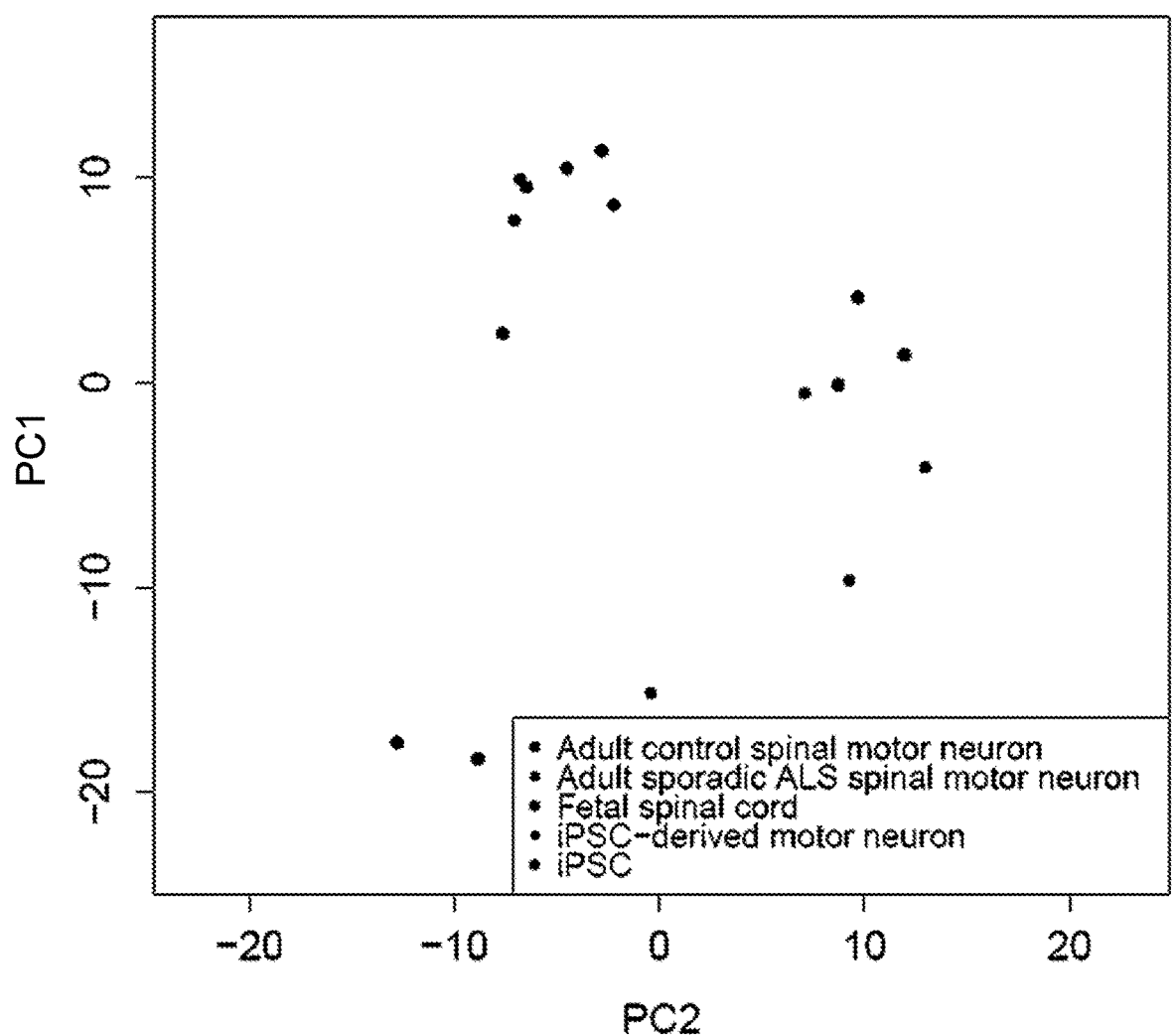
FIG. 14. Using quantitative polymerase chain reaction (qPCR), recapitulates the results that found using microarray data. Namely, measuring gene expression in spinal motor neurons from adults with and without sporadic ALS, and iPSC-derived motor neurons from a control cell line over a time course of differentiation, starting at day 0, and progressing through day 6, 12, and 18. Principal component analysis (PCA) that shows the iPSC-derived motor neurons "moving" towards fetal spinal tissue. The Inventors are able to demonstrate this maturation scale using the expression data for these 20 genes from RNA-sequencing data.

This assay was tested on a distinct set of samples that were different from the samples used in our aforementioned study, by including spinal motor neurons from adults with and without sporadic ALS, and iPSC-derived motor neurons from a control cell line over a time course of differentiation, starting at day 0, and progressing through day 6, 12, and 18. As shown in FIG. 14, principal component analysis (PCA) shows the iPSC-derived motor neurons "moving" towards fetal spinal tissue. The Inventors are able to demonstrate this maturation scale using the expression data for these 20 genes from RNA-sequencing data and are currently designing probes to perform this assay on the Nanostring platform.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are nucleic acid sequences associated with neurodegenerative disease and/or conditions, methods of detecting nucleic acid sequences associated with neurodegenerative disease and/or conditions, prognostic and/or diagnostic panels that include nucleic acid sequences associated with neurodegenerative disease and/or conditions, and the techniques used to manufacture, express, modulate the function or expression of nucleic acid sequences associated with neurodegenerative disease and/or conditions, and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A microarray device comprising: a set of nucleic acid probes, wherein each nucleic acid probe hybridizes to a different marker gene among the following marker genes selected to represent spinal motor neuron (spMN) maturation and embryonic spMN development: NEFH, TNS1, SCN1A, SPOCK3, SNAP25, RFX4, SST, HOXB8, DCX, ASCLI, ILF2, TOP2A, MSH2, DLGAPS, LITD1, TDGF1, POUSF1, FXYD5, FZD7, and PHLDA2, wherein the microarray device is attached to 100 or fewer nucleic acid probes, and comprises a planar surface, wherein the nucleic acid probes are coupled to the planar surface of a solid support in different, known locations.

2. The microarray device of claim 1, in combination with a biological sample comprising RNA isolated from a population of cells comprising neuronal cells.

3. The microarray device of claim 2, wherein the neuronal cells are obtained from a subject.

4. The microarray device of claim 3, wherein the subject is afflicted with a neurodegenerative disease and/or condition.

5. The microarray device of claim 4, wherein the neurodegenerative disease and/or condition comprises Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, or Charcot Marie Tooth.

* * * * *